Figure 3:
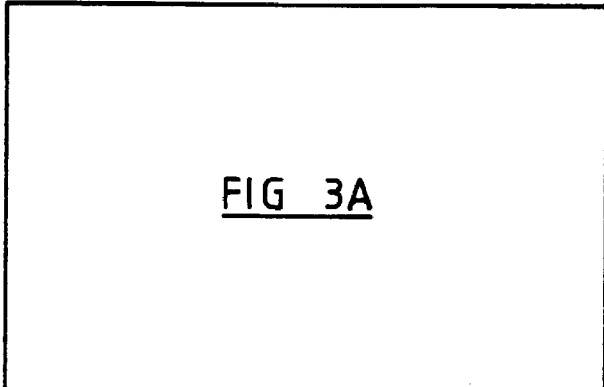
Figure 3:
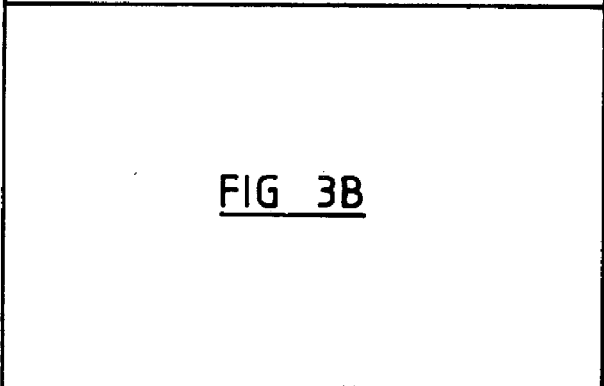
Figure 3:
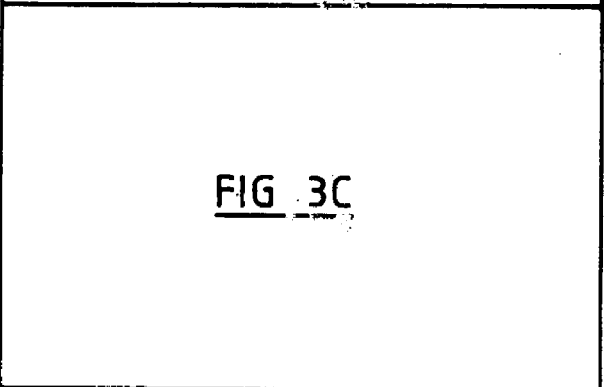
Figure 3:
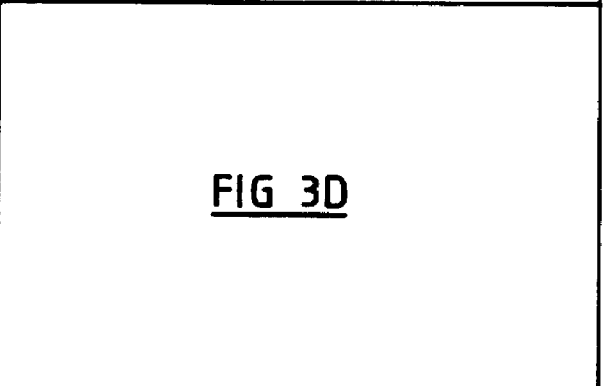

United States Patent [19]

Bowtell

[11] Patent Number: 5,843,646
[45] Date of Patent: Dec. 1, 1998

[54] DNA MOLECULES ENCODING MURINE SON OF SEVENLESS (MSOS) GENE AND MSOS POLYPEPTIDES

[75] Inventor: David Douglas Lawrence Bowtell, Coburg, Australia

[73] Assignee: Howard Florey Institute of Experimental Physiology and Medicine, Victoria, Australia

[21] Appl. No.: 290,731

[22] PCT Filed: Feb. 17, 1993

[86] PCT No.: PCT/AU93/00068

§ 371 Date: Oct. 17, 1994

§ 102(e) Date: Oct. 17, 1994

[87] PCT Pub. No.: WO93/16179

PCT Pub. Date: Aug. 19, 1993

[30] Foreign Application Priority Data

Feb. 17, 1992 [AU] Australia ................................ PL 0921

[51] Int. Cl.⁶ .............................. C12Q 1/68; C12N 15/63; C07H 21/04; C07K 14/47

[52] U.S. Cl. .............................. 435/6; 435/320.1; 436/89; 530/350; 536/23.5

[58] Field of Search .................... 435/69.1, 172.3, 435/320.1, 6; 536/23.1, 23.2, 23.5, 23.6, 24.1, 24.3, 24.31, 24.33; 935/1, 9, 11, 23; 436/89; 530/350

[56] References Cited

PUBLICATIONS

Bonfini et al. (Jan. 1992) Science 255:603–606.
Bowtell (Jul. 1992) Proc. Natl. Acad. Sci. USA 89:6511–6515.

*Primary Examiner*—George C. Elliott
*Assistant Examiner*—Robert Schwartzman
*Attorney, Agent, or Firm*—Sughrue, Mion, Zinn, Macpeak & Seas, PLLC

[57] ABSTRACT

Isolated DNA molecules comprising a nucleotide sequence encoding murine son of sevenless gene 1 (mSOS1) polypeptide and comprising a nucleotide sequence encoding murine son of sevenless gene 2 (mSOS2) polypeptide are disclosed, as well as isolated mSOS1 polypeptide and isolated mSOS2 polypeptide, and diagnostic methods using the same.

13 Claims, 62 Drawing Sheets

FIG 1

| FIG 1A |
|--------|
| FIG 1B |
| FIG 1C |
| FIG 1D |
| FIG 1E |
| FIG 1F |
| FIG 1G |
| FIG 1H |
| FIG 1I |
| FIG 1J |
| FIG 1K |
| FIG 1L |
| FIG 1M |
| FIG 1N |
| FIG 1O |
| FIG 1P |
| FIG 1Q |
| FIG 1R |
| FIG 1S |
| FIG 1T |
| FIG 1U |

```
2611 GAGCTGAACAACTTCAATGGTGTCCTGGAAGTTGTCAGTGCTATGAACTCCTCACCTGTTTACAGACTAGACCACACATTTGAGCAAATA
     ----+----|----+----|----+----|----+----|----+----|----+----|----+----|----+----|----+----|  +2700
     CTCGACTTGTTGAAGTTACCACACAGGACCTTCAACAGTCACGATACTTGACGACTGGACAAATGTCTGATCGTCGTGTGTAAACTCGTTTAT a   E  L  N  N  F  N  G  V  L  E  V  V  S  A  M  N  S  S  P  V  Y  R  L  D  H  T  F  E  Q  I  -
                                                   B              P
                                                   s              H
                                                                  I

2701 CCAAGCCAGACAAAAGAAAATTTAGAAGAAGCTCATGAATTGACTGAAGATCACTATAAGAAATATTTGGCAAAACTCAGGTCTATTAAT
     ----+----|----+----|----+----|----+----|----+----|----+----|----+----|----+----|----+----|  +2790
     GGTTCGTCTGTTTTCTTTTAAATCTTCTTCGAGTACTTAACTGACTTCTAGTGATATTCTTTATAAACCGTTTTGAGTCCAGATAATTA a   P  S  R  Q  K  K  I  L  E  E  A  H  E  L  S  E  D  H  Y  K  K  Y  L  A  K  L  R  S  I  N  -
                                                                                   E        B
                                                                                   c        s
     D                                                                             o P      u
     r                                                                             O s      1
     a                                                                                1 P   3
     I                                                                                0 5   6
     I                                                                                5 9   1
     I                                                                                  1 1
                                                                                        1 1
                                                                                          /
     B                                                                                B
     s                                                                                s
     u                                                                                u
     3                                                                                3
     6                                                                                6
     I                                                                                I
```

FIG 1M

```
2791 CCACCGTGTGTGCCTTTCTTTGGAATTTATCTCACAAATATCCTGAAGACAGAAGAGGGCAACCCTGAGGTCCTGAGGAGACACGGGAAA +2880
     GGTGGCACACACGGGAAAGAAACCTTAAATAGAGTGTTTATAGGACTTCTGTCTCCCGTTGGGACTCCAGGACTCCTCTGTGCCCTTT
   a  P  P  C  V  P  F  F  G  I  Y  L  T  N  I  L  K  T  E  E  G  N  P  E  V  L  R  R  H  G  K  -
                                                 G              D
                                                Ed              r
                                                a i             d
                                                e l             I
                                                 I I            I

2881 GAGCTTATTAACTTCAGCAAGAGGAGGAGAGTGGCCGAGATCACAGGCCGAGATCCAGGAACCAGCCCTACTGCTTACGGGTG +2970
     CTCGAATAATTGAAGTCGTTCTCCTCCTCTCACCGGCTCTAGTGTCCGGCTCTAGGTCTTGGTCTCGGGATGACGAATGCCCAC
   a  E  L  I  N  F  S  K  R  R  V  A  E  I  T  G  E  I  Q  Q  Y  Q  N  Q  P  Y  C  L  R  V  -

2971 GAGCCGGACATCAAGAGGTTCTTTGAAAACTTCTTGAAAAGCAGCATGGGAGAAACAGCAGTGGGAAAGAATTTACAGAGACTATCTCTGTTCAACAAATCC +3060
     CTCGGCCTGTAGTTCTCCAAGAAACTTTTGAACTTTTGTCGTACCCTCTTTGTCGTCACCCTTTCTTAAATGTCTGATAGAAGACAAGTTGTTTAGG
   a  E  P  D  I  K  R  F  F  E  N  L  N  P  M  G  N  S  M  E  K  E  F  T  D  Y  L  F  N  K  S  -
```

| FIG 2A |
| FIG 2B |
| FIG 2C |
| FIG 2D |
| FIG 2E |
| FIG 2F |
| FIG 2G |
| FIG 2H |
| FIG 2I |
| FIG 2J |
| FIG 2K |
| FIG 2L |
| FIG 2M |
| FIG 2N |
| FIG 2O |
| FIG 2P |
| FIG 2Q |
| FIG 2R |
| FIG 2S |
| FIG 2T |
| FIG 2U |
| FIG 2V |
| FIG 2W |
| FIG 2X |

```
          BB                                                                              M
          ps                                                                              m
          up                                                                              e
          11H                                                                             l
          12g
          08i
          26A
          III                                 /
       CGGGTGGCAGTGCTCAGCAGAATAGTAGAAATTCTGCAAGTATTTCAAGACTTGAATAATTTCAATGGGCTGTTGCAGATAGTGACTGCA
2431 ---+---------+---------+---------+---------+---------+---------+---------+---------+ +2520
       GCCCACCGTCACGAGTCGTCGTCTTATCATCTTTAAGACGTTCATAAAGTTCTGAACTTATTAAAGTTACCCGACAACCTCTATCACTCACGT
a       R  V  A  V  L  S  R  I  V  E  I  L  Q  V  F  Q  D  L  N  F  N  G  V  L  E  I  V  S  A  -
                             B                                                  P
                             s                                                  s
                             p                                                  t
          H                  1                                                  I
          i                  4
          n                  0
          c                  7
          I                  I
          I                  I
       GTcaactCCGTGTCAGTGTACAGGCTAGACCACACCGTTTGAGGCACTGCCAGGAAAGGAAGCCGGAGAATTTTGGATGACGcTGTGGAACTA
2521 ---+---------+---------+---------+---------+---------+---------+---------+---------+ +2610
       CAgttgAGGCACAGTCACATGTCCGATCTGGTGTGACCTCCTTGCAAACTCCGTGACGGTCCTTTCGCCTCTTAAAACCTACTGCgaCACCTTGAT
a       V  N  S  V  Y  R  L  D  H  T  F  E  A  L  Q  E  R  R  R  R  I  L  D  D  A  V  E  L  -
```

```
        HindII                                                                     BbpMI
         |        Tag1                                                              |
         |         |                                                                |
3061 CCAACGCCCTCTGGAAGAGAGCCTTATAAGATAAGCTTTAGCCCGGATCGCTGAGACAGAGCTAGAATCAACAGTGTCTGCCACCAACCTCC +3150
     GGTTGCGGGAGACCTTCTCTCGGAATATTCTATTCGAAATCGGGCCTAGCGACTCTGTCTCGATCTTAGTTGTCACAGACGGTGGTTGGAGG
      P  T  P  L  E  R  E  P  Y  K  I  S  F  S  R  I  A  E  T  E  L  E  S  T  V  S  A  P  T  S  -

DraI                BbpMI
                                                        |                   |
                                                        |                   m
                                                        |                   |
3151 CCCAACACTCCACCCCACCAGTGTCTGCTTCTTCAGACCACAGCGTGTTTCTAGATGTGGACCCTCAATAGCTCCTGTGGCAGCAAC +3240
     GGGTTGTGAGGTGGGGTGGTCACAGACGAAGAAGTCTGGTGTCGCACAAAGATCTACACCTGGGAGTTATCGAGGACACCGTCGTTG
      P  N  T  P  S  T  P  P  V  S  A  S  S  D  H  S  V  F  L  D  V  D  L  N  S  S  C  G  S  N  -

FIG 2N
```

```
3241 ACCATCTTTGCTCCAGTCCTCTTGCCACACTCAAAGACTTTCTTCAGCTCATGTGGAAGTTtACACAAACTGAGTGAAGAGCCACTAATT +3330
     TGGTAGAAACGAGGTCAGGAGAACGGTGTGAGTTTCTGAGTTTCTGAAAGAAGTCGAgTACACCTTCAAaTGTGTTTGACTCACTTCTCGGTGATTAA a    T  I  F  A  P  V  L  P  H  S  K  T  F  F  S  S  C  G  S  L  H  K  L  S  E  E  P  L  I  -

3331 CCTCCTCCGCTTCCCCCTCCGGAAAAAGTTTGATCATGATGCTCTCAATTCCAAGGGAGCTGTGAAATCTGATGATGACCCTCCTGCTATT +3420
     GGAGGAGGCGAAGGGGGAGCCCTTTTCAAACTAGTACTACTACGAGAGTTAAGGTTCCCTCGACACTTTAGACTACTACTGGGAGGACGATAA a    P  P  P  L  P  P  R  K  F  D  H  D  A  L  N  S  K  G  A  V  K  S  D  D  D  P  P  A  I  -
```

```
4591 GAAAATAGAATGAAATAATAGAATGCACTgTgTTTTATTATTTGTTAAAATTATAACAGTTCTACATAACCTGATTATAGAAGAAGGGC +4680
     ----+----|----+----|----+----|----+----|----+----|----+----|----+----|----+----|----+----|
     CTTTTATCTTACTTTATTCTTACGTGACACAAATAATAAAACAATTTAATATTTGTCAAGATGTATTGGACTAATATCTTCTTCCCG
                B
                s
                m
                I

4681 ATGTGTTCATTAAGATGTGCCTTTGTTTGTCAGTGTATGGTGTTTAGCTAATCATTGTTGCCTATTGATTGCCTATTATTTGGGAaG +4770
     ----+----|----+----|----+----|----+----|----+----|----+----|----+----|----+----|----+----|
     TACACAAGTAATTCTACACGGGAAACAAACGTCACATACCACAAATCGATTAGTAACAAATCGATTACTAAACGGATAATAAACCCTtC
                              B
                              s
                              p
                              1
                              4
                              0
                              7
                              I

4771 ACAAATTAATATGCCATATATGTACAGTTTATTTTATATTGTATATATTTAAAGATAATGCTAATAACCTCTATAAATGTAAGTGACTTG +4860
     ----+----|----+----|----+----|----+----|----+----|----+----|----+----|----+----|----+----|
     TGTTTAATTATACGGTATATACATGTCAAATAAATAAATATAACATATATAAATTTCTATTACGATTATTGGAGATATTTACATTCACTGAAC
     A
     s
     e
     I

FIG 2U
```

FIG 2V

```
5041 TTATTAAATTTTtAATCAGACAGGATAAGCTTTGCCATTTGCCATACTATCATTCAAAGTGATCAAGGTATGTTATGCTGATAGT
     ----+---------+---------+---------+---------+---------+---------+---------+---------+ +5130
     AATAATTTAAAAAaTTAGTCTGTCCTATTTCGAAACGGGTAAACCTATGATAGTAAGTTTCACTAGTTCCATACAATACGACTATCA
                                                Hind I 5131 GCAGTAGCAGCCATTGTAAAGTAGCCAAAAGCCACGTTGTTTATCTACTCGGTCTGTGGCCTTTACTGTGCTTtGTATCAGAGTTCTTAA
     ----+---------+---------+---------+---------+---------+---------+---------+---------+ +5220
     CGTCATCGTCGGTAACATTTCATCGGTTTTCGGTGCAACAAATGACCAGACACCCGGAAAATGACACGAAaCATAGTCTCAAGAATT
                  AseI 5221 CAAGaTTAATAAATCACCCTCAGTCTTAATTTGT
     ----+---------+---------+---- 5253
     GTTCtAATTATTAGTGGAGTCAGAATTAAACA
```

FIG 2W

FIG 2X

```
                         10         20         30
5_lmel
2_1_16  AGTGAAGATCACTATAAGAAAATATTTGGCAAATCAATCCGCCTTGTGTG
          2690       2700       2710       2720       2730       2740

40         50         60         70         80         90
5_lmel  CCTTTTTGGAAATATATTAACAAAATATTCTGAAGACTGAAGAAGGAAGAACAGTGACTTT
2_1_16  CCTTTCTTGGAATTTATCTCACAAATATCCTGAAGAAGACAGAAGAGGGCAACCCTGAGGTC
          2750       2760       2770       2780       2790       2800

100        110        120        130        140        150
5_lmel  CTAAAGAGGAAAGGCAAAGATTTGATCAATTTCAGTAAGAGGAGGAAAGTGGCTGAAATA
2_1_16  CTGAGGACACGGGAAAGAGCTTATTAACTTCAGCAAGAGGAGCAGTGAGTGGCCCGAGATC
          2810       2820       2830       2840       2850       2860

160        170        180        190        200        210
5_lmel  ACTGGAGAGATCCAGCAGTATCAGAACCAACCGTACTGCTTACGGACAGAACCAGAAATG
2_1_16  ACAGGCGAGATCCAGCAGTACCAGAACCAGCACCCCTACTGCTTACGGGTGGAGCCGACATC
          2870       2880       2890       2900       2910       2920
```

FIG 3A

```
5_lmel  AGGAGATTCTTTGAAAAACCTCAGCCCCATGG---AATTTTATCTGAAAGAGTTTACAGAT
             ||| ||||||||||||||||| || ||||||   || |||| |||||||| ||||||||||
2_1_16  AAGAGGTTCTTTGAAAACTTGAATCCAATGGGAAATCCAATGGGAAAGAATTACAGAC 5_lmel  TATTTGTTCAACAAATCATTAGAAATCGAACCCCCGAAACTGCAAACAACCACCTCGATTT
             ||| |||||||||||| || |||| ||| ||||| ||||| |||||| |||||| ||||
2_1_16  TATCTGTTCAACAAATCCCCTAGAATAGAACCCCGGCACCCTAGCCTTCTTCCGAGATTC 5_lmel  CCTAGGAAGTCAACCTTTTCCTTAAAATCTCCTTGAATAAGGCCCCAATGCTGGCNGCCAT
             || ||| |||| ||||| || ||||||||||| |||| || |||||||||||| |||||
2_1_16  CCAAAAAATACAGCTATCCCCTAAAATCTCCTGGTGTTCGTCC-----ATCAAATCCAA 5_lmel  GGCTCTNCCTCAGGCACGCTACGAGGTCACCAACGGCNTCTGGAANGAGAGCNNTATNNG
             |                    ||||| |||||| ||| ||||| |||||||||| ||||
2_1_16  GAC-----CAGGAACCATGAGA---CATCCCACACCTCTGCAGGAGCCAAGAAAA
```

FIG 3B

```
                    450           460           470           480           490           500
5_lme1    ATANGCTTNNMGCNGGATCGCTGAGACAGAGCTNGAATCAACMGTGTCTGCAACCTC
           ||  ::||  | ::::|| ||||    ||| ||    |||:|||   | |||||||||
2_1_16    ATTAGC-TACAGTCGGATTCCTGAAAGTGAGACGGAAAGCCACAGCCATCTGCACAAACTC
                    3160          3170          3180          3190          3200          3210

510           520           530           540           550           560
5_lme1    CCCCAACACTCCA---TCCACCCCAGTRTCT-GCTTCTTCAG-ACCAGCGGTGTTK
          ||||  || ||||    | ||||||||| ||| ||||| |||| |||||   |||| :
2_1_16    CCCTCGGACCCCCACTGACGCCCCCCTGCATCTGGCACCTCCAGCAACACAG-ATGTTT
                    3220          3230          3240          3250          3260          3270

570           580           590           600           610           620
5_lme1    CTAGATGTGGACCTCAATAGCTCCTGTGGCAGCAACACCATCTTTGCTCCAGTCCTCTTG
           |
2_1_16    GCAGCCTGCTTCGATTCTGACCACTCGGCCAAGCCCCTTTCATTCAAGATCTGCTTCAGTCT
                    3280          3290          3300          3310          3320          3330

790           800           810           820           830           840
5_lme1    TGTAAAAAGTACTAAAATACTATGTCTTTTTGAATAAAT---TAAAACCTTTACAAATA
          |||| |||||  ||  | ||| |||| |||| ||| ||    |  | ||| |||||| |
2_1_16    AATTTATTGGAACAGTAAGAGGTAAAGCAATGAAAAATGGGTCGAATCCAATCACTAAGA
                    2120          2130          2140          2150          2160          2170

FIG 3C
```

```
                     850            860             870            880             890
5_lmel   CTATTCCAGTGTCAATGACTACA------TATGGCCAAGGTCATTGAGGAGTTCTGCAT
           ||     ||   ||  ||              ||||||||| ||||| |||||| ||||
2_1_16   TAATCCAAGGAAAAAATTGCAAGAGACCCCAGGTCATAACATTACATTTCAGA
                     2180           2190            2200           2210            2220           2230

900            910             920            930             940            950
5_lmel   TTTCCAGCCAGAGGCAGTCTATACAGTGGGCGGTGCGAAACCTCCCGTTTGTAAGTCTTTG
           |||||||||| |||||| |||||||||||  ||||    ||||||| ||||| |||| |
2_1_16   GCTCACCTCCCACAGTTGAGTGGCCACATAACCAGACCTGGGCACAAGAGACTTTTGACT
                     2240           2250            2260           2270            2280           2290
```

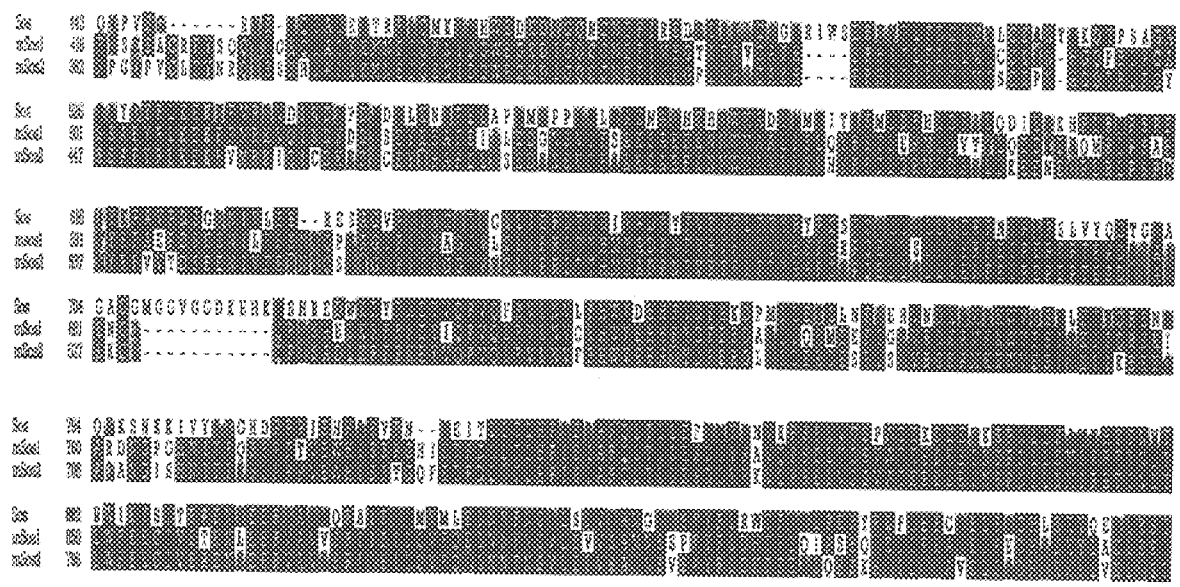
FIG 4A(2)

cat25
sat25-47%
ste6-26%
bud5-14%
Sos-29%
mSos1-31%
mSos2-28%

DNA MOLECULES ENCODING MURINE SON OF SEVENLESS (MSOS) GENE AND MSOS POLYPEPTIDES

This invention broadly relates to polynucleotides encoding mammalian Sos gene and protein product thereof.

Protein tyrosine kinases (PTKs) are important regulatory proteins that control many aspects of cellular growth, differentiation, and metabolism (Cantley et al., 1991). Many polypeptide hormones are known to regulate the metabolism, differentiation, and growth of target cells by binding transmembrane receptors that possess intracellular PTK domains (Cross and Dexter, 1991).

The biological effects of PTK activation throughout mammalian cells may be mediated, at least in part, via the Ras proteins (Simon et al., Cell, Vol. 67, 701–716). Ras genes and protein products are associated with a variety of human tumours, particularly where Ras is overproduced or inappropriately expressed.

Simon et al. (Supra) identified a Drosophila gene, associated with protein tyrosine kinase signalling. The Drosophila son of sevenless (Sos) gene product is homologous to a yeast protein (CDC25), which is an activator of guanine nucleotide exchange by Ras proteins. The data of Simon et al. (Supra) indicates that tyrosine kinase signalling is effected by activation of the Sos protein (such as via tyrosine phosphorylation, or some form of indirect stimulation), which then activates Ras proteins by exchange GDP for GTP.

We have surprisingly identified the mammalian Sos gene, hereinafter referred to as mSos, fragments thereof, which have homology to various guanine exchange factors.

In accordance with a first aspect of this invention, there is provided a polynucleotide encoding an mSos gene, or a fragment or analogue thereof. This invention includes any mammalian Sos including human, domestic animal (sheep, cattle, etc) and companion animal (cats, dog, etc) mSos.

The term polynucleotide as referred to herein refers to DNA and RNA, and derivatives thereof as are well known in the art Partial nucleotide sequences of the murine mSos genes mSos1 (SEQ ID NO:1) and mSos2 (SEQ ID NO:3) are shown in FIGS. 1 and 2. This invention includes such polynucleotide sequences and their full length equivalents, as well as analogues thereof where one or more nucleotides are substituted, deleted or inserted. Methods for the generation of polynucleotide analogues are well known in the art.

This invention includes vectors, such as plasmid, viral or other vectors as are well known in the art, which include a polynucleotide encoding mSos or a fragment or analogue thereof.

In another aspect of this invention, there is provided an mSos polypeptide or fragment or analogue thereof. The amino acid sequence of two murine mSos polypeptides, referred to as mSos 1 (SEQ ID NO:2) and mSos 2 (SEQ ID NO:4) are shown in FIGS. 1 and 2, compared to the drosophila Sos protein product. This invention extends to any mammalian mSos polypeptide, fragment or analogue thereof, including human, domestic animal and companion animal mSos polypeptide.

Reference to mSos polynucleotide fragments, or mSos polypeptide fragments, is to be taken to mean fragments which are unique to mSos. Such fragments will generally comprise in excess of twenty nucleotides, or 20 amino acids, and in particular correspond to a central domain of about 430 amino acids, which is homologous to a number of yeast guanine nucleotide exchange factors (as depicted in FIGS. 3a and 3b (SEQ ID NOS:1 and 3)).

Analogues of mSos polypeptides include amino acid modifications, deletions, substitutions, derivitizations and insertions of one or more amino acids.

It is stressed that this invention extends to mammalian Sos (mSos), in particular human. While this invention is exemplified with reference to murine Sos, the invention is clearly not so limited. Reference to mSos means any mammalian Sos gene or polypeptide, which may be isolated and characterised in accordance with this invention. For example, human mSos polynucleotides may be isolated by hybridization of murine mSos polynucleotides or fragments thereof to human cDNA or genomic sequences followed by isolation and characterisation of hybridising species. Mammals may have several forms of mSos, all of which are involved as regulators/effectors of tyrosine kinase signalling. All such forms of mSos are within the scope of this invention.

Mutations in the natural mammalian Sos genes, and gene products, may result in specific genetic defects, or tumour formation, given the role of mSos in PTK activation via Ras genes and protein products.

Accordingly, this invention extends to a method of detecting mutant mSos genes in an individual associated with a pathological phenotype (where pathological phenotype refers to any pathological condition), which method comprises comparing the nucleotide sequence or chromosomal location or structure of a suspected mutant mSos gene with a reference non mutated mSos gene as herein described. Suitable comparisons may be made by nucleotide sequencing, restriction fragment polymorphism, analysis of amplified products (such as by PCR), and other well known techniques in the art. Such methods may be used in genetic counselling, prenatal diagnosis or the like.

According to a further aspect of this invention there is provided an antagonist of mSos which comprises a compound having the same or similar three-dimensional structure as an mSos polypeptide or a fragment thereof, which blocks the interations between mSos and its substrate in the PTK signalling pathway. The invention further relates to a polynucleotide capable of blocking transcription or translation of mSos or fragments thereof. The polynucleotide may be in the form of a triple helix forming polynucleotide, an antisense polynucleotide or a ribozyme, as are well known in the art.

This invention will now be described by way of example only, with reference to the following non-limiting Figures and Examples. In the Figures:

FIG. 1: shows the nucleotide sequence (SEQ ID NO:1) and predicted amino acid sequence (SEQ ID NO:2) of the mSos 1 gene;

FIG. 2: shows the nucleotide sequence (SEQ ID NO:3) and predicted amino acid sequence (SEQ ID NO:4) of the mSos 2 gene;

FIG. 3: shows the partial nucleotide sequence of mSos 1 and mSos 2 wherein the nucleotide sequences are aligned to maximise homology;

FIG. 4a: Predicted amino acid sequence of the mSos1 (SEQ ID NO:6) and mSos2 (SEQ ID NO:4) genes and their aligned with Drosophila Sos4(SEQ ID NO:5). Identical residues are in black boxes, conservative substitutions in grey boxes.

Figures 4A, 4B:
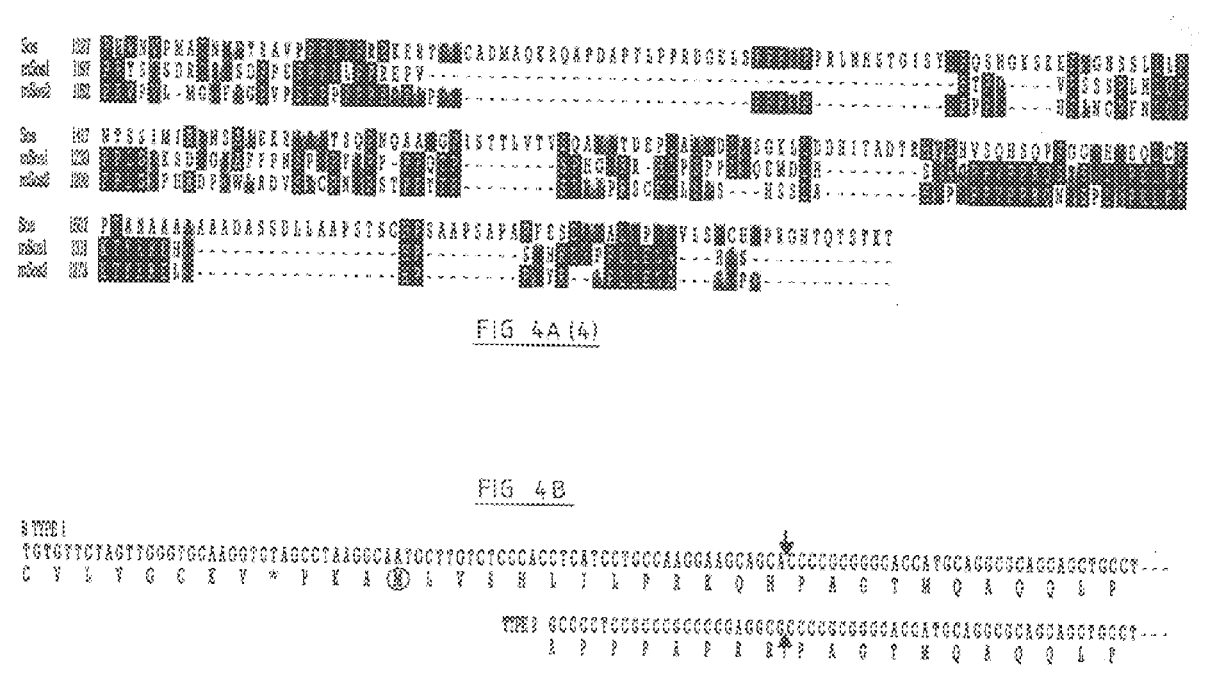

FIG. 4b: Alternate aminoterminal coding regions of the mSos1 gene (SEQ ID NOS:7 and 8) identified by 5' RACE (Frohman, M. A. and Martin, G. R., 1988). The sequence of the mSos1 gene was derived from a composite of cDNA clones and 5' RACE products. The majority of RACE products (type 2) (SEQ ID NO:8) terminated before reaching a potential initiating methionine in a highly GC region that could not be processed by reverse transcriptase. An alternate RACE product was identified (type 1) (SEQ ID NO:7) which diverged from this sequence as indicated and extended to a potential methionine initiation codon and upstream stop codon. The molecular weight of the predicted protein is 150 kd;

FIG. 5a: Alignment of the predicted Drosophila (SEQ ID NO:9) and mouse Sos proteins (SEQ ID NOS:10 and 11) with four related yeast proteins cdc25 (SEQ ID NO:12), sdc25 (SEQ ID NO:13), ste6 (SEQ ID NO:14) and bud5 (SEQ ID NO:15).

Figures 5, 5A:
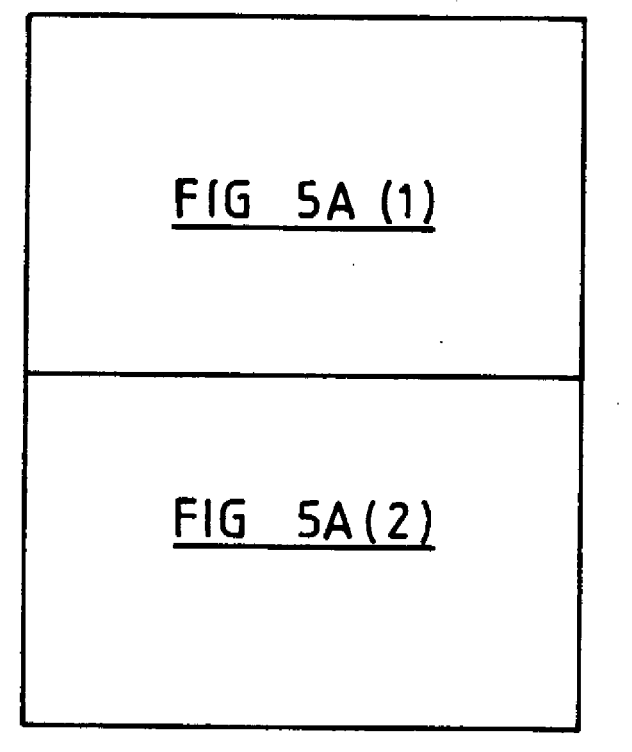
Figure 5A:
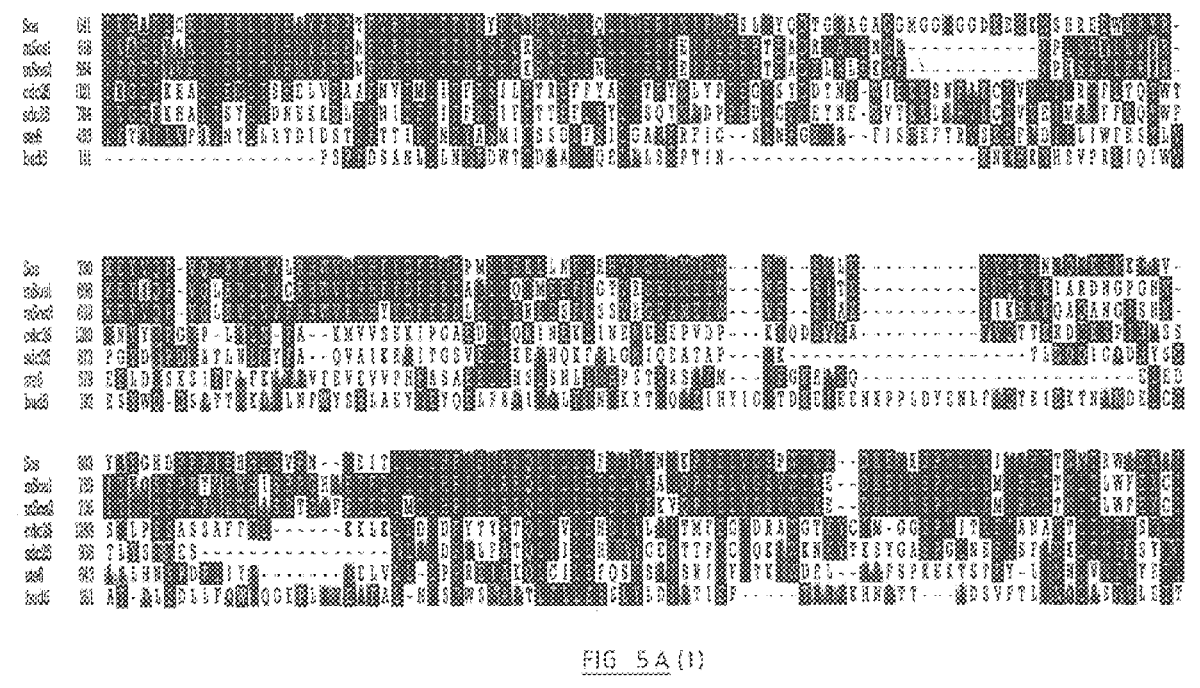
Figure 5B:
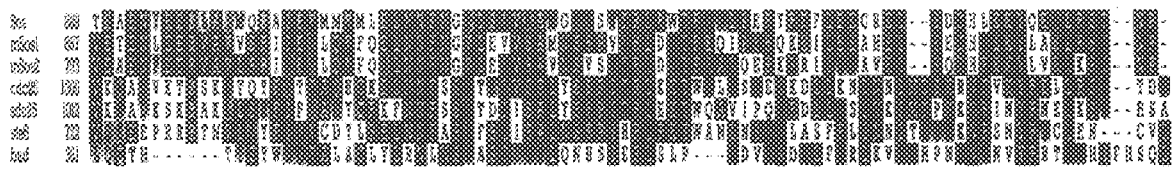

FIG. 5b: Schematic representation showing the size of each protein and the relative position of the conserved domain shown in (a) within each protein. Percentages indicate the degree of amino acid identity between a given domain and cdc25; and FIG. 6: Northern blot analysis of RNA derived from a range of (a) mouse embryonic and adult tissues and (b) continuous mouse and human cell lines. Transcripts of 5.4 kb and 8.4 kb were detected with an mSos1 probe in all tissues and cell lines tested. Variation in signal intensity was mainly due to differences in the amount and quality of RNA (see control CAODH probe). Additional smaller transcripts were apparent in testes RNA. A single major transcript of 5.6 kb was detected with an mSos2 probe, expressed at apparently comparable levels of mSos1. Adult tissues are indicated. Embryonic tissues were from heads and bodies of embryos whose stage of gestation was estimated from the time of plugging of the donor females. Mouse cell lines are, 3T3, Balb/c fibroblast; FN4, erythroid; FDCP1, myeloid; J774, macrophage; ABLS8, preB lymphoid, W279, B lymphoid, MPC11, plasmacytoma; EL4, early T lymphoid and W7.1, T lymphoid. Transcripts of the same size were also detected in RNA from the human erythroleukaemic cell line K562. GAPDH was used as a control probe for the amount and quality of RNA.

EXAMPLE 1

A fragment of the Drosophila Sos gene (corresponding to amino acids 841–1303, Simon et al., Supra) was used to screen mouse embryonic eye and adult brain cDNA libraries at low stringency.

cDNA clones were isolated from random bred Swiss E17 embryonic eye and Balb/c adult brain (Stratagene) cDNA libraries using a random Sos cDNA fragment. Duplicate nitrocellulose filters were hybridized in 5×SSC, 5×Denharts, 5 mM EDTA, 100 µg/ml herring testes DNA, 0.1% SDS at 65° C. for 18 hr and washed in 2×SSC, 0.1% SDS at 50° C. Partial DNA sequence obtained from two clones confirmed the isolation of two Sos related genes termed mSos1 and mSos2. Subsequent screening of the eye and brain libraries with these cDNA inserts identified the remainder of the clones, present at approximately 1;150,000 (eye) and 1;250,000 (brain) recombinants. S5' RACE of mSos1 was performed using RNA derived from an adult mouse brain as described previously (Frohman and Martin, 1988) and also with the modifications of using thermostable reverse transcriptase Tet-Z, Amersham) and prior denaturation of RNA with methyl mercury (Sambrook et al, 1989). Double stranded dideoxy chain termination DNA sequencing was performed on either nested deletions of cDNA cloned in Bluescript KS or with specific oligonucleotide primers using standard methods (Sambrook et al., Supra). The sequence of both strands was obtained and nucleotide sequence of mSos 1 and 2 is shown in FIGS. 1 and 2, (SEQ ID NOS:1 and 3, respectively).

FIG. 3 shows alignment of sequences of partial sequences of mSos 1 and mSos 2 to maximise homology. The nucleotide numbering of FIG. 3 differs from FIGS. 1 and 2, as in FIGS. 1 and 2 the protein sequence starts at position 18, that is, the second methionine residue.

FIG. 4 shows the amino acid sequence of Drosophila (Sos) and mouse Sos (mSos) proteins. The sequence is presented using the standard one letter amino acid code The molecular weight of the predicted protein is about 150 kd The correct amino acid sequence numbering is shown in FIGS. 1 and 2 with the second methinone residue in mSos representing the start of translation.

The predicted amino acid sequence for mSos2 (SEQ ID NO:4) extended to within 85 amino acids of the aminoterminal end of Sos (FIG. 4a). Sos shows an overall amino acid identity to both mSos1 and mSos2 of 45%. Both mSos1 and mSos2 remain colinear with SoS over their coding regions, with the exception of their carboxyterminal ends where homology between Sos and the murine genes is more scattered. Comparison of the two murine genes shows that they share approximately 67 amino acid identity, with the lowest degree of similarity residing in the final 270 amino acids (41% identity, FIG. 4a). No significant areas of homology were identified when the untranslated regions of the two genes were compared.

Figure 5B:
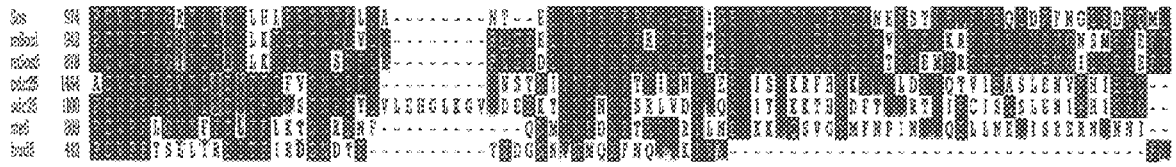
Figure 5B:
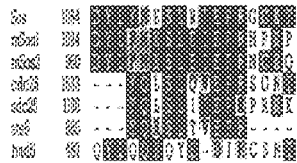

FIG. 5 shows alignment of the predicted Drosophila and mouse Sos proteins with four related yeast proteins cdc25, sdc25, ste6 and bud5.

The most notable feature of the Sos and mSos genes is a central domain of approximately 430 amino acids which shows a high degree of homology to several yeast guanine nucleotide exchange factors, including cdc25, sdc25 and ste6. This domain is present in a fragment of the sdc25 gene which is capable of catalysing nucleotide exchange by either the yeast RAS2 protein or human c-ras (Crechet at al., 1990), suggesting that the region of homology between the yeast, Drosophila and mouse genes defines a domain that catalyses nucleotide exchange on ras proteins. Inclusion of the mSos1 and mSos2 in this alignment further highlights residues which are highly conserved between the members of this gene family (FIG. 3a). Similarity between Sos and Sos and the yeast genes is limited to this domain.

We have also identified a second domain on both the mSos 1 (amino adds 200 to 500 of FIG. 1) and mSos 2 predicted polypeptides which has homology with the dbl protein, which is a guanine exchange factor for a ras-related protein. This suggests that mSos proteins may have separate guanine exchange domains of ras and for ras related proteins.

EXAMPLE 2

RNA isolated from various murine development stages, adult tissues, haemopoietic cell lines, and a human cell line was analysed for Sos transcripts.

Polyadenylated RNA was isolated from tissues and cell lines by disruption in proteinase K and SDS (Gonda, 1985) and oligo-(dT) affinity chromatography. Two micrograms of RNA from each source was subjected to formaldehyde agarose gel electrophoresis (Sambrook et al, Supra), transferred overnight to Hybond C-super (Amersham) in 20×SSC and then baked for 2 hrs. Filters were prehybridized from 4–6 h in 50% formamide, 5×SSC, 5×Denhardts, 5 mM EDTA, 100 µg ml-1 herring tests DNA and 0.5% SDS at 42° C. and then hybridized for 18 h. The 32P labelled probes were from nt299 to 4464 of mSos1 and from nt1 to 3801 of the available mSos2 sequence. Identical results were obtained with non-overlapping probes from the 3' untranslated region of each gene (data not shown). Washes were performed in 0.2×SSC, 0.3% SDS at 65° C. and the filter autoradiographed for 3 days at −70° C. in the presence of an intensifying screen.

Figure 6A:
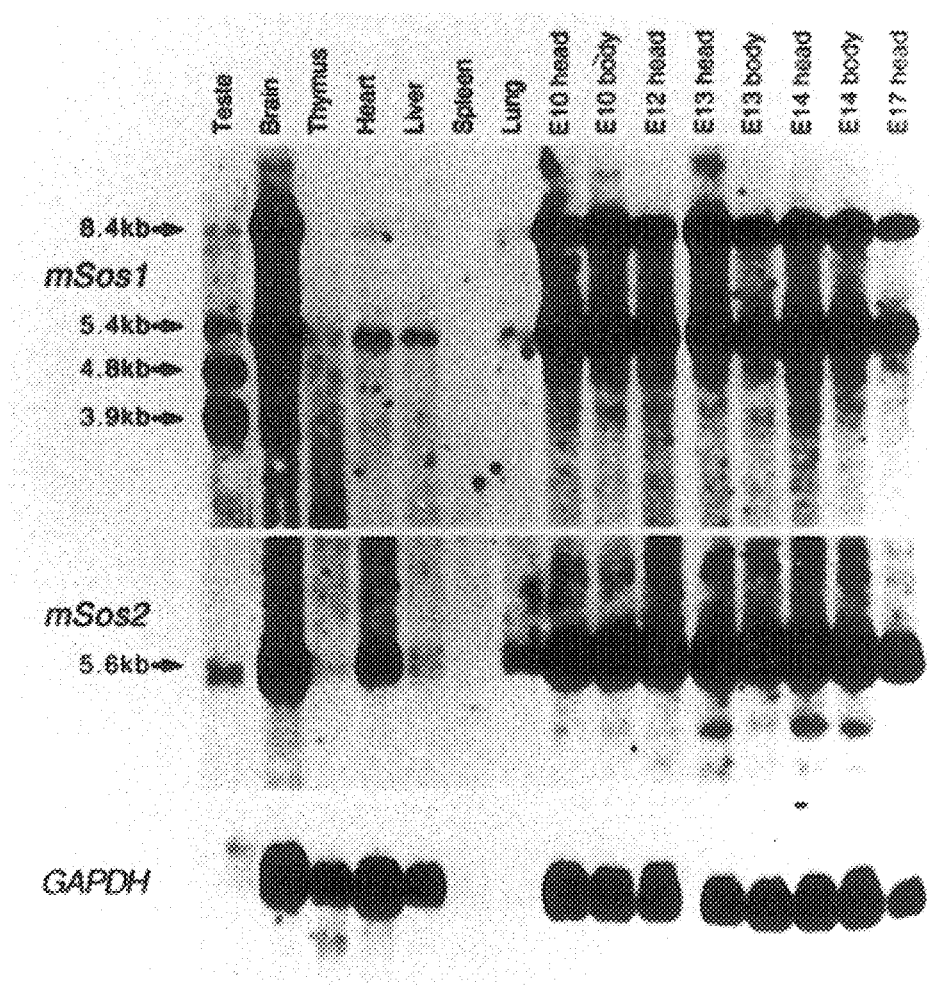
Figure 6B:
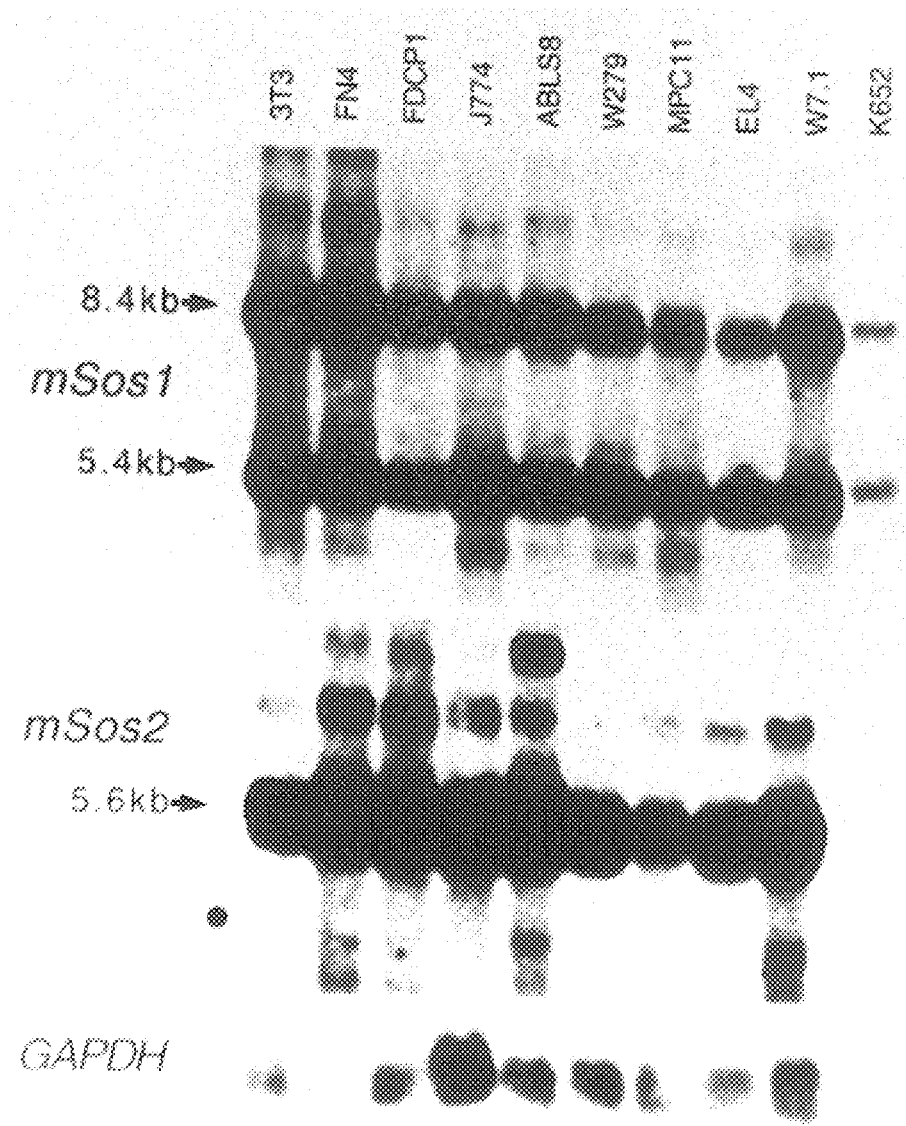

As shown in FIG. 6, the mSos1 gene encodes two distinct transcripts of 5.4 kb and 8.4 kb that are present in approximately equal abundance. Additional smaller transcripts of 4.8 kb and 3.9 kb were detected in RNA derived from testes (FIG. 6a). The mSos2 gene appears to encode a single transcript of 5.6 kb. As a cDNA of 5.3 kb has been obtained for mSos2 this suggests that the majority of the coding region has been obtained for this gene. To investigate whether there was any lineage restriction in expression of either gene within a given tissue, we tested RNA expression in haemopoietic cell lines that were representative of early and late lymphoid, myeloid and erythroid lineages. Expression of both mSos1 and mSos2 was detected in all haemopoietic lineages tested and was comparable to that in Balb/c 3T3 fibroblats (FIG. 6b). The broad pattern of expression obtained with mSos1 and mSos2 is consistent with a postulated role in regulating the widely expressed ras proteins.

Northern and Southern blot analysis was also performed using human RNA and DNA. Transcripts corresponding in size to those from mSos1 and mSos2 were present in RNA from the human erythroleukaemic cell line K562 (Lozzio and Lozzio, 1975) (FIG. 6b) and mSos1 and mSos2 hybridized with human genomic DNA when probed at high stringency (data not shown), indicating the presence of separate human genes closely related to both mSos1 and mSos2, which may be regarded as the human mSos genes.

This invention has been described by way of Example only, and includes all modifications, variations, nucleotide sequences and fragments/analogues thereof, and protein sequences and fragments and analogues thereof as herein described. Human Sos genes and polypeptides, as well as fragments and analogues thereof, may be isolated and characterised according to these Examples.

REFERENCES

Cantley, L. C., et al. (1991) Cell 64, 281–302.
Crechet, J., et al. (1990) Science 248, 866–868.
Cross, M., and Dexter, T. M. (1991) Cell 64, 271–280.
Frohman, M. A., and Martin, G. R (1988) Proc. Natl. Acad. Sci. 85, 8998–9002.
Gonda, T. J., et al. (1985) Embo J. 4, 2003–2008.
Lozzio, C. B., and Lozzio, B. B. (1975) Blood 45, 321–334.
Sambrook, J. et al. (1989) Molecular Cloning, Cold Spring Harbor Laboratory, New York.

I claim:

1. An isolated DNA molecule comprising a nucleotide sequence encoding murine son of sevenless gene 1 (mSOS1) polypeptide having the amino acid sequence of SEQ ID NO:2, or a fragment of at least 20 nucleotides of said DNA molecule.

2. The isolated DNA molecule of claim 1, wherein said nucleotide sequence encoding mSOS1 has the nucleotide sequence shown in SEQ ID NO:1.

3. An isolated DNA molecule comprising a nucleotide sequence encoding murine son of sevenless gene 2 (mSOS2) polypeptide having the amino acid sequence of SEQ ID NO:4, or a fragment of at least 20 nucleotides of said DNA molecule.

4. The isolated DNA molecule of claim 3, wherein said nucleotide sequence encoding mSOS2 has the nucleotide sequence shown in SEQ ID NO:3.

5. A vector comprising the isolated DNA molecule of any of claims 1, 3, 2 or 4.

6. An isolated mSOS1 polypeptide having the amino acid sequence shown in SEQ ID NO:2, or a fragment of at least 20 amino acids thereof.

7. An isolated mSOS2 polypeptide having the amino acid sequence shown in SEQ ID NO:4, or a fragment of at least 20 amino acids thereof.

8. A method for detecting a mutant mSOS1 gene comprising the steps of:

(A) obtaining DNA encoding mSOS1 protein from a test subject;

(B) determining:
  (i) the nucleotide sequence, and optionally the encoded amino acid sequence, of the resulting DNA obtained in step (A), or
  (ii) the chromosomal location of the resulting DNA obtained in step (A), or
  (iii) the structure of the resulting DNA obtained in step (A);

(C) comparing the resulting nucleotide sequence or chromosomal location or structure obtained in step (B) with the nucleotide sequence, chromosomal location or structure of wild-type mSOS1 gene, wherein the nucleotide sequence of wild-type mSOS1 gene is that shown in SEQ ID NO:1, or comparing the resulting encoded amino acid sequence with the amino acid sequence of wild-type mSOS1 protein, wherein the amino acid sequence of wild-type mSOS1 protein is that shown in SEQ ID NO:2, wherein a mutant mSOS1 gene is detected when the resulting nucleotide sequence, chromosomal location or structure obtained in step (B) differs from that of SEQ ID NO:1, or when the resulting encoded amino acid sequence obtained in step (B) differs from that of SEQ ID NO:2.

9. The method according to claim 8, wherein the structure in step (B) is determined by carrying out restriction fragment polymorphism analysis or analysis of amplified products.

10. A method for detecting a mutant mSOS2 gene comprising the steps of:

(A) obtaining DNA encoding mSOS2 protein from a test subject;

(B) determining:
  (i) the nucleotide sequence, and optionally the encoded amino acid sequence, of the resulting DNA obtained in step (A), or
  (ii) the chromosomal location of the resulting DNA obtained in step (A), or
  (iii) the structure of the resulting DNA obtained in step (A);
(C) comparing the resulting nucleotide sequence or chromosomal location or structure obtained in step (B) with the nucleotide sequence, chromosomal location or structure of wild-type mSOS1 gene, wherein the nucleotide sequence of wild-type mSOS2 gene is that shown in SEQ ID NO:3, or comparing the resulting encoded amino acid sequence with the amino acid sequence of wild-type mSOS2 protein, wherein the amino acid sequence of wild-type mSOS1 protein is that shown in SEQ ID NO:4, wherein a mutant mSOS2 gene is detected when the resulting nucleotide sequence, chromosomal location or structure obtained in step (B) differs from that of SEQ ID NO:3, or when the resulting encoded amino acid sequence obtained in step (B) differs from that of SEQ ID NO:4.

11. The method according to claim 10, wherein the structure in step (B) is determined by carrying out restriction fragment polymorphism analysis or analysis of amplified products.

12. A method for detecting a mutant mSOS1 protein comprising the steps of:
(A) obtaining mSOS1 protein from a test subject;
(B) determining the amino acid sequence of the resulting mSOS1 protein obtained in step (A);
(c) comparing the resulting amino acid sequence obtained in step (B) with the amino acid sequence of wild-type mSOS1 protein, wherein the amino acid sequence of wild-type mSOS1 protein is that shown in SEQ ID NO:2, wherein a mutant mSOS1 protein is detected when the resulting amino acid sequence obtained in step (B) differs from that of SEQ ID NO: 2.

13. A method for detecting a mutant mSOS2 protein comprising the steps of:
(A) obtaining mSOS2 protein from a test subject;
(B) determining the amino acid sequence of the resulting mSOS2 protein obtained in step (A);
(C) comparing the resulting amino acid sequence obtained in step (B) with the amino acid sequence of wild-type mSOS2 protein, wherein the amino acid sequence of wild-type mSOS2 protein is that shown in SEQ ID NO:4, wherein a mutant mSOS2 protein is detected when the resulting amino acid sequence obtained in step (B) differs from that of SEQ ID NO:4.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 4716 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 22..3975

( x i ) SEQUENCE DESCRIPTION: SEQ ID NO:1:

```
AAGCAGCACC  CCGCGGGCAC  C  ATG  CAG  GCG  CAG  CAG  CTG  CCT  TAC  GAG  TTT         51
                           Met  Gln  Ala  Gln  Gln  Leu  Pro  Tyr  Glu  Phe
                            1                  5                          10

TTC  AGC  GAG  GAG  AAC  GCG  CCC  AAG  TGG  CGG  GGG  CTG  CTG  GTG  CCT  GCG      99
Phe  Ser  Glu  Glu  Asn  Ala  Pro  Lys  Trp  Arg  Gly  Leu  Leu  Val  Pro  Ala
                    15                      20                      25

CTG  AAA  AAG  GTT  CAG  GGG  CAA  GTT  CAC  CCT  ACT  CTT  GAG  TCT  AAT  GAT     147
Leu  Lys  Lys  Val  Gln  Gly  Gln  Val  His  Pro  Thr  Leu  Glu  Ser  Asn  Asp
               30                      35                      40

GAT  GCT  CTT  CAG  TAT  GTT  GAA  GAA  TTA  ATT  TTG  CAA  TTA  CTA  AAT  ATG     195
Asp  Ala  Leu  Gln  Tyr  Val  Glu  Glu  Leu  Ile  Leu  Gln  Leu  Leu  Asn  Met
          45                      50                      55

CTA  TGC  CAA  GCT  CAG  CCC  CGG  AGT  GCT  TCA  GAT  GTG  GAG  GAA  CGT  GTT     243
Leu  Cys  Gln  Ala  Gln  Pro  Arg  Ser  Ala  Ser  Asp  Val  Glu  Glu  Arg  Val
     60                      65                      70

CAA  AAG  AGT  TTT  CCT  CAT  CCA  ATT  GAT  AAG  TGG  GCA  ATA  GCT  GAT  GCC     291
Gln  Lys  Ser  Phe  Pro  His  Pro  Ile  Asp  Lys  Trp  Ala  Ile  Ala  Asp  Ala
75                       80                      85                      90
```

```
CAA TCA GCC ATT GAA AAG AGG AAG AGA CGA AAT CCT TTA TCG CTG CCA    339
Gln Ser Ala Ile Glu Lys Arg Lys Arg Arg Asn Pro Leu Ser Leu Pro
            95                  100                 105

GCA GAA AGA ATT CAT CAT TTA TTA AGG GAG GTC CTC GGT TAT AAA ATT    387
Ala Glu Arg Ile His His Leu Leu Arg Glu Val Leu Gly Tyr Lys Ile
        110                 115                 120

GAC CAC CAG GTT TCT GTT TAC ATA GTA GCA GTA TTA GAA TAC ATT TCT    435
Asp His Gln Val Ser Val Tyr Ile Val Ala Val Leu Glu Tyr Ile Ser
            125                 130                 135

GCA GAT ATT TTA AAG CTC GTG GGG AAT TAT GTA AGA AAT ATA CGG CAT    483
Ala Asp Ile Leu Lys Leu Val Gly Asn Tyr Val Arg Asn Ile Arg His
    140                 145                 150

TAT GAA ATT ACA AAA CAA GAC ATT AAA GTG GCA ATG TGT GCT GAT AAG    531
Tyr Glu Ile Thr Lys Gln Asp Ile Lys Val Ala Met Cys Ala Asp Lys
155                 160                 165                 170

GTA TTG ATG GAT ATG TTT CAT CAA GAT GTA GAA GAT ATA AAT ATC TTA    579
Val Leu Met Asp Met Phe His Gln Asp Val Glu Asp Ile Asn Ile Leu
                175                 180                 185

TCT TTA ACT GAT GAA GAG CCT TCC ACC TCA GGA GAA CAA ACT TAT TAT    627
Ser Leu Thr Asp Glu Glu Pro Ser Thr Ser Gly Glu Gln Thr Tyr Tyr
            190                 195                 200

GAT TTG GTA AAA GCA TTC ATG GCA GAA ATT CGA CAG TAT ATA AGA GAA    675
Asp Leu Val Lys Ala Phe Met Ala Glu Ile Arg Gln Tyr Ile Arg Glu
        205                 210                 215

TTA AAT CTA ATT ATA AAA GTT TTT CGA GAG CCC TTT GTC TCT AAT TCC    723
Leu Asn Leu Ile Ile Lys Val Phe Arg Glu Pro Phe Val Ser Asn Ser
    220                 225                 230

AAA TTG TTT TCA TCT AAT GAT GTA GAA AAC ATA TTC AGT CGT ATA GTA    771
Lys Leu Phe Ser Ser Asn Asp Val Glu Asn Ile Phe Ser Arg Ile Val
235                 240                 245                 250

GAT ATA CAT GAA CTT AGT GTA AAG TTA CTG GGC CAT ATA GAA GAT ACT    819
Asp Ile His Glu Leu Ser Val Lys Leu Leu Gly His Ile Glu Asp Thr
                255                 260                 265

GTA GAA ATG ACA GAT GAA GGC AGT CCC CAC CCA TTA GTA GGA AGC TGT    867
Val Glu Met Thr Asp Glu Gly Ser Pro His Pro Leu Val Gly Ser Cys
            270                 275                 280

TTT GAA GAC TTA GCA GAA GAA CTG GCA TTT GAC CCG TAT GAG TCA TAT    915
Phe Glu Asp Leu Ala Glu Glu Leu Ala Phe Asp Pro Tyr Glu Ser Tyr
        285                 290                 295

GCT CGG GAT ATT TTA CGA CCC GGA TTC CAT GGC CAT TTT CTT AGT CAG    963
Ala Arg Asp Ile Leu Arg Pro Gly Phe His Gly His Phe Leu Ser Gln
    300                 305                 310

TTA TCA AAG CCT GGG GCA GCA CTT TAT TTG CAG TCC ATA GGC GAA GGC    1011
Leu Ser Lys Pro Gly Ala Ala Leu Tyr Leu Gln Ser Ile Gly Glu Gly
315                 320                 325                 330

TTC AAA GAA GCT GTC CAG TAC GTC CTG CCC CGG CTG CTG CTT GCC CCT    1059
Phe Lys Glu Ala Val Gln Tyr Val Leu Pro Arg Leu Leu Leu Ala Pro
                335                 340                 345

GTG TAC CAC TGT CTG CAT TAC TTT GAA CTT CTG AAG CAG TTA GAA GAA    1107
Val Tyr His Cys Leu His Tyr Phe Glu Leu Leu Lys Gln Leu Glu Glu
            350                 355                 360

AAG AGT GAA GAT CAA GAA GAC AAG GAG TGT ATG AAG CAA GCA ATA ACA    1155
Lys Ser Glu Asp Gln Glu Asp Lys Glu Cys Met Lys Gln Ala Ile Thr
        365                 370                 375

GCC CTG CTT AAT GTC CAA AGT GGC ATG GAA AAA ATT TGC TCC AAA AGT    1203
Ala Leu Leu Asn Val Gln Ser Gly Met Glu Lys Ile Cys Ser Lys Ser
    380                 385                 390

CTT GCA AAA CGA AGA CTA AGT GAG TCT GCA TGT CGG TTT TAC AGC CAG    1251
Leu Ala Lys Arg Arg Leu Ser Glu Ser Ala Cys Arg Phe Tyr Ser Gln
395                 400                 405                 410
```

```
CAG ATG AAG GGG AAA CAG CTA GCC ATC AAG AAG ATG AAC GAG ATC CAG       1299
Gln Met Lys Gly Lys Gln Leu Ala Ile Lys Lys Met Asn Glu Ile Gln
        415                 420                 425

AAG AAC ATT GAT GGC TGG GAG GGG AAG GAC ATT GGA CAG TGT TGC AAT       1347
Lys Asn Ile Asp Gly Trp Glu Gly Lys Asp Ile Gly Gln Cys Cys Asn
                430                 435                 440

GAG TTC ATA ATG GAA GGA ACT CTT ACA CGT GTA GGA GCC AAA CAC GAG       1395
Glu Phe Ile Met Glu Gly Thr Leu Thr Arg Val Gly Ala Lys His Glu
            445                 450                 455

AGA CAC ATA TTT CTC TTC GAT GGC TTA ATG ATT TGC TGT AAA TCA AAC       1443
Arg His Ile Phe Leu Phe Asp Gly Leu Met Ile Cys Cys Lys Ser Asn
        460                 465                 470

CAT GGG CAG CCA AGA CTC CCT GGT GCT AGC AGT GCA GAA TAC CGG CTT       1491
His Gly Gln Pro Arg Leu Pro Gly Ala Ser Ser Ala Glu Tyr Arg Leu
475                 480                 485                 490

AAA GAA AAG TTT TTT ATG CGA AAG GTA CAG ATT AAT GAT AAA GAT GAC       1539
Lys Glu Lys Phe Phe Met Arg Lys Val Gln Ile Asn Asp Lys Asp Asp
                495                 500                 505

ACC AGT GAG TAC AAG CAT GCT TTT GAA ATC ATT CTG AAA GAT GGC AAT       1587
Thr Ser Glu Tyr Lys His Ala Phe Glu Ile Ile Leu Lys Asp Gly Asn
            510                 515                 520

AGT GTT ATA TTT TCT GCC AAG TCA GCT GAA GAG AAA AAC AAC TGG ATG       1635
Ser Val Ile Phe Ser Ala Lys Ser Ala Glu Glu Lys Asn Asn Trp Met
        525                 530                 535

GCA GCA CTG ATC TCT TTG CAG TAC CGC AGC ACC CTG GAG AGG ATG CTG       1683
Ala Ala Leu Ile Ser Leu Gln Tyr Arg Ser Thr Leu Glu Arg Met Leu
540                 545                 550

GAC GTA ACG GTG CTG CAG GAG GAG AAG GAG GAG CAG ATG AGG CTG CCC       1731
Asp Val Thr Val Leu Gln Glu Glu Lys Glu Glu Gln Met Arg Leu Pro
555                 560                 565                 570

AGT GCT GAA GTG TAC AGG TTT GCA GAA CCT GAC TCC GAG GAG AAT ATT       1779
Ser Ala Glu Val Tyr Arg Phe Ala Glu Pro Asp Ser Glu Glu Asn Ile
                575                 580                 585

CTA TTC GAA GAG AAT GTG CAG CCC AAA GCT GGG ATC CCC ATT ATC AAG       1827
Leu Phe Glu Glu Asn Val Gln Pro Lys Ala Gly Ile Pro Ile Ile Lys
            590                 595                 600

GCA GGG ACA GTG CTT AAG CTC ATT GAG AGG CTT ACC TAC CAC ATG TAC       1875
Ala Gly Thr Val Leu Lys Leu Ile Glu Arg Leu Thr Tyr His Met Tyr
        605                 610                 615

GCA GAT CCA AAT TTT GTT CGG ACG TTT CTT ACA ACA TAC AGG TCC TTT       1923
Ala Asp Pro Asn Phe Val Arg Thr Phe Leu Thr Thr Tyr Arg Ser Phe
620                 625                 630

TGC AGA CCT CAA GAA CTA CTG AGT CTT CTG ATA GAA AGA TTT GAA ATT       1971
Cys Arg Pro Gln Glu Leu Leu Ser Leu Leu Ile Glu Arg Phe Glu Ile
635                 640                 645                 650

CCA GAG CCT GAG CCA ACA GAA GCT GAT CGC ATA GCT ATA GAG AAT GGA       2019
Pro Glu Pro Glu Pro Thr Glu Ala Asp Arg Ile Ala Ile Glu Asn Gly
                655                 660                 665

GAT CAG CCC CTG AGT GCA GAG CTG AAG AGG TTT AGA AAG GAA TAT ATT       2067
Asp Gln Pro Leu Ser Ala Glu Leu Lys Arg Phe Arg Lys Glu Tyr Ile
            670                 675                 680

CAG CCT GTG CAG TTG AGG GTG TTA AAT GTG TGT CGG CAC TGG GTG GAG       2115
Gln Pro Val Gln Leu Arg Val Leu Asn Val Cys Arg His Trp Val Glu
        685                 690                 695

CAC CAT TTC TAT GAC TTT GAA AGA GAT GCA GAC TTA TTA CAG AGA ATG       2163
His His Phe Tyr Asp Phe Glu Arg Asp Ala Asp Leu Leu Gln Arg Met
700                 705                 710

GAG GAA TTT ATT GGA ACA GTA AGA GGT AAA GCA ATG AAA AAA TGG GTC       2211
Glu Glu Phe Ile Gly Thr Val Arg Gly Lys Ala Met Lys Lys Trp Val
715                 720                 725                 730
```

| | | | | | | | | | | | | | | | | |
|---|---|---|---|---|---|---|---|---|---|---|---|---|---|---|---|---|
| GAA | TCC | ATC | ACT | AAG | ATA | ATC | CAA | AGG | AAA | AAA | ATT | GCA | AGA | GAC | AAT | 2259 |
| Glu | Ser | Ile | Thr 735 | Lys | Ile | Ile | Gln | Arg 740 | Lys | Lys | Ile | Ala | Arg | Asp 745 | Asn | |
| GGC | CCA | GGT | CAT | AAC | ATT | ACA | TTT | CAG | AGC | TCA | CCT | CCC | ACA | GTT | GAG | 2307 |
| Gly | Pro | Gly | His 750 | Asn | Ile | Thr | Phe | Gln 755 | Ser | Ser | Pro | Pro | Thr 760 | Val | Glu | |
| TGG | CAC | ATA | AGC | AGA | CCT | GGG | CAC | ATA | GAG | ACT | TTT | GAC | TTG | CTC | ACC | 2355 |
| Trp | His | Ile 765 | Ser | Arg | Pro | Gly | His | Ile 770 | Glu | Thr | Phe | Asp 775 | Leu | Leu | Thr | |
| TTA | CAC | CCA | ATA | GAA | ATT | GCT | CGG | CAA | CTC | ACT | TTA | CTT | GAA | TCA | GAT | 2403 |
| Leu | His | Pro 780 | Ile | Glu | Ile | Ala | Arg 785 | Gln | Leu | Thr | Leu | Leu 790 | Glu | Ser | Asp | |
| CTA | TAC | CGG | GCT | GTG | CAG | CCA | TCA | GAA | TTA | GTT | GGA | AGT | GTG | TGG | ACA | 2451 |
| Leu 795 | Tyr | Arg | Ala | Val | Gln 800 | Pro | Ser | Glu | Leu | Val 805 | Gly | Ser | Val | Trp | Thr 810 | |
| AAA | GAA | GAT | AAA | GAA | ATT | AAT | TCT | CCC | AAC | CTT | CTG | AAG | ATG | ATT | CGG | 2499 |
| Lys | Glu | Asp | Lys | Glu 815 | Ile | Asn | Ser | Pro | Asn 820 | Leu | Leu | Lys | Met | Ile 825 | Arg | |
| CAC | ACC | ACT | AAC | CTC | ACT | TTG | TGG | TTT | GAG | AAA | TGT | ATT | GTA | GAA | ACA | 2547 |
| His | Thr | Thr | Asn 830 | Leu | Thr | Leu | Trp | Phe 835 | Glu | Lys | Cys | Ile | Val 840 | Glu | Thr | |
| GAA | AAC | TTA | GAA | GAA | AGA | GTA | GCT | GTA | GTA | AGT | CGG | ATA | ATT | GAG | ATT | 2595 |
| Glu | Asn | Leu 845 | Glu | Glu | Arg | Val | Ala 850 | Val | Val | Ser | Arg | Ile 855 | Ile | Glu | Ile | |
| CTA | CAA | GTC | TTT | CAA | GAG | CTG | AAC | AAC | TTC | AAT | GGT | GTC | CTG | GAA | GTT | 2643 |
| Leu | Gln 860 | Val | Phe | Gln | Glu | Leu 865 | Asn | Asn | Phe | Asn | Gly 870 | Val | Leu | Glu | Val | |
| GTC | AGT | GCT | ATG | AAC | TCG | TCA | CCT | GTT | TAC | AGA | CTA | GAC | CAC | ACA | TTT | 2691 |
| Val 875 | Ser | Ala | Met | Asn 880 | Ser | Ser | Pro | Val | Tyr 885 | Arg | Leu | Asp | His | Thr 890 | Phe | |
| GAG | CAA | ATA | CCA | AGC | AGA | CAA | AAG | AAA | ATT | TTA | GAA | GAA | GCT | CAT | GAA | 2739 |
| Glu | Gln | Ile | Pro | Ser 895 | Arg | Gln | Lys | Lys | Ile 900 | Leu | Glu | Glu | Ala | His 905 | Glu | |
| TTG | AGT | GAA | GAT | CAC | TAT | AAG | AAA | TAT | TTG | GCA | AAA | CTC | AGG | TCT | ATT | 2787 |
| Leu | Ser | Glu | Asp 910 | His | Tyr | Lys | Lys | Tyr 915 | Leu | Ala | Lys | Leu | Arg 920 | Ser | Ile | |
| AAT | CCA | CCG | TGT | GTG | CCT | TTC | TTT | GGA | ATT | TAT | CTC | ACA | AAT | ATC | CTG | 2835 |
| Asn | Pro | Pro 925 | Cys | Val | Pro | Phe | Phe 930 | Gly | Ile | Tyr | Leu | Thr 935 | Asn | Ile | Leu | |
| AAG | ACA | GAA | GAG | GGC | AAC | CCT | GAG | GTC | CTG | AGG | AGA | CAC | GGG | AAA | GAG | 2883 |
| Lys | Thr | Glu 940 | Glu | Gly | Asn | Pro | Glu 945 | Val | Leu | Arg | Arg | His 950 | Gly | Lys | Glu | |
| CTT | ATT | AAC | TTC | AGC | AAG | AGG | AGG | AGA | GTG | GCC | GAG | ATC | ACA | GGC | GAG | 2931 |
| Leu 955 | Ile | Asn | Phe | Ser | Lys 960 | Arg | Arg | Arg | Val | Ala 965 | Glu | Ile | Thr | Gly | Glu 970 | |
| ATC | CAG | CAG | TAC | CAG | AAC | CAG | CCC | TAC | TGC | TTA | CGG | GTG | GAG | CCG | GAC | 2979 |
| Ile | Gln | Gln | Tyr | Gln 975 | Asn | Gln | Pro | Tyr | Cys 980 | Leu | Arg | Val | Glu | Pro 985 | Asp | |
| ATC | AAG | AGG | TTC | TTT | GAA | AAC | TTG | AAT | CCA | ATG | GGA | AAC | AGC | ATG | GAG | 3027 |
| Ile | Lys | Arg | Phe 990 | Phe | Glu | Asn | Leu | Asn 995 | Pro | Met | Gly | Asn | Ser 1000 | Met | Glu | |
| AAA | GAA | TTT | ACA | GAC | TAT | CTG | TTC | AAC | AAA | TCC | CTA | GAA | ATA | GAA | CCC | 3075 |
| Lys | Glu | Phe | Thr 1005 | Asp | Tyr | Leu | Phe | Asn 1010 | Lys | Ser | Leu | Glu | Ile 1015 | Glu | Pro | |
| CGG | CAC | CCT | AAG | CCT | CTT | CCG | AGA | TTC | CCA | AAA | AAA | TAC | AGC | TAT | CCC | 3123 |
| Arg | His | Pro 1020 | Lys | Pro | Leu | Pro | Arg 1025 | Phe | Pro | Lys | Lys | Tyr 1030 | Ser | Tyr | Pro | |
| CTA | AAA | TCT | CCT | GGT | GTT | CGT | CCA | TCA | AAT | CCA | AGA | CCA | GGA | ACC | ATG | 3171 |
| Leu 1035 | Lys | Ser | Pro | Gly | Val 1040 | Arg | Pro | Ser | Asn | Pro 1045 | Arg | Pro | Gly | Thr | Met 1050 | |

| | | | | | | | | | | | | | | | | |
|---|---|---|---|---|---|---|---|---|---|---|---|---|---|---|---|---|
| AGA | CAT | CCC | ACA | CCT | CTG | CAG | CAG | GAG | CCA | AGA | AAA | ATT | AGC | TAC | AGT | 3219 |
| Arg | His | Pro | Thr | Pro | Leu | Gln | Gln | Glu | Pro | Arg | Lys | Ile | Ser | Tyr | Ser | |
| | | | 1055 | | | | 1060 | | | | | | 1065 | | | |
| CGG | ATT | CCT | GAA | AGT | GAG | ACG | GAA | AGC | ACA | GCA | TCT | GCA | CCA | AAC | TCC | 3267 |
| Arg | Ile | Pro | Glu | Ser | Glu | Thr | Glu | Ser | Thr | Ala | Ser | Ala | Pro | Asn | Ser | |
| | | | 1070 | | | | 1075 | | | | | | 1080 | | | |
| CCT | CGG | ACC | CCA | CTG | ACG | CCG | CCC | CCT | GCA | TCT | GGC | ACC | TCC | AGC | AAC | 3315 |
| Pro | Arg | Thr | Pro | Leu | Thr | Pro | Pro | Pro | Ala | Ser | Gly | Thr | Ser | Ser | Asn | |
| | | | 1085 | | | | 1090 | | | | | | 1095 | | | |
| ACA | GAT | GTT | TGC | AGC | GTG | TTC | GAT | TCT | GAC | CAC | TCG | GCA | AGC | CCT | TTT | 3363 |
| Thr | Asp | Val | Cys | Ser | Val | Phe | Asp | Ser | Asp | His | Ser | Ala | Ser | Pro | Phe | |
| | | | 1100 | | | | 1105 | | | | | | 1110 | | | |
| CAT | TCA | AGA | TCT | GCT | TCA | GTC | TCA | TCT | ATA | AGT | TTA | TCC | AAG | GGC | ACT | 3411 |
| His | Ser | Arg | Ser | Ala | Ser | Val | Ser | Ser | Ile | Ser | Leu | Ser | Lys | Gly | Thr | |
| 1115 | | | | 1120 | | | | 1125 | | | | | | 1130 | | |
| GAT | GAA | GTG | CCT | GTC | CCC | CCT | CCT | GTA | CCC | CCT | CGA | AGA | CGT | CCA | GAG | 3459 |
| Asp | Glu | Val | Pro | Val | Pro | Pro | Pro | Val | Pro | Pro | Arg | Arg | Arg | Pro | Glu | |
| | | | | 1135 | | | | 1140 | | | | | | 1145 | | |
| TCT | GCC | CCA | GCT | GAA | TCC | TCC | CCA | TCC | AAG | ATT | ATG | TCT | AAG | CAC | TTG | 3507 |
| Ser | Ala | Pro | Ala | Glu | Ser | Ser | Pro | Ser | Lys | Ile | Met | Ser | Lys | His | Leu | |
| | | | | 1150 | | | | 1155 | | | | | | 1160 | | |
| GAC | AGC | CCC | CCA | GCT | ATT | CCT | CCT | AGG | CAA | CCC | ACA | TCC | AAA | GCC | TAT | 3555 |
| Asp | Ser | Pro | Pro | Ala | Ile | Pro | Pro | Arg | Gln | Pro | Thr | Ser | Lys | Ala | Tyr | |
| | | | 1165 | | | | 1170 | | | | | | 1175 | | | |
| TCA | CCA | CGC | TAT | TCA | ATA | TCA | GAT | CGG | ACC | TCT | ATA | TCA | GAT | CCT | CCT | 3603 |
| Ser | Pro | Arg | Tyr | Ser | Ile | Ser | Asp | Arg | Thr | Ser | Ile | Ser | Asp | Pro | Pro | |
| | | | 1180 | | | | 1185 | | | | | | 1190 | | | |
| GAA | AGC | CCT | CCC | TTG | TTA | CCA | CCA | CGG | GAA | CCT | GTG | AGG | ACA | CCT | GAT | 3651 |
| Glu | Ser | Pro | Pro | Leu | Leu | Pro | Pro | Arg | Glu | Pro | Val | Arg | Thr | Pro | Asp | |
| 1195 | | | | 1200 | | | | | | | 1205 | | | | 1210 | |
| GTT | TTC | TCA | AGC | TCA | CCA | TTA | CAT | CTC | CAA | CCT | CCT | CCT | TTG | GGC | AAA | 3699 |
| Val | Phe | Ser | Ser | Ser | Pro | Leu | His | Leu | Gln | Pro | Pro | Pro | Leu | Gly | Lys | |
| | | | | 1215 | | | | 1220 | | | | | | 1225 | | |
| AAG | AGT | GAT | CAT | GGC | AAC | GCC | TTC | TTC | CCA | AAC | AGC | CCA | TCC | CCT | TTT | 3747 |
| Lys | Ser | Asp | His | Gly | Asn | Ala | Phe | Phe | Pro | Asn | Ser | Pro | Ser | Pro | Phe | |
| | | | 1230 | | | | 1235 | | | | | | 1240 | | | |
| ACA | CCG | CCA | CCC | CCC | CAA | ACC | CCC | TCT | CCT | CAT | GGC | ACG | AGA | AGG | CAT | 3795 |
| Thr | Pro | Pro | Pro | Pro | Gln | Thr | Pro | Ser | Pro | His | Gly | Thr | Arg | Arg | His | |
| | | | 1245 | | | | 1250 | | | | | | 1255 | | | |
| CTG | CCA | TCA | CCA | CCA | CTG | ACA | CAG | GAG | ATG | GAC | CTC | CAT | TCC | ATT | GCT | 3843 |
| Leu | Pro | Ser | Pro | Pro | Leu | Thr | Gln | Glu | Met | Asp | Leu | His | Ser | Ile | Ala | |
| | | | 1260 | | | | 1265 | | | | | | 1270 | | | |
| GGG | CCT | CCT | GTT | CCT | CCA | CGA | CAA | AGC | ACT | TCT | CAA | CTT | ATC | CCC | AAA | 3891 |
| Gly | Pro | Pro | Val | Pro | Pro | Arg | Gln | Ser | Thr | Ser | Gln | Leu | Ile | Pro | Lys | |
| 1275 | | | | 1280 | | | | | | | 1285 | | | | 1290 | |
| CTC | CCT | CCA | AAA | ACT | TAC | AAA | AGG | GAG | CAC | ACA | CAC | CCA | TCC | ATG | CAT | 3939 |
| Leu | Pro | Pro | Lys | Thr | Tyr | Lys | Arg | Glu | His | Thr | His | Pro | Ser | Met | His | |
| | | | 1295 | | | | 1300 | | | | | | 1305 | | | |
| AGA | GAT | GGA | CCA | CCA | CTG | CTG | GAG | AAT | GCC | CAT | TCT | TCC | TGA | GTT | CCT | 3987 |
| Arg | Asp | Gly | Pro | Pro | Leu | Leu | Glu | Asn | Ala | His | Ser | Ser | | | | |
| | | | 1310 | | | | 1315 | | | | | | | | | |
| CTA AGC TGG GAT AGT TTC CTA GCC CCC AGA TCC ATT GCT GGC AAT GGA | | | | | | | | | | | | | | | | 4035 |
| TGC ACT GAA CAT GCC AGC ACT GGG GAG TTC AAA TGAGAACTCC AAACACTAAC | | | | | | | | | | | | | | | | 4088 |
| GACTCTACTT CACGATGTAG TATAAGACAA TGAGTTTTAA CCTACATGGA ATTATGGAAT | | | | | | | | | | | | | | | | 4148 |
| AAAATGGTAT TCCAGCTTAG AATGTGGAAA CTGATTGCAC CTGGAAATCA CGTGAAGGGA | | | | | | | | | | | | | | | | 4208 |
| CTTTTCTGGC CATTGGGCAG AGTCCTCATA TTGTGAAGTG ATCTTTATCA TTAAAGGGAT | | | | | | | | | | | | | | | | 4268 |
| GGAAAACAGT CTAATGTCCA ACAAGCCCAT ATGTTGACAG TTTTTGTAAT TCAAAATATT | | | | | | | | | | | | | | | | 4328 |

```
ATGCACTTTT  AAAAAATCTT  AAACAGGGAT  CTCCTCCTTT  GTTTTCCTTT  GCTTTACTCT    4388

TCTACTTTAG  AATATTTTCG  TAAAAGTTAT  TCAGAGGACT  GTGAGAAAAG  GCTGTGGTAC    4448

CTGACCTTGT  TGAAATCAAG  GCCCAGCACT  GTACTACAGT  CCTGTTTACA  GATTATTACA    4508

GTGATCTGAA  TGGGTACCGA  GGCTTCACCA  AAAGAGGTAC  TTTTTGTTAT  TGTTATTGTT    4568

TAAGAATAAT  TATGCCAATT  TAAGAACATC  CCCTACCCAC  CCCCACTCAC  AAACAAAATG    4628

TGGTGGTGTT  GCCTTTAAAC  AAAAAATGTC  AATGTCATTA  ACATGATGGA  AGAAGAACAT    4688

TTTAAAACGT  AACTGTCAAG  TATCATTT                                          4716
```

( 2 ) INFORMATION FOR SEQ ID NO:2:

( i ) SEQUENCE CHARACTERISTICS:
        ( A ) LENGTH: 1319 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Gln  Ala  Gln  Gln  Leu  Pro  Tyr  Glu  Phe  Phe  Ser  Glu  Glu  Asn  Ala
 1                  5                        10                       15

Pro  Lys  Trp  Arg  Gly  Leu  Leu  Val  Pro  Ala  Leu  Lys  Lys  Val  Gln  Gly
                20                      25                       30

Gln  Val  His  Pro  Thr  Leu  Glu  Ser  Asn  Asp  Asp  Ala  Leu  Gln  Tyr  Val
           35                        40                       45

Glu  Glu  Leu  Ile  Leu  Gln  Leu  Leu  Asn  Met  Leu  Cys  Gln  Ala  Gln  Pro
      50                       55                       60

Arg  Ser  Ala  Ser  Asp  Val  Glu  Glu  Arg  Val  Gln  Lys  Ser  Phe  Pro  His
65                       70                       75                       80

Pro  Ile  Asp  Lys  Trp  Ala  Ile  Ala  Asp  Ala  Gln  Ser  Ala  Ile  Glu  Lys
                85                       90                       95

Arg  Lys  Arg  Arg  Asn  Pro  Leu  Ser  Leu  Pro  Ala  Glu  Arg  Ile  His  His
               100                      105                      110

Leu  Leu  Arg  Glu  Val  Leu  Gly  Tyr  Lys  Ile  Asp  His  Gln  Val  Ser  Val
          115                      120                      125

Tyr  Ile  Val  Ala  Val  Leu  Glu  Tyr  Ile  Ser  Ala  Asp  Ile  Leu  Lys  Leu
     130                      135                      140

Val  Gly  Asn  Tyr  Val  Arg  Asn  Ile  Arg  His  Tyr  Glu  Ile  Thr  Lys  Gln
145                      150                      155                      160

Asp  Ile  Lys  Val  Ala  Met  Cys  Ala  Asp  Lys  Val  Leu  Met  Asp  Met  Phe
               165                      170                      175

His  Gln  Asp  Val  Glu  Asp  Ile  Asn  Ile  Leu  Ser  Leu  Thr  Asp  Glu  Glu
          180                      185                      190

Pro  Ser  Thr  Ser  Gly  Glu  Gln  Thr  Tyr  Tyr  Asp  Leu  Val  Lys  Ala  Phe
     195                      200                      205

Met  Ala  Glu  Ile  Arg  Gln  Tyr  Ile  Arg  Glu  Leu  Asn  Leu  Ile  Ile  Lys
210                      215                      220

Val  Phe  Arg  Glu  Pro  Phe  Val  Ser  Asn  Ser  Lys  Leu  Phe  Ser  Ser  Asn
225                      230                      235                      240

Asp  Val  Glu  Asn  Ile  Phe  Ser  Arg  Ile  Val  Asp  Ile  His  Glu  Leu  Ser
               245                      250                      255

Val  Lys  Leu  Leu  Gly  His  Ile  Glu  Asp  Thr  Val  Glu  Met  Thr  Asp  Glu
          260                      265                      270

Gly  Ser  Pro  His  Pro  Leu  Val  Gly  Ser  Cys  Phe  Glu  Asp  Leu  Ala  Glu
     275                      280                      285
```

```
Glu  Leu  Ala  Phe  Asp  Pro  Tyr  Glu  Ser  Tyr  Ala  Arg  Asp  Ile  Leu  Arg
     290                 295                 300

Pro  Gly  Phe  His  Gly  His  Phe  Leu  Ser  Gln  Leu  Ser  Lys  Pro  Gly  Ala
305                      310                 315                      320

Ala  Leu  Tyr  Leu  Gln  Ser  Ile  Gly  Glu  Gly  Phe  Lys  Glu  Ala  Val  Gln
                    325                 330                           335

Tyr  Val  Leu  Pro  Arg  Leu  Leu  Leu  Ala  Pro  Val  Tyr  His  Cys  Leu  His
               340                 345                      350

Tyr  Phe  Glu  Leu  Leu  Lys  Gln  Leu  Glu  Glu  Lys  Ser  Glu  Asp  Gln  Glu
               355                 360                 365

Asp  Lys  Glu  Cys  Met  Lys  Gln  Ala  Ile  Thr  Ala  Leu  Leu  Asn  Val  Gln
     370                 375                      380

Ser  Gly  Met  Glu  Lys  Ile  Cys  Ser  Lys  Ser  Leu  Ala  Lys  Arg  Arg  Leu
385                      390                 395                           400

Ser  Glu  Ser  Ala  Cys  Arg  Phe  Tyr  Ser  Gln  Gln  Met  Lys  Gly  Lys  Gln
                    405                 410                      415

Leu  Ala  Ile  Lys  Lys  Met  Asn  Glu  Ile  Gln  Lys  Asn  Ile  Asp  Gly  Trp
               420                 425                      430

Glu  Gly  Lys  Asp  Ile  Gly  Gln  Cys  Cys  Asn  Glu  Phe  Ile  Met  Glu  Gly
          435                      440                      445

Thr  Leu  Thr  Arg  Val  Gly  Ala  Lys  His  Glu  Arg  His  Ile  Phe  Leu  Phe
     450                 455                      460

Asp  Gly  Leu  Met  Ile  Cys  Cys  Lys  Ser  Asn  His  Gly  Gln  Pro  Arg  Leu
465                      470                 475                           480

Pro  Gly  Ala  Ser  Ser  Ala  Glu  Tyr  Arg  Leu  Lys  Glu  Lys  Phe  Phe  Met
                    485                 490                      495

Arg  Lys  Val  Gln  Ile  Asn  Asp  Lys  Asp  Asp  Thr  Ser  Glu  Tyr  Lys  His
               500                 505                      510

Ala  Phe  Glu  Ile  Ile  Leu  Lys  Asp  Gly  Asn  Ser  Val  Ile  Phe  Ser  Ala
          515                 520                      525

Lys  Ser  Ala  Glu  Glu  Lys  Asn  Asn  Trp  Met  Ala  Ala  Leu  Ile  Ser  Leu
     530                 535                      540

Gln  Tyr  Arg  Ser  Thr  Leu  Glu  Arg  Met  Leu  Asp  Val  Thr  Val  Leu  Gln
545                      550                 555                           560

Glu  Glu  Lys  Glu  Glu  Gln  Met  Arg  Leu  Pro  Ser  Ala  Glu  Val  Tyr  Arg
               565                 570                      575

Phe  Ala  Glu  Pro  Asp  Ser  Glu  Glu  Asn  Ile  Leu  Phe  Glu  Glu  Asn  Val
               580                 585                      590

Gln  Pro  Lys  Ala  Gly  Ile  Pro  Ile  Ile  Lys  Ala  Gly  Thr  Val  Leu  Lys
          595                 600                      605

Leu  Ile  Glu  Arg  Leu  Thr  Tyr  His  Met  Tyr  Ala  Asp  Pro  Asn  Phe  Val
610                      615                      620

Arg  Thr  Phe  Leu  Thr  Thr  Tyr  Arg  Ser  Phe  Cys  Arg  Pro  Gln  Glu  Leu
625                      630                 635                           640

Leu  Ser  Leu  Leu  Ile  Glu  Arg  Phe  Glu  Ile  Pro  Glu  Pro  Glu  Pro  Thr
               645                 650                      655

Glu  Ala  Asp  Arg  Ile  Ala  Ile  Glu  Asn  Gly  Asp  Gln  Pro  Leu  Ser  Ala
               660                 665                      670

Glu  Leu  Lys  Arg  Phe  Arg  Lys  Glu  Tyr  Ile  Gln  Pro  Val  Gln  Leu  Arg
          675                 680                      685

Val  Leu  Asn  Val  Cys  Arg  His  Trp  Val  Glu  His  His  Phe  Tyr  Asp  Phe
     690                 695                      700

Glu  Arg  Asp  Ala  Asp  Leu  Leu  Gln  Arg  Met  Glu  Glu  Phe  Ile  Gly  Thr
```

-continued

```
705                   710                   715                   720
Val Arg Gly Lys Ala Met Lys Lys Trp Val Glu Ser Ile Thr Lys Ile
                725                   730                   735
Ile Gln Arg Lys Lys Ile Ala Arg Asp Asn Gly Pro Gly His Asn Ile
                740                   745                   750
Thr Phe Gln Ser Ser Pro Pro Thr Val Glu Trp His Ile Ser Arg Pro
                755                   760                   765
Gly His Ile Glu Thr Phe Asp Leu Leu Thr Leu His Pro Ile Glu Ile
                770                   775                   780
Ala Arg Gln Leu Thr Leu Leu Glu Ser Asp Leu Tyr Arg Ala Val Gln
785                   790                   795                   800
Pro Ser Glu Leu Val Gly Ser Val Trp Thr Lys Glu Asp Lys Glu Ile
                805                   810                   815
Asn Ser Pro Asn Leu Leu Lys Met Ile Arg His Thr Thr Asn Leu Thr
                820                   825                   830
Leu Trp Phe Glu Lys Cys Ile Glu Thr Glu Asn Leu Glu Glu Arg
                835                   840                   845
Val Ala Val Val Ser Arg Ile Ile Glu Ile Leu Gln Val Phe Gln Glu
                850                   855                   860
Leu Asn Asn Phe Asn Gly Val Leu Glu Val Val Ser Ala Met Asn Ser
865                   870                   875                   880
Ser Pro Val Tyr Arg Leu Asp His Thr Phe Glu Gln Ile Pro Ser Arg
                885                   890                   895
Gln Lys Lys Ile Leu Glu Glu Ala His Glu Leu Ser Glu Asp His Tyr
                900                   905                   910
Lys Lys Tyr Leu Ala Lys Leu Arg Ser Ile Asn Pro Pro Cys Val Pro
                915                   920                   925
Phe Phe Gly Ile Tyr Leu Thr Asn Ile Leu Lys Thr Glu Glu Gly Asn
                930                   935                   940
Pro Glu Val Leu Arg Arg His Gly Lys Glu Leu Ile Asn Phe Ser Lys
945                   950                   955                   960
Arg Arg Arg Val Ala Glu Ile Thr Gly Glu Ile Gln Gln Tyr Gln Asn
                965                   970                   975
Gln Pro Tyr Cys Leu Arg Val Glu Pro Asp Ile Lys Arg Phe Phe Glu
                980                   985                   990
Asn Leu Asn Pro Met Gly Asn Ser Met Glu Lys Glu Phe Thr Asp Tyr
                995                   1000                  1005
Leu Phe Asn Lys Ser Leu Glu Ile Glu Pro Arg His Pro Lys Pro Leu
                1010                  1015                  1020
Pro Arg Phe Pro Lys Lys Tyr Ser Tyr Pro Leu Lys Ser Pro Gly Val
1025                  1030                  1035                  1040
Arg Pro Ser Asn Pro Arg Pro Gly Thr Met Arg His Pro Thr Pro Leu
                1045                  1050                  1055
Gln Gln Glu Pro Arg Lys Ile Ser Tyr Ser Arg Ile Pro Glu Ser Glu
                1060                  1065                  1070
Thr Glu Ser Thr Ala Ser Ala Pro Asn Ser Pro Arg Thr Pro Leu Thr
                1075                  1080                  1085
Pro Pro Pro Ala Ser Gly Thr Ser Ser Asn Thr Asp Val Cys Ser Val
                1090                  1095                  1100
Phe Asp Ser Asp His Ser Ala Ser Pro Phe His Ser Arg Ser Ala Ser
1105                  1110                  1115                  1120
Val Ser Ser Ile Ser Leu Ser Lys Gly Thr Asp Glu Val Pro Val Pro
                1125                  1130                  1135
```

|                                                             |     |
|-------------------------------------------------------------|-----|
| Pro Pro Val Pro Pro Arg Arg Arg Pro Glu Ser Ala Pro Ala Glu Ser |     |
|         1140             1145              1150               |     |
| Ser Pro Ser Lys Ile Met Ser Lys His Leu Asp Ser Pro Pro Ala Ile |     |
|         1155             1160              1165               |     |
| Pro Pro Arg Gln Pro Thr Ser Lys Ala Tyr Ser Pro Arg Tyr Ser Ile |     |
|         1170             1175              1180               |     |
| Ser Asp Arg Thr Ser Ile Ser Asp Pro Pro Glu Ser Pro Pro Leu Leu |     |
| 1185             1190              1195                  1200 |     |
| Pro Pro Arg Glu Pro Val Arg Thr Pro Asp Val Phe Ser Ser Ser Pro |     |
|         1205             1210              1215               |     |
| Leu His Leu Gln Pro Pro Pro Leu Gly Lys Lys Ser Asp His Gly Asn |     |
|         1220             1225              1230               |     |
| Ala Phe Phe Pro Asn Ser Pro Ser Pro Phe Thr Pro Pro Pro Pro Gln |     |
|         1235             1240              1245               |     |
| Thr Pro Ser Pro His Gly Thr Arg Arg His Leu Pro Ser Pro Pro Leu |     |
|         1250             1255              1260               |     |
| Thr Gln Glu Met Asp Leu His Ser Ile Ala Gly Pro Pro Val Pro Pro |     |
| 1265             1270              1275                  1280 |     |
| Arg Gln Ser Thr Ser Gln Leu Ile Pro Lys Leu Pro Pro Lys Thr Tyr |     |
|         1285             1290              1295               |     |
| Lys Arg Glu His Thr His Pro Ser Met His Arg Asp Gly Pro Pro Leu |     |
|         1300             1305              1310               |     |
| Leu Glu Asn Ala His Ser Ser                                   |     |
|         1315                                                  |     |

( 2 ) INFORMATION FOR SEQ ID NO:3:

( i ) SEQUENCE CHARACTERISTICS:
        ( A ) LENGTH: 5253 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..3891

( x i ) SEQUENCE DESCRIPTION: SEQ ID NO:3:

| CCC ACC CTC TCA GCT AAT GAA GAG TCT CTC TAT TAT ATT GAA GAA CTG | 48  |
| Pro Thr Leu Ser Ala Asn Glu Glu Ser Leu Tyr Tyr Ile Glu Glu Leu |     |
| 1               5                   10                  15      |     |
| ATT TTT CAG CTG CTT AAT AAG CTA TGC ATG GCT CAA CCA AGG ACT GTT | 96  |
| Ile Phe Gln Leu Leu Asn Lys Leu Cys Met Ala Gln Pro Arg Thr Val |     |
|             20                  25                  30          |     |
| CAA GAT GTT GAG GAA CGA GTT CAA AAG ACC TTT CCT CAT CCT ATT GAT | 144 |
| Gln Asp Val Glu Glu Arg Val Gln Lys Thr Phe Pro His Pro Ile Asp |     |
|             35                  40                  45          |     |
| AAA TGG GCA ATT GCT GAT GCA CAA TCT GCT ATA GAG AAA CGA AAA CGA | 192 |
| Lys Trp Ala Ile Ala Asp Ala Gln Ser Ala Ile Glu Lys Arg Lys Arg |     |
|     50                  55                  60                  |     |
| AGA AAT CCT CTC TTA CTA CCT GTG GAC AAA ATC CAT CCT TCC TTG AAG | 240 |
| Arg Asn Pro Leu Leu Leu Pro Val Asp Lys Ile His Pro Ser Leu Lys |     |
| 65                  70                  75                  80  |     |
| GAA GTT TTG GGG TAT AAA GTG GAC TAC CAT GTG TCC CTC TAC ATT GTG | 288 |
| Glu Val Leu Gly Tyr Lys Val Asp Tyr His Val Ser Leu Tyr Ile Val |     |
|             85                  90                  95          |     |
| GCT GTA TTG GAG TAT ATC TCA GCA GAT ATT TTG AAA TTG GCT GGT AAT | 336 |
| Ala Val Leu Glu Tyr Ile Ser Ala Asp Ile Leu Lys Leu Ala Gly Asn |     |
|             100                 105                 110         |     |

```
TAT GTT TTT AAT ATC CGG CAT TAT GAA ATA TCT CAG CAA GAC ATT AAA      384
Tyr Val Phe Asn Ile Arg His Tyr Glu Ile Ser Gln Gln Asp Ile Lys
        115                 120                 125

GTG TCC ATG TGT GCA GAT AAG GTT TTG ATG GAC ATG TTC GAT CAG GAT      432
Val Ser Met Cys Ala Asp Lys Val Leu Met Asp Met Phe Asp Gln Asp
    130                 135                 140

GAT GAT ATA GGC TTG GTT TCT CTC TGT GAA GAT GAG CCT TGT TCT TCT      480
Asp Asp Ile Gly Leu Val Ser Leu Cys Glu Asp Glu Pro Cys Ser Ser
145                 150                 155                 160

GGT GAG CTA AAC TAT TAT GAC CTC GTC AGG ACT GAA ATT GCA GAA GAA      528
Gly Glu Leu Asn Tyr Tyr Asp Leu Val Arg Thr Glu Ile Ala Glu Glu
                165                 170                 175

AGA CAG TAT CTA CGG GAG CTG AAT ATG ATC ATT AAA GTG TTC CGG GAA      576
Arg Gln Tyr Leu Arg Glu Leu Asn Met Ile Ile Lys Val Phe Arg Glu
            180                 185                 190

GCC TTT CTC TTG GAC AGA AAG TTG TTC AAG CCT TCT GAA ATT GAA AAG      624
Ala Phe Leu Leu Asp Arg Lys Leu Phe Lys Pro Ser Glu Ile Glu Lys
        195                 200                 205

ATT TTC AGT AAC ATT TCA GAT ATA CAT GAA TTG ACT GTG AAA CTT TTA      672
Ile Phe Ser Asn Ile Ser Asp Ile His Glu Leu Thr Val Lys Leu Leu
    210                 215                 220

GGT TTA ATT GAA GAC ACA GTA GAA ATG ACA GAT GAA AGT AGT CCT CAT      720
Gly Leu Ile Glu Asp Thr Val Glu Met Thr Asp Glu Ser Ser Pro His
225                 230                 235                 240

CCA TTA GCT GGT AGC TGT TTT GAA GAT TTA GCA GAG GAG CAA GCG TTT      768
Pro Leu Ala Gly Ser Cys Phe Glu Asp Leu Ala Glu Glu Gln Ala Phe
                245                 250                 255

GAT CCC TAT GAA ACA TTA TCA CAG GAC ATT CTT GCA CCA GAG TTT AAT      816
Asp Pro Tyr Glu Thr Leu Ser Gln Asp Ile Leu Ala Pro Glu Phe Asn
            260                 265                 270

GAC CAC TTC AGC AAG TTG ATG GCC AGA CCT GCA GTC GCT CTA CAT TTT      864
Asp His Phe Ser Lys Leu Met Ala Arg Pro Ala Val Ala Leu His Phe
        275                 280                 285

CAG TCC ATT GCT GAC GGC TTT AAG GAG GCT GTT CGT TAT GTC CTT CCA      912
Gln Ser Ile Ala Asp Gly Phe Lys Glu Ala Val Arg Tyr Val Leu Pro
    290                 295                 300

CGC CTC ATG CTG GTT CCC GTG TAT CAC TGT TGG CAT TAC TTT GAA TTA      960
Arg Leu Met Leu Val Pro Val Tyr His Cys Trp His Tyr Phe Glu Leu
305                 310                 315                 320

TTA AAG TTG AAG GCA TGC AGT GAA GAG CAG GAG GAC AAA GAG TGT TTG     1008
Leu Lys Leu Lys Ala Cys Ser Glu Glu Gln Glu Asp Lys Glu Cys Leu
                325                 330                 335

AAT CAG GCT ATA ACT GCC CTC ATG AAC CTC CAA GGC AGC ATG GAC CGC     1056
Asn Gln Ala Ile Thr Ala Leu Met Asn Leu Gln Gly Ser Met Asp Arg
            340                 345                 350

ATT TAC AAG CAG CAC TCC CCC AGA CGC CGG CCT GGG GAT CCA GTT TGC     1104
Ile Tyr Lys Gln His Ser Pro Arg Arg Pro Gly Asp Pro Val Cys
        355                 360                 365

CTT TTT TAC AAT CGT CAA TTA AGA AGC AAA CAC CTG GCT ATC AAA AAA     1152
Leu Phe Tyr Asn Arg Gln Leu Arg Ser Lys His Leu Ala Ile Lys Lys
    370                 375                 380

ATG AAT GAA ATT CAG AAA AAC ATA GAT GGG TGG GAA GGC AAA GAT ATC     1200
Met Asn Glu Ile Gln Lys Asn Ile Asp Gly Trp Glu Gly Lys Asp Ile
385                 390                 395                 400

GGA CAG TGT TGT AAT GAG TTC ATA ATG GAG GGG CCA CTG ACC AGA ATT     1248
Gly Gln Cys Cys Asn Glu Phe Ile Met Glu Gly Pro Leu Thr Arg Ile
                405                 410                 415

GGT GCT AAA CAC GAA AGG CAT ATC TTT CTC TTT GAT GGC TTA ATG ATC     1296
Gly Ala Lys His Glu Arg His Ile Phe Leu Phe Asp Gly Leu Met Ile
            420                 425                 430
```

| | | | | | | | | | | | | | | | | |
|---|---|---|---|---|---|---|---|---|---|---|---|---|---|---|---|---|
| AGC | TGT | AAA | CCC | AAT | CAT | GGC | CAG | ACC | CGG | CTT | CCA | GGA | TAT | AGC | AGT | 1344 |
| Ser | Cys | Lys | Pro | Asn | His | Gly | Gln | Thr | Arg | Leu | Pro | Gly | Tyr | Ser | Ser | |
| | | 435 | | | | 440 | | | | | | 445 | | | | |
| GCA | GAA | TAC | AGA | TTA | AAG | GAG | AAG | TTT | GTC | ATG | AGG | AAA | ATT | CAA | ATC | 1392 |
| Ala | Glu | Tyr | Arg | Leu | Lys | Glu | Lys | Phe | Val | Met | Arg | Lys | Ile | Gln | Ile | |
| 450 | | | | | 455 | | | | | 460 | | | | | | |
| TGT | GAT | AAG | GAA | GAC | GCC | TGT | GAG | TAC | AGA | CAT | GCT | TTT | GAA | TTA | GTG | 1440 |
| Cys | Asp | Lys | Glu | Asp | Ala | Cys | Glu | Tyr | Arg | His | Ala | Phe | Glu | Leu | Val | |
| 465 | | | | | 470 | | | | | 475 | | | | | 480 | |
| TCC | AAA | GAT | GAA | AAC | AGT | GTA | ATA | TTT | GCT | GCC | AAA | TCA | GCT | GAA | GAG | 1488 |
| Ser | Lys | Asp | Glu | Asn | Ser | Val | Ile | Phe | Ala | Ala | Lys | Ser | Ala | Glu | Glu | |
| | | | | 485 | | | | | 490 | | | | | 495 | | |
| AAA | AAC | AAC | TGG | ATG | GCA | GCC | CTC | ATT | TCC | CTG | CAC | TAT | CGC | AGC | ACT | 1536 |
| Lys | Asn | Asn | Trp | Met | Ala | Ala | Leu | Ile | Ser | Leu | His | Tyr | Arg | Ser | Thr | |
| | | | 500 | | | | | 505 | | | | | 510 | | | |
| CTA | GAC | AGA | ATG | CTG | GAC | TCT | GTG | CTG | CTG | AAA | GAA | GAG | AAT | GAG | CAG | 1584 |
| Leu | Asp | Arg | Met | Leu | Asp | Ser | Val | Leu | Leu | Lys | Glu | Glu | Asn | Glu | Gln | |
| | | 515 | | | | | 520 | | | | | 525 | | | | |
| CCC | CTG | AGG | CTA | CCC | AGT | CCA | GAT | ATG | TAT | CGC | TTT | GTG | GTA | ACA | GAC | 1632 |
| Pro | Leu | Arg | Leu | Pro | Ser | Pro | Asp | Met | Tyr | Arg | Phe | Val | Val | Thr | Asp | |
| 530 | | | | | 535 | | | | | 540 | | | | | | |
| TCT | GAG | GAA | AAC | ATT | GTG | TTT | GAA | GAC | AAC | TTG | CAA | AGC | AGA | AGT | GGG | 1680 |
| Ser | Glu | Glu | Asn | Ile | Val | Phe | Glu | Asp | Asn | Leu | Gln | Ser | Arg | Ser | Gly | |
| 545 | | | | | 550 | | | | | 555 | | | | | 560 | |
| ATC | CCC | ATA | ATT | AAA | GGA | GGC | ACT | GTG | GTG | AAG | TTG | ATC | GAA | AGG | CTA | 1728 |
| Ile | Pro | Ile | Ile | Lys | Gly | Gly | Thr | Val | Val | Lys | Leu | Ile | Glu | Arg | Leu | |
| | | | | 565 | | | | | 570 | | | | | 575 | | |
| ACA | TAC | CAC | ATG | TAT | GCA | GAT | CCC | AAT | TTT | GTT | CGT | ACT | TTT | CTT | ACT | 1776 |
| Thr | Tyr | His | Met | Tyr | Ala | Asp | Pro | Asn | Phe | Val | Arg | Thr | Phe | Leu | Thr | |
| | | | 580 | | | | | 585 | | | | | 590 | | | |
| ACA | TAT | CGT | TCA | TTT | TGT | AAA | CCA | CAG | GAA | TTG | CTA | AAC | TTG | CTG | ATA | 1824 |
| Thr | Tyr | Arg | Ser | Phe | Cys | Lys | Pro | Gln | Glu | Leu | Leu | Asn | Leu | Leu | Ile | |
| | | 595 | | | | | 600 | | | | | 605 | | | | |
| GAA | CGG | TTT | GAA | ATT | CCA | GAA | CCA | GAA | CCT | ACT | GAG | GCA | GAC | AAG | CTG | 1872 |
| Glu | Arg | Phe | Glu | Ile | Pro | Glu | Pro | Glu | Pro | Thr | Glu | Ala | Asp | Lys | Leu | |
| | 610 | | | | | 615 | | | | | 620 | | | | | |
| GCG | TTA | GAA | AAA | GGC | GAG | CAG | CCA | ATC | AGC | GCA | GAT | CTG | AAA | AGA | TTC | 1920 |
| Ala | Leu | Glu | Lys | Gly | Glu | Gln | Pro | Ile | Ser | Ala | Asp | Leu | Lys | Arg | Phe | |
| 625 | | | | | 630 | | | | | 635 | | | | | 640 | |
| CGC | AAG | GAA | TAC | GTC | CAA | CCT | GTG | CAG | CTT | AGG | GTC | TTG | AAT | GTC | TTT | 1968 |
| Arg | Lys | Glu | Tyr | Val | Gln | Pro | Val | Gln | Leu | Arg | Val | Leu | Asn | Val | Phe | |
| | | | | 645 | | | | | 650 | | | | | 655 | | |
| CGC | CAC | TGG | GTT | GAG | CAT | CAT | TAT | TAT | GAC | TTT | GAA | AGA | GAC | TTG | GAA | 2016 |
| Arg | His | Trp | Val | Glu | His | His | Tyr | Tyr | Asp | Phe | Glu | Arg | Asp | Leu | Glu | |
| | | | | 660 | | | | | 665 | | | | | 670 | | |
| CTG | CTT | GAA | AGA | CTA | GAA | TCC | TTC | ATT | TCA | AGT | GTA | AGA | GGG | AAA | GCC | 2064 |
| Leu | Leu | Glu | Arg | Leu | Glu | Ser | Phe | Ile | Ser | Ser | Val | Arg | Gly | Lys | Ala | |
| | | 675 | | | | | 680 | | | | | 685 | | | | |
| ATG | AAG | AAA | TGG | GTA | GAA | TCC | ATT | GCT | AAA | ATA | ATC | AAG | AGG | AAG | AAG | 2112 |
| Met | Lys | Lys | Trp | Val | Glu | Ser | Ile | Ala | Lys | Ile | Ile | Lys | Arg | Lys | Lys | |
| 690 | | | | | 695 | | | | | 700 | | | | | | |
| CAA | GCT | CAG | GCA | AAT | GGA | ATA | AGC | CAT | AAT | ATC | ACC | TTT | GAA | AGT | TCC | 2160 |
| Gln | Ala | Gln | Ala | Asn | Gly | Ile | Ser | His | Asn | Ile | Thr | Phe | Glu | Ser | Ser | |
| 705 | | | | | 710 | | | | | 715 | | | | | 720 | |
| CCC | CCA | CCA | GTG | GAA | TGG | CAC | ATC | AGT | AGA | ACA | GGA | CAG | TTC | GAA | ACA | 2208 |
| Pro | Pro | Pro | Val | Glu | Trp | His | Ile | Ser | Arg | Thr | Gly | Gln | Phe | Glu | Thr | |
| | | | | 725 | | | | | 730 | | | | | 735 | | |
| TTT | GAC | CTT | ATG | ACA | CTT | CAT | CCA | ATA | GAG | ATC | GCA | CGG | CAG | CTA | ACA | 2256 |
| Phe | Asp | Leu | Met | Thr | Leu | His | Pro | Ile | Glu | Ile | Ala | Arg | Gln | Leu | Thr | |
| | | | 740 | | | | | 745 | | | | | 750 | | | |

-continued

| | | | | | | | | | | | | | | | | |
|---|---|---|---|---|---|---|---|---|---|---|---|---|---|---|---|---|
| CTT | TTG | GAA | TCT | GAC | CTC | TAC | AGG | AAA | GTC | CAG | CCC | TCT | GAA | CTT | GTA | 2304 |
| Leu | Leu | Glu | Ser | Asp | Leu | Tyr | Arg | Lys | Val | Gln | Pro | Ser | Glu | Leu | Val | |
| | | 755 | | | | | 760 | | | | | 765 | | | | |
| GGG | AGT | GTC | TGG | ACC | AAA | GAA | GAT | AAA | GAA | ATA | AAT | TCT | CCA | AAC | TTA | 2352 |
| Gly | Ser | Val | Trp | Thr | Lys | Glu | Asp | Lys | Glu | Ile | Asn | Ser | Pro | Asn | Leu | |
| | 770 | | | | | 775 | | | | | 780 | | | | | |
| TTA | AAA | ATG | ATT | CGC | CAT | ACA | ACA | AAC | CTC | ACT | CTA | TGG | TTT | GAG | AAA | 2400 |
| Leu | Lys | Met | Ile | Arg | His | Thr | Thr | Asn | Leu | Thr | Leu | Trp | Phe | Glu | Lys | |
| 785 | | | | | 790 | | | | | 795 | | | | | 800 | |
| TGC | ATT | GTG | GAA | GCA | GAA | AAC | TTT | GAA | GAA | CGG | GTG | GCA | GTG | CTC | AGC | 2448 |
| Cys | Ile | Val | Glu | Ala | Glu | Asn | Phe | Glu | Glu | Arg | Val | Ala | Val | Leu | Ser | |
| | | | | 805 | | | | | 810 | | | | | 815 | | |
| AGA | ATA | GTA | GAA | ATT | CTG | CAA | GTA | TTT | CAA | GAC | TTG | AAT | AAT | TTC | AAT | 2496 |
| Arg | Ile | Val | Glu | Ile | Leu | Gln | Val | Phe | Gln | Asp | Leu | Asn | Asn | Phe | Asn | |
| | | | 820 | | | | | 825 | | | | | 830 | | | |
| GGC | GTG | TTG | GAG | ATA | GTG | AGT | GCA | GTC | AAC | TCC | GTG | TCA | GTG | TAC | AGG | 2544 |
| Gly | Val | Leu | Glu | Ile | Val | Ser | Ala | Val | Asn | Ser | Val | Ser | Val | Tyr | Arg | |
| | | 835 | | | | | 840 | | | | | 845 | | | | |
| CTA | GAC | CAC | ACG | TTT | GAG | GCA | CTG | CAG | GAA | AGG | AAG | CGG | AGA | ATT | TTG | 2592 |
| Leu | Asp | His | Thr | Phe | Glu | Ala | Leu | Gln | Glu | Arg | Lys | Arg | Arg | Ile | Leu | |
| | 850 | | | | | 855 | | | | | 860 | | | | | |
| GAT | GAC | GCT | GTG | GAA | CTA | AGT | CAG | GAC | CAC | TTT | AAA | AAG | TAC | CTA | GTA | 2640 |
| Asp | Asp | Ala | Val | Glu | Leu | Ser | Gln | Asp | His | Phe | Lys | Lys | Tyr | Leu | Val | |
| 865 | | | | | 870 | | | | | 875 | | | | | 880 | |
| AAA | CTT | AAG | TCA | ATC | AAT | CCG | CCT | TGT | GTG | CCT | TTT | TTT | GGA | ATA | TAT | 2688 |
| Lys | Leu | Lys | Ser | Ile | Asn | Pro | Pro | Cys | Val | Pro | Phe | Phe | Gly | Ile | Tyr | |
| | | | | 885 | | | | | 890 | | | | | 895 | | |
| TTA | ACA | AAT | ATT | CTG | AAG | ACT | GAA | GAA | GGG | AAC | AGT | GAC | TTT | CTA | AAG | 2736 |
| Leu | Thr | Asn | Ile | Leu | Lys | Thr | Glu | Glu | Gly | Asn | Ser | Asp | Phe | Leu | Lys | |
| | | | 900 | | | | | 905 | | | | | 910 | | | |
| AGG | AAA | GGG | AAA | GAT | TTG | ATC | AAT | TTC | AGT | AAG | AGG | AGG | AAA | GTG | GCT | 2784 |
| Arg | Lys | Gly | Lys | Asp | Leu | Ile | Asn | Phe | Ser | Lys | Arg | Arg | Lys | Val | Ala | |
| | | 915 | | | | | 920 | | | | | 925 | | | | |
| GAA | ATA | ACT | GGA | GAG | ATC | CAG | CAG | TAT | CAG | AAC | CAA | CCG | TAC | TGC | TTA | 2832 |
| Glu | Ile | Thr | Gly | Glu | Ile | Gln | Gln | Tyr | Gln | Asn | Gln | Pro | Tyr | Cys | Leu | |
| | 930 | | | | | 935 | | | | | 940 | | | | | |
| CGG | ACA | GAA | CCA | GAA | ATG | AGG | AGA | TTC | TTT | GAA | AAC | CTC | AAC | CCC | ATG | 2880 |
| Arg | Thr | Glu | Pro | Glu | Met | Arg | Arg | Phe | Phe | Glu | Asn | Leu | Asn | Pro | Met | |
| 945 | | | | | 950 | | | | | 955 | | | | | 960 | |
| GGA | ATT | TTA | TCT | GAA | AAA | GAG | TTT | ACA | GAT | TAT | TTG | TTC | AAC | AAA | TCA | 2928 |
| Gly | Ile | Leu | Ser | Glu | Lys | Glu | Phe | Thr | Asp | Tyr | Leu | Phe | Asn | Lys | Ser | |
| | | | | 965 | | | | | 970 | | | | | 975 | | |
| TTA | GAA | ATC | GAA | CCC | CGA | AAC | TGC | AAA | CAA | CCA | CCT | CGA | TTT | CCT | AGG | 2976 |
| Leu | Glu | Ile | Glu | Pro | Arg | Asn | Cys | Lys | Gln | Pro | Pro | Arg | Phe | Pro | Arg | |
| | | | 980 | | | | | 985 | | | | | 990 | | | |
| AAG | TCA | ACC | TTT | TCC | TTA | AAA | TCT | CCT | GGA | ATA | AGG | CCC | AAT | GCT | GGC | 3024 |
| Lys | Ser | Thr | Phe | Ser | Leu | Lys | Ser | Pro | Gly | Ile | Arg | Pro | Asn | Ala | Gly | |
| | | 995 | | | | | 1000 | | | | | 1005 | | | | |
| CGC | CAT | GGC | TCT | ACC | TCA | GGC | ACG | CTA | CGA | GGT | CAC | CCA | ACG | CCT | CTG | 3072 |
| Arg | His | Gly | Ser | Thr | Ser | Gly | Thr | Leu | Arg | Gly | His | Pro | Thr | Pro | Leu | |
| | 1010 | | | | | 1015 | | | | | 1020 | | | | | |
| GAA | AGA | GAG | CCT | TAT | AAG | ATA | AGC | TTT | AGC | CGG | ATC | GCT | GAG | ACA | GAG | 3120 |
| Glu | Arg | Glu | Pro | Tyr | Lys | Ile | Ser | Phe | Ser | Arg | Ile | Ala | Glu | Thr | Glu | |
| 1025 | | | | | 1030 | | | | | 1035 | | | | | 1040 | |
| CTA | GAA | TCA | ACA | GTG | TCT | GCA | CCA | ACC | TCC | CCC | AAC | ACT | CCA | TCC | ACC | 3168 |
| Leu | Glu | Ser | Thr | Val | Ser | Ala | Pro | Thr | Ser | Pro | Asn | Thr | Pro | Ser | Thr | |
| | | | | 1045 | | | | | 1050 | | | | | 1055 | | |
| CCA | CCA | GTG | TCT | GCT | TCT | TCA | GAC | CAC | AGC | GTG | TTT | CTA | GAT | GTG | GAC | 3216 |
| Pro | Pro | Val | Ser | Ala | Ser | Ser | Asp | His | Ser | Val | Phe | Leu | Asp | Val | Asp | |
| | | | | 1060 | | | | | 1065 | | | | | 1070 | | |

| | |
|---|---:|
| CTC AAT AGC TCC TGT GGC AGC AAC ACC ATC TTT GCT CCA GTC CTC TTG<br>Leu Asn Ser Ser Cys Gly Ser Asn Thr Ile Phe Ala Pro Val Leu Leu<br>　　　1075　　　　　　　　1080　　　　　　　　1085 | 3264 |
| CCA CAC TCA AAG ACT TTC TTC AGC TCA TGT GGA AGT TTA CAC AAA CTG<br>Pro His Ser Lys Thr Phe Phe Ser Ser Cys Gly Ser Leu His Lys Leu<br>　　　1090　　　　　　　　1095　　　　　　　　1100 | 3312 |
| AGT GAA GAG CCA CTA ATT CCT CCT CCG CTT CCC CCT CGG AAA AAG TTT<br>Ser Glu Glu Pro Leu Ile Pro Pro Pro Leu Pro Pro Arg Lys Lys Phe<br>1105　　　　　　　　1110　　　　　　　　1115　　　　　　　　1120 | 3360 |
| GAT CAT GAT GCT CTC AAT TCC AAG GGA GCT GTG AAA TCT GAT GAT GAC<br>Asp His Asp Ala Leu Asn Ser Lys Gly Ala Val Lys Ser Asp Asp Asp<br>　　　　　　　　1125　　　　　　　　1130　　　　　　　　1135 | 3408 |
| CCT CCT GCT ATT CCA CCA AGA CAG CCC CCT CCT CCG AAG GTA AAG CCA<br>Pro Pro Ala Ile Pro Pro Arg Gln Pro Pro Pro Lys Val Lys Pro<br>　　　　　　　　1140　　　　　　　　1145　　　　　　　　1150 | 3456 |
| AGA GTT CCT GTC CTC ATG GGT ACA TTT GAT GGG CCT GTG CCC AGT CCA<br>Arg Val Pro Val Leu Met Gly Thr Phe Asp Gly Pro Val Pro Ser Pro<br>　　　　　　　1155　　　　　　　　1160　　　　　　　　1165 | 3504 |
| CCT CCA CCT CCT CCA AGA GAC CCT CTT CCT GAT ACC CCT CCA CCA GTT<br>Pro Pro Pro Pro Pro Arg Asp Pro Leu Pro Asp Thr Pro Pro Pro Val<br>　　　1170　　　　　　　　1175　　　　　　　　1180 | 3552 |
| CCT CTT CGG CCT CCG GAA CAC TTT ATA AAC TGT CCA TTT AAT CTT CAG<br>Pro Leu Arg Pro Pro Glu His Phe Ile Asn Cys Pro Phe Asn Leu Gln<br>1185　　　　　　　　1190　　　　　　　　1195　　　　　　　　1200 | 3600 |
| CCG CCT CCA CTG GGC CAT CCT CAC AGA GAC CCA GAC TGG CTC AGA GAC<br>Pro Pro Pro Leu Gly His Pro His Arg Asp Pro Asp Trp Leu Arg Asp<br>　　　　　　　　1205　　　　　　　　1210　　　　　　　　1215 | 3648 |
| GTC AGC ACG TGT CCT AAC TCA CCA AGC ACT CCT CCC ACT ACG CCC TCT<br>Val Ser Thr Cys Pro Asn Ser Pro Ser Thr Pro Pro Thr Thr Pro Ser<br>　　　　　　　　1220　　　　　　　　1225　　　　　　　　1230 | 3696 |
| CCA CGG ATT CCA CGC AGC TGT CAC TTG CTC AGC TCC AGT CAC AGC AGC<br>Pro Arg Ile Pro Arg Ser Cys His Leu Leu Ser Ser Ser His Ser Ser<br>　　　1235　　　　　　　　1240　　　　　　　　1245 | 3744 |
| CTT GCT CAT CTT CCA GCT CCT CCT GTC CCA CCA AGG CAG AAT TCA AGC<br>Leu Ala His Leu Pro Ala Pro Pro Val Pro Pro Arg Gln Asn Ser Ser<br>　　　1250　　　　　　　　1255　　　　　　　　1260 | 3792 |
| CCT CTC TTA CCA AAG CTG CCA CCA AAG ACT TAC AAA CGG GAG CTT TCC<br>Pro Leu Leu Pro Lys Leu Pro Pro Lys Thr Tyr Lys Arg Glu Leu Ser<br>1265　　　　　　　　1270　　　　　　　　1275　　　　　　　　1280 | 3840 |
| CAC CCG CCA CTG TAT AGA CTG CCT CTG CTG GAA AAT GCA GAA ACT CCT<br>His Pro Pro Leu Tyr Arg Leu Pro Leu Leu Glu Asn Ala Glu Thr Pro<br>　　　　　　　　1285　　　　　　　　1290　　　　　　　　1295 | 3888 |
| CAA TGACCTTGGC CATATGTAGT CATTGACACT GGAATAGTAT TTGTAAAGGT<br>Gln | 3941 |
| TTTTAATTTA TTCAAAAAGA CATAGTATTT TAGTACTTTT TACAGAAATG CTACTGATTA | 4001 |
| AATAAGCTCT TAAGAATTAG TAAACTTGTT GGATGGCAGT GGCCCACAGC TGTAATCCCA | 4061 |
| GCACCCTGGT TGCAGGGGCA GTGGGCTTCA GGGTTTGAGA GCAGCCTGGT CTACAGAGCA | 4121 |
| AGTCCCAGGA CAGCCAGGGC TACACAAAAA AACCTGTCT CAAAAGTCAA AATACAAACA | 4181 |
| AAAGAGAGAA AAGGAAGGAA GGAAAGAATT TGAAATATTA AAATGCAAAA GCCCTTCACC | 4241 |
| ATAGCCCCCA GGTGATCAGC AGCATTGCTT CCTCGGCTCC TCAGTGCTGC CCTAGGCCAG | 4301 |
| TATAAAGACT GTATTGCACT GTAGACTCTG CTAGCAGACG GCACTGAGAG GAGCCAGCGC | 4361 |
| TCGAGGGCCG TTCTCACGCC TGACTGATAG ATACCTTTTT AGGGTGATGA ACTTACACAG | 4421 |
| ATGCAGAAGA TATGGGGTGG TGGTCCTGGG TTTTAACCCT CTGACCGTCT TCTAGCTTCT | 4481 |
| AATTTTGTTT GGTTTTTACA TCTAGGAGAC TTAGGAATAA TACCCGCTGT TCTTAAACTC | 4541 |

| | | | | | |
|---|---|---|---|---|---|
| TTTGAGACCA | TGTCTTAAAT | GTCAGTATTT | GCTGCTGAAG | ACAAAAACGG | AAAATAGAAT | 4601
| GAAATAATAG | AATGCACTGT | GTTTATTATT | TTGTTAAAAT | TATAAACAGT | TCTACATAAC | 4661
| CTGATTATAG | AAGAAGGGCA | TGTGTTCATT | AAGATGTGCC | TTTTGTTTTG | CAGTGTATGG | 4721
| TGTTTAGCTA | ATCATTGTTT | AGCTAATGAT | TTGCCTATTA | TTTGGGAAGA | CAAAATTAAT | 4781
| ATGCCATATA | TGTACAGTTT | ATTTATATTG | TATATATTTA | AAGATAATGC | TAATAACCTC | 4841
| TATAAATGTA | AGTGACTTGA | GGCCTATAAT | ACAATCTGCT | ATTTGACTAA | TTTGTAAGTC | 4901
| TGGAACAAAA | GTGTCTTATG | GCATAAGAAC | CAACTGCCAT | TGTCAAACCT | ATTAACTGTC | 4961
| TTTAATCTCG | TGTTAACTGA | AATTTTTGAA | AAGTTTTTCC | AGATTAGTAA | TATTTAAACA | 5021
| GAAAATACTT | TAAAAAGCTT | TATTAAATTT | TTTAATCAGA | CAGGATAAAG | CTTTGCCATT | 5081
| TGGATACTAT | CATTCAAAGT | GATCAAGGTA | TGTATGTTAT | GCTGATAGTG | CAGTAGCAGC | 5141
| CATTGTAAAG | TAGCCAAAAG | CCACGTTGTT | TATCTACTGG | TCTGTGGCCT | TTTACTGTGC | 5201
| TTTGTATCAG | AGTTCTTAAC | AAGATTAATA | AATCACCTCA | GTCTTAATTT | GT | 5253

( 2 ) INFORMATION FOR SEQ ID NO:4:

( i ) SEQUENCE CHARACTERISTICS:
        ( A ) LENGTH: 1297 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Pro  Thr  Leu  Ser  Ala  Asn  Glu  Glu  Ser  Leu  Tyr  Tyr  Ile  Glu  Glu  Leu
 1              5                        10                       15

Ile  Phe  Gln  Leu  Leu  Asn  Lys  Leu  Cys  Met  Ala  Gln  Pro  Arg  Thr  Val
               20                        25                       30

Gln  Asp  Val  Glu  Glu  Arg  Val  Gln  Lys  Thr  Phe  Pro  His  Pro  Ile  Asp
               35                        40                       45

Lys  Trp  Ala  Ile  Ala  Asp  Ala  Gln  Ser  Ala  Ile  Glu  Lys  Arg  Lys  Arg
               50                        55                  60

Arg  Asn  Pro  Leu  Leu  Leu  Pro  Val  Asp  Lys  Ile  His  Pro  Ser  Leu  Lys
 65                       70                        75                       80

Glu  Val  Leu  Gly  Tyr  Lys  Val  Asp  Tyr  His  Val  Ser  Leu  Tyr  Ile  Val
                    85                        90                       95

Ala  Val  Leu  Glu  Tyr  Ile  Ser  Ala  Asp  Ile  Leu  Lys  Leu  Ala  Gly  Asn
                    100                       105                      110

Tyr  Val  Phe  Asn  Ile  Arg  His  Tyr  Glu  Ile  Ser  Gln  Gln  Asp  Ile  Lys
               115                       120                      125

Val  Ser  Met  Cys  Ala  Asp  Lys  Val  Leu  Met  Asp  Met  Phe  Asp  Gln  Asp
     130                      135                      140

Asp  Asp  Ile  Gly  Leu  Val  Ser  Leu  Cys  Glu  Asp  Glu  Pro  Cys  Ser  Ser
145                      150                      155                      160

Gly  Glu  Leu  Asn  Tyr  Tyr  Asp  Leu  Val  Arg  Thr  Glu  Ile  Ala  Glu  Glu
               165                       170                      175

Arg  Gln  Tyr  Leu  Arg  Glu  Leu  Asn  Met  Ile  Ile  Lys  Val  Phe  Arg  Glu
               180                       185                      190

Ala  Phe  Leu  Leu  Asp  Arg  Lys  Leu  Phe  Lys  Pro  Ser  Glu  Ile  Glu  Lys
               195                       200                      205

Ile  Phe  Ser  Asn  Ile  Ser  Asp  Ile  His  Glu  Leu  Thr  Val  Lys  Leu  Leu
     210                      215                      220

Gly  Leu  Ile  Glu  Asp  Thr  Val  Glu  Met  Thr  Asp  Glu  Ser  Ser  Pro  His
225                      230                      235                      240
```

-continued

| | | | | | | | | | | | | | | |
|---|---|---|---|---|---|---|---|---|---|---|---|---|---|---|
| Pro | Leu | Ala | Gly | Ser | Cys | Phe | Glu | Asp | Leu | Ala | Glu | Glu | Ala | Phe |
| | | | | 245 | | | | 250 | | | | | 255 | |
| Asp | Pro | Tyr | Glu | Thr | Leu | Ser | Gln | Asp | Ile | Leu | Ala | Pro | Glu | Phe | Asn |
| | | | 260 | | | | 265 | | | | 270 | | | | |
| Asp | His | Phe | Ser | Lys | Leu | Met | Ala | Arg | Pro | Ala | Val | Ala | Leu | His | Phe |
| | | 275 | | | | 280 | | | | 285 | | | | | |
| Gln | Ser | Ile | Ala | Asp | Gly | Phe | Lys | Glu | Ala | Val | Arg | Tyr | Val | Leu | Pro |
| | 290 | | | | 295 | | | | 300 | | | | | | |
| Arg | Leu | Met | Leu | Val | Pro | Val | Tyr | His | Cys | Trp | His | Tyr | Phe | Glu | Leu |
| 305 | | | | 310 | | | | 315 | | | | | 320 | | |
| Leu | Lys | Leu | Lys | Ala | Cys | Ser | Glu | Glu | Gln | Glu | Asp | Lys | Glu | Cys | Leu |
| | | | 325 | | | | 330 | | | | | 335 | | | |
| Asn | Gln | Ala | Ile | Thr | Ala | Leu | Met | Asn | Leu | Gln | Gly | Ser | Met | Asp | Arg |
| | | 340 | | | | 345 | | | | 350 | | | | | |
| Ile | Tyr | Lys | Gln | His | Ser | Pro | Arg | Arg | Pro | Gly | Asp | Pro | Val | Cys |
| | 355 | | | | 360 | | | | 365 | | | | | |
| Leu | Phe | Tyr | Asn | Arg | Gln | Leu | Arg | Ser | Lys | His | Leu | Ala | Ile | Lys | Lys |
| | 370 | | | | 375 | | | | 380 | | | | | | |
| Met | Asn | Glu | Ile | Gln | Lys | Asn | Ile | Asp | Gly | Trp | Glu | Gly | Lys | Asp | Ile |
| 385 | | | | 390 | | | | 395 | | | | | 400 | | |
| Gly | Gln | Cys | Cys | Asn | Glu | Phe | Ile | Met | Glu | Gly | Pro | Leu | Thr | Arg | Ile |
| | | | 405 | | | | 410 | | | | 415 | | | | |
| Gly | Ala | Lys | His | Glu | Arg | His | Ile | Phe | Leu | Phe | Asp | Gly | Leu | Met | Ile |
| | | 420 | | | | 425 | | | | 430 | | | | | |
| Ser | Cys | Lys | Pro | Asn | His | Gly | Gln | Thr | Arg | Leu | Pro | Gly | Tyr | Ser | Ser |
| | | 435 | | | | 440 | | | | 445 | | | | | |
| Ala | Glu | Tyr | Arg | Leu | Lys | Glu | Lys | Phe | Val | Met | Arg | Lys | Ile | Gln | Ile |
| | 450 | | | | 455 | | | | 460 | | | | | | |
| Cys | Asp | Lys | Glu | Asp | Ala | Cys | Glu | Tyr | Arg | His | Ala | Phe | Glu | Leu | Val |
| 465 | | | | 470 | | | | 475 | | | | | 480 | | |
| Ser | Lys | Asp | Glu | Asn | Ser | Val | Ile | Phe | Ala | Ala | Lys | Ser | Ala | Glu | Glu |
| | | | | 485 | | | | 490 | | | | | 495 | | |
| Lys | Asn | Asn | Trp | Met | Ala | Ala | Leu | Ile | Ser | Leu | His | Tyr | Arg | Ser | Thr |
| | | | 500 | | | | 505 | | | | 510 | | | | |
| Leu | Asp | Arg | Met | Leu | Asp | Ser | Val | Leu | Leu | Lys | Glu | Glu | Asn | Glu | Gln |
| | | 515 | | | | 520 | | | | 525 | | | | | |
| Pro | Leu | Arg | Leu | Pro | Ser | Pro | Asp | Met | Tyr | Arg | Phe | Val | Val | Thr | Asp |
| | 530 | | | | 535 | | | | 540 | | | | | | |
| Ser | Glu | Glu | Asn | Ile | Val | Phe | Glu | Asp | Asn | Leu | Gln | Ser | Arg | Ser | Gly |
| 545 | | | | 550 | | | | 555 | | | | | 560 | | |
| Ile | Pro | Ile | Ile | Lys | Gly | Gly | Thr | Val | Val | Lys | Leu | Ile | Glu | Arg | Leu |
| | | | 565 | | | | 570 | | | | 575 | | | | |
| Thr | Tyr | His | Met | Tyr | Ala | Asp | Pro | Asn | Phe | Val | Arg | Thr | Phe | Leu | Thr |
| | | 580 | | | | 585 | | | | 590 | | | | | |
| Thr | Tyr | Arg | Ser | Phe | Cys | Lys | Pro | Gln | Glu | Leu | Leu | Asn | Leu | Leu | Ile |
| | 595 | | | | 600 | | | | 605 | | | | | | |
| Glu | Arg | Phe | Glu | Ile | Pro | Glu | Pro | Glu | Pro | Thr | Glu | Ala | Asp | Lys | Leu |
| 610 | | | | 615 | | | | 620 | | | | | | | |
| Ala | Leu | Glu | Lys | Gly | Glu | Gln | Pro | Ile | Ser | Ala | Asp | Leu | Lys | Arg | Phe |
| 625 | | | | 630 | | | | 635 | | | | | 640 | | |
| Arg | Lys | Glu | Tyr | Val | Gln | Pro | Val | Gln | Leu | Arg | Val | Leu | Asn | Val | Phe |
| | | | 645 | | | | 650 | | | | 655 | | | | |
| Arg | His | Trp | Val | Glu | His | His | Tyr | Tyr | Asp | Phe | Glu | Arg | Asp | Leu | Glu |

-continued

|   |   |   |   |   | 660 |   |   |   |   | 665 |   |   |   |   | 670 |   |   |
|---|---|---|---|---|---|---|---|---|---|---|---|---|---|---|---|---|---|

Leu Leu Glu Arg Leu Glu Ser Phe Ile Ser Ser Val Arg Gly Lys Ala
            675                 680                 685

Met Lys Lys Trp Val Glu Ser Ile Ala Lys Ile Ile Lys Arg Lys Lys
            690                 695                 700

Gln Ala Gln Ala Asn Gly Ile Ser His Asn Ile Thr Phe Glu Ser Ser
705                 710                 715                 720

Pro Pro Pro Val Glu Trp His Ile Ser Arg Thr Gly Gln Phe Glu Thr
                    725                 730                 735

Phe Asp Leu Met Thr Leu His Pro Ile Glu Ile Ala Arg Gln Leu Thr
                740                 745                 750

Leu Leu Glu Ser Asp Leu Tyr Arg Lys Val Gln Pro Ser Glu Leu Val
            755                 760                 765

Gly Ser Val Trp Thr Lys Glu Asp Lys Glu Ile Asn Ser Pro Asn Leu
            770                 775                 780

Leu Lys Met Ile Arg His Thr Thr Asn Leu Thr Leu Trp Phe Glu Lys
785                 790                 795                 800

Cys Ile Val Glu Ala Glu Asn Phe Glu Glu Arg Val Ala Val Leu Ser
                    805                 810                 815

Arg Ile Val Glu Ile Leu Gln Val Phe Gln Asp Leu Asn Asn Phe Asn
                820                 825                 830

Gly Val Leu Glu Ile Val Ser Ala Val Asn Ser Val Ser Val Tyr Arg
            835                 840                 845

Leu Asp His Thr Phe Glu Ala Leu Gln Glu Arg Lys Arg Arg Ile Leu
            850                 855                 860

Asp Asp Ala Val Glu Leu Ser Gln Asp His Phe Lys Lys Tyr Leu Val
865                 870                 875                 880

Lys Leu Lys Ser Ile Asn Pro Pro Cys Val Pro Phe Phe Gly Ile Tyr
                    885                 890                 895

Leu Thr Asn Ile Leu Lys Thr Glu Glu Gly Asn Ser Asp Phe Leu Lys
                900                 905                 910

Arg Lys Gly Lys Asp Leu Ile Asn Phe Ser Lys Arg Arg Lys Val Ala
            915                 920                 925

Glu Ile Thr Gly Glu Ile Gln Gln Tyr Gln Asn Gln Pro Tyr Cys Leu
            930                 935                 940

Arg Thr Glu Pro Glu Met Arg Arg Phe Phe Glu Asn Leu Asn Pro Met
945                 950                 955                 960

Gly Ile Leu Ser Glu Lys Glu Phe Thr Asp Tyr Leu Phe Asn Lys Ser
                    965                 970                 975

Leu Glu Ile Glu Pro Arg Asn Cys Lys Gln Pro Pro Arg Phe Pro Arg
                980                 985                 990

Lys Ser Thr Phe Ser Leu Lys Ser Pro Gly Ile Arg Pro Asn Ala Gly
            995                 1000                1005

Arg His Gly Ser Thr Ser Gly Thr Leu Arg Gly His Pro Thr Pro Leu
            1010                1015                1020

Glu Arg Glu Pro Tyr Lys Ile Ser Phe Ser Arg Ile Ala Glu Thr Glu
1025                1030                1035                1040

Leu Glu Ser Thr Val Ser Ala Pro Thr Ser Pro Asn Thr Pro Ser Thr
                    1045                1050                1055

Pro Pro Val Ser Ala Ser Ser Asp His Ser Val Phe Leu Asp Val Asp
                1060                1065                1070

Leu Asn Ser Ser Cys Gly Ser Asn Thr Ile Phe Ala Pro Val Leu Leu
            1075                1080                1085

```
Pro His Ser Lys Thr Phe Phe Ser Ser Cys Gly Ser Leu His Lys Leu
    1090                1095                1100
Ser Glu Glu Pro Leu Ile Pro Pro Leu Pro Pro Arg Lys Lys Phe
1105                1110                1115                1120
Asp His Asp Ala Leu Asn Ser Lys Gly Ala Val Lys Ser Asp Asp
                    1125                1130                1135
Pro Pro Ala Ile Pro Pro Arg Gln Pro Pro Pro Lys Val Lys Pro
                1140                1145                1150
Arg Val Pro Val Leu Met Gly Thr Phe Asp Gly Pro Val Pro Ser Pro
            1155                1160                1165
Pro Pro Pro Pro Pro Arg Asp Pro Leu Pro Asp Thr Pro Pro Pro Val
    1170                1175                1180
Pro Leu Arg Pro Pro Glu His Phe Ile Asn Cys Pro Phe Asn Leu Gln
1185                1190                1195                1200
Pro Pro Pro Leu Gly His Pro His Arg Asp Pro Asp Trp Leu Arg Asp
                1205                1210                1215
Val Ser Thr Cys Pro Asn Ser Pro Ser Thr Pro Pro Thr Thr Pro Ser
                1220                1225                1230
Pro Arg Ile Pro Arg Ser Cys His Leu Leu Ser Ser Ser His Ser Ser
            1235                1240                1245
Leu Ala His Leu Pro Ala Pro Pro Val Pro Pro Arg Gln Asn Ser Ser
    1250                1255                1260
Pro Leu Leu Pro Lys Leu Pro Pro Lys Thr Tyr Lys Arg Glu Leu Ser
1265                1270                1275                1280
His Pro Pro Leu Tyr Arg Leu Pro Leu Leu Glu Asn Ala Glu Thr Pro
                1285                1290                1295
Gln
```

( 2 ) INFORMATION FOR SEQ ID NO:5:

( i ) SEQUENCE CHARACTERISTICS:
        ( A ) LENGTH: 1572 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Phe Ser Gly Pro Ser Gly His Ala His Thr Ile Ser Tyr Gly Gly
 1               5                  10                  15
Gly Ile Gly Leu Gly Thr Gly Gly Gly Gly Ser Gly Gly Ser Gly
            20                  25                  30
Ser Gly Ser Gln Gly Gly Gly Gly Ile Gly Ile Gly Gly Gly Gly
        35                  40                  45
Val Ala Gly Leu Gln Asp Cys Asp Gly Tyr Asp Phe Thr Lys Cys Glu
    50                  55                  60
Asn Ala Ala Arg Trp Arg Gly Leu Phe Thr Pro Ser Leu Lys Lys Val
65                  70                  75                  80
Leu Glu Gln Val His Pro Arg Val Thr Ala Lys Glu Asp Ala Leu Leu
                85                  90                  95
Tyr Val Glu Lys Leu Cys Leu Arg Leu Leu Ala Met Leu Cys Ala Lys
                100                 105                 110
Pro Leu Pro His Ser Val Gln Asp Val Glu Glu Lys Val Asn Lys Ser
                115                 120                 125
Phe Pro Ala Pro Ile Asp Gln Trp Ala Leu Asn Glu Ala Lys Glu Val
                130                 135                 140
```

```
Ile  Asn  Ser  Lys  Lys  Arg  Lys  Ser  Val  Leu  Pro  Thr  Glu  Lys  Val  His
145                 150                      155                      160

Thr  Leu  Leu  Gln  Lys  Asp  Val  Leu  Gln  Tyr  Lys  Ile  Asp  Ser  Ser  Val
                165                     170                     175

Ser  Ala  Phe  Leu  Val  Ala  Val  Leu  Tyr  Ile  Ser  Ala  Asp  Ile  Leu
               180                180                     190

Lys  Met  Ala  Gly  Asp  Tyr  Val  Ile  Lys  Ile  Ala  His  Cys  Glu  Ile  Thr
               195                     200                205

Lys  Glu  Asp  Ile  Glu  Val  Val  Met  Asn  Ala  Asp  Arg  Val  Leu  Met  Asp
     210                      215                     220

Met  Leu  Asn  Gln  Ser  Glu  Ala  His  Ile  Leu  Pro  Ser  Pro  Leu  Ser  Leu
225                      230                      235                     240

Pro  Ala  Gln  Arg  Ala  Ser  Ala  Thr  Tyr  Glu  Glu  Thr  Val  Lys  Glu  Leu
                245                      250                     255

Ile  His  Asp  Glu  Lys  Gln  Tyr  Gln  Arg  Asp  Leu  His  Met  Ile  Ile  Arg
               260                     265                     270

Val  Phe  Arg  Glu  Glu  Leu  Val  Lys  Ile  Val  Ser  Asp  Pro  Arg  Glu  Leu
          275                     280                     285

Glu  Pro  Ile  Phe  Ser  Asn  Ile  Met  Asp  Ile  Tyr  Glu  Val  Thr  Val  Thr
     290                     295                     300

Leu  Leu  Gly  Ser  Leu  Glu  Asp  Val  Ile  Glu  Met  Ser  Gln  Glu  Gln  Ser
305                      310                     315                     320

Ala  Pro  Cys  Val  Gly  Ser  Cys  Phe  Glu  Glu  Leu  Ala  Glu  Ala  Glu  Glu
               325                     330                          335

Phe  Asp  Val  Tyr  Lys  Lys  Tyr  Ala  Tyr  Asp  Val  Thr  Ser  Gln  Ala  Ser
               340                     345                     350

Arg  Asp  Ala  Leu  Asn  Asn  Leu  Leu  Ser  Lys  Pro  Gly  Ala  Ser  Ser  Leu
          355                     360                     365

Thr  Thr  Ala  Gly  His  Gly  Phe  Arg  Asp  Ala  Val  Lys  Tyr  Tyr  Leu  Pro
370                      375                     380

Lys  Leu  Leu  Leu  Val  Pro  Ile  Cys  His  Ala  Phe  Val  Tyr  Phe  Asp  Tyr
385                      390                     395                     400

Ile  Lys  His  Leu  Lys  Asp  Leu  Ser  Ser  Ser  Gln  Asp  Asp  Ile  Glu  Ser
                405                     410                     415

Phe  Glu  Gln  Val  Gln  Gly  Leu  Leu  His  Pro  Leu  His  Cys  Asp  Leu  Glu
               420                     425                     430

Lys  Val  Met  Ala  Ser  Leu  Ser  Lys  Glu  Arg  Gln  Val  Pro  Val  Ser  Gly
          435                     440                     445

Arg  Val  Arg  Arg  Gln  Leu  Ala  Ile  Glu  Arg  Thr  Arg  Glu  Leu  Gln  Met
     450                     455                     460

Lys  Val  Glu  His  Trp  Glu  Asp  Lys  Asp  Val  Gly  Gln  Asn  Cys  Asn  Glu
465                      470                     475                     480

Phe  Ile  Arg  Glu  Asp  Ser  Leu  Ser  Lys  Leu  Gly  Ser  Gly  Lys  Arg  Ile
               485                     490                     495

Trp  Ser  Glu  Arg  Lys  Val  Phe  Leu  Phe  Asp  Gly  Leu  Met  Val  Leu  Cys
               500                     505                     510

Lys  Ala  Asn  Thr  Lys  Lys  Gln  Thr  Pro  Ser  Ala  Gly  Ala  Thr  Ala  Tyr
               515                     520                     525

Asp  Tyr  Arg  Leu  Lys  Glu  Lys  Tyr  Phe  Met  Arg  Arg  Val  Asp  Ile  Asn
     530                     535                     540

Asp  Arg  Pro  Asp  Ser  Asp  Leu  Lys  Asn  Ser  Phe  Glu  Leu  Ala  Pro
545                     550                     555                     560

Arg  Met  Gln  Pro  Pro  Ile  Val  Leu  Thr  Ala  Lys  Asn  Ala  Gln  His  Lys
               565                     570                     575
```

-continued

```
His  Asp  Trp  Met  Ala  Asp  Leu  Leu  Met  Val  Ile  Thr  Lys  Ser  Met  Leu
               580                 585                          590

Asp  Arg  His  Leu  Asp  Ser  Ile  Leu  Gln  Asp  Ile  Glu  Arg  Lys  His  Pro
          595                 600                      605

Leu  Arg  Met  Pro  Ser  Pro  Glu  Ile  Tyr  Lys  Phe  Ala  Val  Pro  Asp  Ser
          610                 615                      620

Gly  Asp  Asn  Ile  Val  Leu  Glu  Glu  Arg  Glu  Ser  Ala  Gly  Val  Pro  Met
625                           630                 635                      640

Ile  Lys  Gly  Ala  Thr  Leu  Cys  Lys  Leu  Ile  Glu  Arg  Leu  Thr  Tyr  His
                    645                      650                     655

Ile  Tyr  Ala  Asp  Pro  Thr  Phe  Val  Arg  Thr  Phe  Leu  Thr  Thr  Tyr  Arg
               660                      665                     670

Tyr  Phe  Cys  Ser  Pro  Gln  Gln  Leu  Leu  Gln  Leu  Leu  Val  Glu  Arg  Phe
               675                 680                     685

Asn  Ile  Pro  Asp  Pro  Ser  Leu  Val  Tyr  Gln  Asp  Thr  Gly  Thr  Ala  Gly
          690                 695                      700

Ala  Gly  Gly  Met  Gly  Gly  Val  Gly  Gly  Asp  Lys  Glu  His  Lys  Asn  Ser
705                      710                 715                          720

His  Arg  Glu  Asp  Trp  Lys  Arg  Tyr  Arg  Lys  Glu  Tyr  Val  Gln  Pro  Val
                    725                 730                          735

Gln  Phe  Arg  Val  Leu  Asn  Val  Leu  Arg  His  Trp  Val  Asp  His  His  Phe
               740                      745                     750

Tyr  Asp  Phe  Glu  Lys  Asp  Pro  Met  Leu  Leu  Glu  Lys  Leu  Leu  Asn  Phe
               755                 760                      765

Leu  Glu  His  Val  Asn  Gly  Lys  Ser  Met  Arg  Lys  Trp  Val  Asp  Ser  Val
          770                 775                      780

Leu  Lys  Ile  Val  Gln  Arg  Lys  Asn  Glu  Gln  Glu  Lys  Ser  Asn  Lys  Lys
785                      790                 795                          800

Ile  Val  Tyr  Ala  Tyr  Gly  His  Asp  Pro  Pro  Ile  Glu  His  His  Leu
               805                 810                      815

Ser  Val  Pro  Asn  Asp  Glu  Ile  Thr  Leu  Leu  Thr  Leu  His  Pro  Leu  Glu
               820                 825                      830

Leu  Ala  Arg  Gln  Leu  Thr  Leu  Leu  Glu  Phe  Glu  Met  Tyr  Lys  Asn  Val
          835                      840                     845

Lys  Pro  Ser  Glu  Leu  Val  Gly  Ser  Pro  Trp  Thr  Lys  Asp  Lys  Glu
     850                      855                      860

Val  Lys  Ser  Pro  Asn  Leu  Leu  Lys  Ile  Met  Lys  His  Thr  Thr  Asn  Val
865                           870                 875                      880

Thr  Arg  Trp  Ile  Glu  Lys  Ser  Ile  Thr  Glu  Ala  Glu  Asn  Tyr  Glu  Glu
                    885                 890                          895

Arg  Leu  Ala  Ile  Met  Gln  Arg  Ala  Ile  Glu  Val  Met  Met  Val  Met  Leu
               900                 905                      910

Glu  Leu  Asn  Asn  Phe  Asn  Gly  Ile  Leu  Ser  Ile  Val  Ala  Ala  Met  Gly
          915                 920                      925

Thr  Ala  Ser  Val  Tyr  Arg  Leu  Arg  Trp  Thr  Phe  Gln  Gly  Leu  Pro  Glu
     930                      935                 940

Arg  Tyr  Arg  Lys  Phe  Leu  Glu  Glu  Cys  Arg  Glu  Leu  Ser  Asp  Asp  His
945                      950                 955                          960

Leu  Lys  Lys  Tyr  Gln  Glu  Arg  Leu  Arg  Ser  Ile  Asn  Pro  Pro  Cys  Val
                    965                 970                          975

Pro  Phe  Phe  Gly  Arg  Tyr  Leu  Thr  Asn  Ile  Leu  His  Leu  Glu  Glu  Gly
                    980                 985                      990

Asn  Pro  Asp  Leu  Leu  Ala  Asn  Thr  Glu  Leu  Ile  Asn  Phe  Ser  Lys  Arg
```

-continued

```
                  995                  1000                 1005
Arg  Lys  Val  Ala  Glu  Ile  Ile  Gly  Glu  Ile  Gln  Gln  Tyr  Gln  Asn  Gln
     1010                    1015                    1020
Pro  Tyr  Cys  Leu  Asn  Glu  Glu  Ser  Thr  Ile  Arg  Gln  Phe  Phe  Glu  Gln
1025                     1030                    1035                     1040
Leu  Asp  Pro  Phe  Asn  Gly  Leu  Ser  Asp  Lys  Gln  Met  Ser  Asp  Tyr  Leu
               1045                    1050                    1055
Tyr  Asn  Glu  Ser  Leu  Arg  Ile  Glu  Pro  Arg  Gly  Cys  Lys  Thr  Val  Pro
          1060                    1065                    1070
Lys  Phe  Pro  Arg  Lys  Trp  Pro  His  Ile  Pro  Leu  Lys  Ser  Pro  Gly  Ile
     1075                    1080                    1085
Lys  Pro  Arg  Arg  Gln  Asn  Gln  Thr  Asn  Ser  Ser  Ser  Lys  Leu  Ser  Asn
1090                     1095                    1100
Ser  Thr  Ser  Ser  Val  Ala  Ala  Ala  Ala  Ala  Ser  Ser  Thr  Ala  Thr
1105                     1110                    1115                     1120
Ser  Ile  Ala  Thr  Ala  Ser  Ala  Pro  Ser  Leu  His  Ala  Ser  Ser  Ile  Met
               1125                    1130                    1135
Asp  Ala  Pro  Thr  Ala  Ala  Ala  Ala  Asn  Ala  Gly  Ser  Gly  Thr  Leu  Ala
               1140                    1145                    1150
Gly  Glu  Gln  Ser  Pro  Gln  His  Asn  Pro  His  Ala  Phe  Ser  Val  Phe  Ala
               1155                    1160                    1165
Pro  Val  Ile  Ile  Pro  Glu  Arg  Asn  Thr  Ser  Ser  Trp  Ser  Gly  Thr  Pro
     1170                    1175                    1180
Gln  His  Thr  Arg  Thr  Asp  Gln  Asn  Asn  Gly  Glu  Val  Ser  Val  Pro  Ala
1185                     1190                    1195                     1200
Pro  His  Leu  Pro  Lys  Lys  Pro  Gly  Ala  His  Val  Trp  Ala  Asn  Asn  Asn
               1205                    1210                    1215
Ser  Thr  Leu  Ala  Ser  Ala  Ser  Ala  Met  Asp  Val  Val  Phe  Ser  Pro  Ala
               1220                    1225                    1230
Leu  Pro  Glu  His  Leu  Pro  Pro  Gln  Ser  Leu  Pro  Asp  Ser  Asn  Pro  Phe
               1235                    1240                    1245
Ala  Ser  Asp  Thr  Glu  Ala  Pro  Pro  Ser  Pro  Leu  Pro  Lys  Leu  Val  Val
               1250                    1255                    1260
Ser  Pro  Arg  His  Glu  Thr  Gly  Asn  Arg  Ser  Pro  Phe  His  Gly  Arg  Met
1265                     1270                    1275                     1280
Gln  Asn  Ser  Pro  Thr  His  Ser  Thr  Ala  Ser  Thr  Val  Thr  Leu  Thr  Gly
                    1285                    1290                    1295
Met  Ser  Thr  Ser  Gly  Gly  Glu  Glu  Phe  Cys  Ala  Gly  Gly  Phe  Tyr  Phe
               1300                    1305                    1310
Asn  Ser  Ala  His  Gln  Gly  Gln  Pro  Gly  Ala  Val  Pro  Ile  Ser  Pro  His
               1315                    1320                    1325
Val  Asn  Val  Pro  Met  Ala  Thr  Asn  Met  Glu  Tyr  Arg  Ala  Val  Pro  Pro
               1330                    1335                    1340
Pro  Leu  Pro  Pro  Arg  Arg  Lys  Glu  Arg  Thr  Glu  Ser  Cys  Ala  Asp  Met
1345                     1350                    1355                     1360
Ala  Gln  Lys  Arg  Gln  Ala  Pro  Asp  Ala  Pro  Thr  Leu  Pro  Pro  Arg  Asp
                    1365                    1370                    1375
Gly  Glu  Leu  Ser  Pro  Pro  Pro  Ile  Pro  Pro  Arg  Leu  Asn  His  Ser  Thr
               1380                    1385                    1390
Gly  Ile  Ser  Tyr  Leu  Arg  Gln  Ser  His  Gly  Lys  Ser  Lys  Glu  Phe  Val
               1395                    1400                    1405
Gly  Asn  Ser  Ser  Leu  Leu  Leu  Pro  Asn  Thr  Ser  Ser  Ile  Met  Ile  Arg
               1410                    1415                    1420
```

```
Arg  Asn  Ser  Ala  Ile  Glu  Lys  Arg  Ala  Ala  Ala  Thr  Ser  Gln  Pro  Asn
1425                1430                1435                          1440

Gln  Ala  Ala  Ala  Gly  Pro  Ile  Ser  Thr  Thr  Leu  Val  Thr  Val  Ser  Gln
               1445                1450                          1455

Ala  Val  Ala  Thr  Asp  Glu  Pro  Leu  Ala  Thr  Asp  Leu  Ala  Ser  Gly
          1460                     1465                1470

Lys  Leu  Leu  Asp  Asp  His  Ile  Thr  Ala  Asp  Thr  Arg  His  Val  Ala  His
               1475                1480                          1585

Val  Ser  Gln  His  Ser  Gln  Pro  Ser  Gly  Gly  Glu  His  Val  Glu  Gln  Leu
1490                     1495                     1500

Cys  Pro  Pro  Thr  Ala  Asn  Ala  Ala  Ala  Ala  Ala  Ala  Ala  Asp  Ala  Ser
1505                     1510                     1515                     1520

Ser  Asp  Leu  Leu  Ala  Ala  Pro  Ser  Thr  Ser  Cys  His  Pro  Ser  Ala  Ala
                    1525                     1530                     1535

Pro  Ser  Ala  Pro  Ala  Pro  Phe  Glu  Ser  Asp  Ala  Val  Ala  Leu  Val  Pro
               1540                     1545                     1550

Gln  Gly  Val  Leu  Ser  Asp  Cys  His  Glu  Pro  Arg  Gly  His  Thr  Gln  Thr
               1555                     1560                     1565

Ser  Thr  Lys  Thr
               1570
```

( 2 ) INFORMATION FOR SEQ ID NO:6:

( i ) SEQUENCE CHARACTERISTICS:
        ( A ) LENGTH: 1336 amino acids
        ( B ) TYPE: amino acids
        ( D ) TOPOLOGY: linear ( i i ) MOLECULE TYPE: protein ( x i ) SEQUENCE DESCRIPTION: SEQ ID NO:6:

```
Met  Leu  Val  Ser  His  Leu  Ile  Leu  Pro  Lys  Lys  Gln  His  Pro  Ala  Gly
1                   5                    10                            15

Thr  Met  Gln  Ala  Gln  Gln  Leu  Pro  Tyr  Glu  Phe  Phe  Ser  Glu  Glu  Asn
               20                     25                          30

Ala  Pro  Lys  Trp  Arg  Gly  Leu  Leu  Val  Pro  Ala  Leu  Lys  Lys  Val  Gln
          35                      40                           45

Gly  Gln  Val  His  Pro  Thr  Leu  Glu  Ser  Asn  Asp  Ala  Leu  Gln  Tyr
     50                       55                      60

Val  Glu  Glu  Leu  Ile  Leu  Gln  Leu  Leu  Asn  Met  Leu  Cys  Gln  Ala  Gln
65                       70                      75                       80

Pro  Arg  Ser  Ala  Ser  Asp  Val  Glu  Glu  Arg  Val  Gln  Lys  Ser  Phe  Pro
                    85                      90                           95

His  Pro  Ile  Asp  Lys  Trp  Ala  Ile  Ala  Asp  Ala  Gln  Ser  Ala  Ile  Glu
               100                     105                      110

Lys  Arg  Lys  Arg  Arg  Asn  Pro  Leu  Ser  Leu  Pro  Ala  Glu  Arg  Ile  His
          115                     120                      125

His  Leu  Leu  Arg  Glu  Val  Leu  Gly  Tyr  Lys  Ile  Asp  His  Gln  Val  Ser
     130                     135                      140

Val  Tyr  Ile  Val  Ala  Val  Leu  Glu  Tyr  Ile  Ser  Ala  Asp  Ile  Leu  Lys
145                      150                      155                      160

Leu  Val  Gly  Asn  Tyr  Val  Arg  Asn  Ile  Arg  His  Tyr  Glu  Ile  Thr  Lys
                    165                     170                      175

Gln  Asp  Ile  Lys  Val  Ala  Met  Cys  Ala  Asp  Lys  Val  Leu  Met  Asp  Met
               180                     185                      190

Phe  His  Gln  Asp  Val  Glu  Asp  Ile  Asn  Ile  Leu  Ser  Leu  Thr  Asp  Glu
          195                     200                      205
```

```
Glu  Pro  Ser  Thr  Ser  Gly  Glu  Gln  Thr  Tyr  Tyr  Asp  Leu  Val  Lys  Ala
     210                 215                 220

Phe  Met  Ala  Glu  Ile  Arg  Gln  Tyr  Ile  Arg  Glu  Leu  Asn  Leu  Ile  Ile
225                 230                 235                                 240

Lys  Val  Phe  Arg  Glu  Pro  Phe  Val  Ser  Asn  Ser  Lys  Leu  Phe  Ser  Ser
                    245                 250                           255

Asn  Asp  Val  Glu  Asn  Ile  Phe  Ser  Arg  Ile  Val  Asp  Ile  His  Glu  Leu
               260                 265                      270

Ser  Val  Lys  Leu  Leu  Gly  His  Ile  Glu  Asp  Thr  Val  Glu  Met  Thr  Asp
          275                 280                 285

Glu  Gly  Ser  Pro  His  Pro  Leu  Val  Gly  Ser  Cys  Phe  Glu  Asp  Leu  Ala
     290                 295                 300

Glu  Glu  Leu  Ala  Phe  Asp  Pro  Tyr  Glu  Ser  Tyr  Ala  Arg  Asp  Ile  Leu
305                 310                 315                                 320

Arg  Pro  Gly  Phe  His  Gly  His  Phe  Leu  Ser  Gln  Leu  Ser  Lys  Pro  Gly
                    325                 330                           335

Ala  Ala  Leu  Tyr  Leu  Gln  Ser  Ile  Gly  Glu  Gly  Phe  Lys  Glu  Ala  Val
               340                 345                      350

Gln  Tyr  Val  Leu  Pro  Arg  Leu  Leu  Leu  Ala  Pro  Val  Tyr  His  Cys  Leu
          355                 360                 365

His  Tyr  Phe  Glu  Leu  Leu  Lys  Gln  Leu  Glu  Glu  Lys  Ser  Glu  Asp  Gln
     370                 375                 380

Glu  Asp  Lys  Glu  Cys  Met  Lys  Gln  Ala  Ile  Thr  Ala  Leu  Leu  Asn  Val
385                 390                 395                                 400

Gln  Ser  Gly  Met  Glu  Lys  Ile  Cys  Ser  Lys  Ser  Leu  Ala  Lys  Arg  Arg
                    405                 410                           415

Leu  Ser  Glu  Ser  Ala  Cys  Arg  Phe  Tyr  Ser  Gln  Met  Lys  Gly  Lys
               420                 425                      430

Gln  Leu  Ala  Ile  Lys  Lys  Met  Asn  Glu  Ile  Gln  Lys  Asn  Ile  Asp  Gly
          435                 440                 445

Trp  Glu  Gly  Lys  Asp  Ile  Gly  Gln  Cys  Cys  Asn  Glu  Phe  Ile  Met  Glu
     450                 455                 460

Gly  Thr  Leu  Thr  Arg  Val  Gly  Ala  Lys  His  Glu  Arg  His  Ile  Phe  Leu
465                 470                 475                                 480

Phe  Asp  Gly  Leu  Met  Ile  Cys  Cys  Lys  Ser  Asn  His  Gly  Gln  Pro  Arg
                    485                 490                           495

Leu  Pro  Gly  Ala  Ser  Ser  Ala  Glu  Tyr  Arg  Leu  Lys  Glu  Lys  Phe  Phe
               500                 505                      510

Met  Arg  Lys  Val  Gln  Ile  Asn  Asp  Lys  Asp  Asp  Thr  Ser  Glu  Tyr  Lys
          515                 520                 525

His  Ala  Phe  Glu  Ile  Ile  Leu  Lys  Asp  Gly  Asn  Ser  Val  Ile  Phe  Ser
     530                 535                 540

Ala  Lys  Ser  Ala  Glu  Glu  Lys  Asn  Asn  Trp  Met  Ala  Ala  Leu  Ile  Ser
545                 550                 555                                 560

Leu  Gln  Tyr  Arg  Ser  Thr  Leu  Glu  Arg  Met  Leu  Asp  Val  Thr  Val  Leu
                    565                 570                           575

Gln  Glu  Glu  Lys  Glu  Glu  Gln  Met  Arg  Leu  Pro  Ser  Ala  Glu  Val  Tyr
               580                 585                      590

Arg  Phe  Ala  Glu  Pro  Asp  Ser  Glu  Asn  Ile  Leu  Phe  Glu  Glu  Asn
          595                 600                 605

Val  Gln  Pro  Lys  Ala  Gly  Ile  Pro  Ile  Ile  Lys  Ala  Gly  Thr  Val  Leu
     610                 615                 620

Lys  Leu  Ile  Glu  Arg  Leu  Thr  Tyr  His  Met  Tyr  Ala  Asp  Pro  Asn  Phe
```

```
625                    630                    635                    640
Val  Arg  Thr  Phe  Leu  Thr  Thr  Tyr  Arg  Ser  Phe  Cys  Arg  Pro  Gln  Glu
                    645                    650                    655

Leu  Leu  Ser  Leu  Leu  Ile  Glu  Arg  Phe  Glu  Ile  Pro  Glu  Pro  Glu  Pro
                    660                    665                    670

Thr  Glu  Ala  Asp  Arg  Ile  Ala  Ile  Glu  Asn  Gly  Asp  Gln  Pro  Leu  Ser
                    675                    680                    685

Ala  Glu  Leu  Lys  Arg  Phe  Arg  Lys  Glu  Tyr  Ile  Gln  Pro  Val  Gln  Leu
          690                    695                    700

Arg  Val  Leu  Asn  Val  Cys  Arg  His  Trp  Val  Glu  His  His  Phe  Tyr  Asp
705                    710                    715                    720

Phe  Glu  Arg  Asp  Ala  Asp  Leu  Leu  Gln  Arg  Met  Glu  Glu  Phe  Ile  Gly
                    725                    730                    735

Thr  Val  Arg  Gly  Lys  Ala  Met  Lys  Lys  Trp  Val  Glu  Ser  Ile  Thr  Lys
               740                    745                    750

Ile  Ile  Gln  Arg  Lys  Lys  Ile  Ala  Arg  Asp  Asn  Gly  Pro  Gly  His  Asn
          755                    760                    765

Ile  Thr  Phe  Gln  Ser  Ser  Pro  Thr  Val  Glu  Trp  His  Ile  Ser  Arg
     770                    775                    780

Pro  Gly  His  Ile  Glu  Thr  Phe  Asp  Leu  Leu  Thr  Leu  His  Pro  Ile  Glu
785                    790                    795                    800

Ile  Ala  Arg  Gln  Leu  Thr  Leu  Leu  Glu  Ser  Asp  Leu  Tyr  Arg  Ala  Val
                    805                    810                    815

Gln  Pro  Ser  Glu  Leu  Val  Gly  Ser  Val  Trp  Thr  Lys  Glu  Asp  Lys  Glu
               820                    825                    830

Ile  Asn  Ser  Pro  Asn  Leu  Leu  Lys  Met  Ile  Arg  His  Thr  Thr  Asn  Leu
          835                    840                    845

Thr  Leu  Trp  Phe  Glu  Lys  Cys  Ile  Val  Glu  Thr  Glu  Asn  Leu  Glu  Glu
     850                    855                    860

Arg  Val  Ala  Val  Val  Ser  Arg  Ile  Ile  Glu  Ile  Leu  Gln  Val  Phe  Gln
865                    870                    875                    880

Glu  Leu  Asn  Asn  Phe  Asn  Gly  Val  Leu  Glu  Val  Val  Ser  Ala  Met  Asn
                    885                    890                    895

Ser  Ser  Pro  Val  Tyr  Arg  Leu  Asp  His  Thr  Phe  Glu  Gln  Ile  Pro  Ser
               900                    905                    910

Arg  Gln  Lys  Lys  Ile  Leu  Glu  Glu  Ala  His  Glu  Leu  Ser  Glu  Asp  His
          915                    920                    925

Tyr  Lys  Lys  Tyr  Leu  Ala  Lys  Leu  Arg  Ser  Ile  Asn  Pro  Pro  Cys  Val
     930                    935                    940

Pro  Phe  Phe  Gly  Ile  Tyr  Leu  Thr  Asn  Ile  Leu  Lys  Thr  Glu  Glu  Gly
945                    950                    955                    960

Asn  Pro  Glu  Val  Leu  Arg  Arg  His  Gly  Lys  Glu  Leu  Ile  Asn  Phe  Ser
                    965                    970                    975

Lys  Arg  Arg  Arg  Val  Ala  Glu  Ile  Thr  Gly  Glu  Ile  Gln  Gln  Tyr  Gln
               980                    985                    990

Asn  Gln  Pro  Tyr  Cys  Leu  Arg  Val  Glu  Pro  Asp  Ile  Lys  Arg  Phe  Phe
          995                    1000                   1005

Glu  Asn  Leu  Asn  Pro  Met  Gly  Asn  Ser  Met  Glu  Lys  Glu  Phe  Thr  Asp
     1010                   1015                   1020

Tyr  Leu  Phe  Asn  Lys  Ser  Leu  Glu  Ile  Glu  Pro  Arg  His  Pro  Lys  Pro
1025                   1030                   1035                   1040

Leu  Pro  Arg  Phe  Pro  Lys  Lys  Tyr  Ser  Tyr  Pro  Leu  Lys  Ser  Pro  Gly
                    1045                   1050                   1055
```

```
Val  Arg  Pro  Ser  Asn  Pro  Arg  Pro  Gly  Thr  Met  Arg  His  Pro  Thr  Pro
               1060               1065                    1070

Leu  Gln  Gln  Glu  Pro  Arg  Lys  Ile  Ser  Tyr  Ser  Arg  Ile  Pro  Glu  Ser
               1075               1080                    1085

Glu  Thr  Glu  Ser  Thr  Ala  Ser  Ala  Pro  Asn  Ser  Pro  Arg  Thr  Pro  Leu
1090                         1095                    1100

Thr  Pro  Pro  Pro  Ala  Ser  Gly  Thr  Ser  Ser  Asn  Thr  Asp  Val  Cys  Ser
1105                         1110                    1115                    1120

Val  Phe  Asp  Ser  Asp  His  Ser  Ala  Ser  Pro  Phe  His  Ser  Arg  Ser  Ala
               1125               1130                    1135

Ser  Val  Ser  Ser  Ile  Ser  Leu  Ser  Lys  Gly  Thr  Asp  Glu  Val  Pro  Val
               1140               1145                    1150

Pro  Pro  Pro  Val  Pro  Pro  Arg  Arg  Arg  Pro  Glu  Ser  Ala  Pro  Ala  Glu
               1155               1160                    1165

Ser  Ser  Pro  Ser  Lys  Ile  Met  Ser  Lys  His  Leu  Asp  Ser  Pro  Pro  Ala
               1170               1175                    1180

Ile  Pro  Pro  Arg  Gln  Pro  Thr  Ser  Lys  Ala  Tyr  Ser  Pro  Arg  Tyr  Ser
1185                         1190                    1195                    1200

Ile  Ser  Asp  Arg  Thr  Ser  Ile  Ser  Asp  Pro  Pro  Glu  Ser  Pro  Pro  Leu
               1205               1210                    1215

Leu  Pro  Pro  Arg  Glu  Pro  Val  Arg  Thr  Pro  Asp  Val  Phe  Ser  Ser  Ser
               1220               1225                    1230

Pro  Leu  His  Leu  Gln  Pro  Pro  Leu  Gly  Lys  Lys  Ser  Asp  His  Gly
               1235               1240                    1245

Asn  Ala  Phe  Phe  Pro  Asn  Ser  Pro  Ser  Pro  Phe  Thr  Pro  Pro  Pro  Pro
1250                         1255                    1260

Gln  Thr  Pro  Ser  Pro  His  Gly  Thr  Arg  Arg  His  Leu  Pro  Ser  Pro  Pro
1265                         1270                    1275                    1280

Leu  Thr  Gln  Glu  Met  Asp  Leu  His  Ser  Ile  Ala  Gly  Pro  Pro  Val  Pro
                    1285               1290                    1295

Pro  Arg  Gln  Ser  Thr  Ser  Gln  Leu  Ile  Pro  Lys  Leu  Pro  Pro  Lys  Thr
               1300               1305                    1310

Tyr  Lys  Arg  Glu  His  Thr  His  Pro  Ser  Met  His  Arg  Asp  Gly  Pro  Pro
               1315               1320                    1325

Leu  Leu  Glu  Asn  Ala  His  Ser  Ser
     1330                    1335
```

( 2 ) INFORMATION FOR SEQ ID NO:7:

( i ) SEQUENCE CHARACTERISTICS:
    ( A ) LENGTH: 108 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:7:

```
TGT  GTT  CTA  GTT  GGG  TGC  AAG  GTC  TAG  CCT  AAG  GCA  ATG  CTT  GTC  TCC        48
Cys  Val  Leu  Val  Gly  Cys  Lys  Val       Pro  Lys  Ala  Met  Leu  Val  Ser
1                   5                        10                       15

CAC  CTC  ATC  CTG  CCA  AGG  AAG  CAG  CAC  CCC  GCG  GGC  ACC  ATG  CAG  GCG        96
His  Leu  Ile  Leu  Pro  Arg  Lys  Gln  His  Pro  Ala  Gly  Thr  Met  Gln  Ala
                    20                       25                       30

CAG  CAG  CTG  CCT                                                                   108
Gln  Gln  Leu  Pro
          35
```

(2) INFORMATION FOR SEQ ID NO:8:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

```
GCC  CCT  CCG  CCC  GCC  CCG  AGG  CGC  CCC  GCG  GGC  ACC  ATG  CAG  GCG  CAG    48
Ala  Pro  Pro  Pro  Ala  Pro  Arg  Arg  Pro  Ala  Gly  Thr  Met  Gln  Ala  Gln
 1               5                        10                       15

CAG  CTG  CCT                                                                      57
Gln  Leu  Pro
```

(2) INFORMATION FOR SEQ ID NO:9:

(i) SEQUENCE CHARACTERISTICS:
        (A) LENGTH: 430 amino acids
        (B) TYPE: amino acids
        (D) TOPOLOGY: linear (ii) MOLECULE TYPE: protein (xi) SEQUENCE DESCRIPTION: SEQ ID NO:9:

```
Ile  Lys  Gly  Ala  Thr  Leu  Cys  Lys  Leu  Ile  Glu  Arg  Leu  Thr  Tyr  His
 1               5                        10                       15

Ile  Tyr  Ala  Asp  Pro  Thr  Phe  Val  Arg  Thr  Phe  Leu  Thr  Thr  Tyr  Arg
               20                        25                       30

Tyr  Phe  Cys  Ser  Pro  Gln  Gln  Leu  Leu  Gln  Leu  Leu  Val  Glu  Arg  Phe
               35                        40                       45

Asn  Ile  Pro  Asp  Pro  Ser  Leu  Val  Tyr  Gln  Asp  Thr  Gly  Thr  Ala  Gly
         50                        55                       60

Ala  Gly  Gly  Met  Gly  Gly  Val  Gly  Gly  Asp  Lys  Glu  His  Lys  Asn  Ser
 65                       70                        75                       80

His  Arg  Glu  Asp  Trp  Lys  Arg  Tyr  Arg  Lys  Glu  Tyr  Val  Gln  Pro  Val
                         85                        90                       95

Gln  Phe  Arg  Val  Leu  Asn  Val  Leu  Arg  His  Trp  Val  Asp  His  His  Phe
                        100                       105                      110

Tyr  Asp  Phe  Glu  Lys  Asp  Pro  Met  Leu  Leu  Glu  Lys  Leu  Leu  Asn  Phe
                        115                       120                      125

Leu  Glu  His  Val  Asn  Gly  Lys  Ser  Met  Arg  Lys  Trp  Val  Asp  Ser  Val
     130                       135                       140

Leu  Lys  Ile  Val  Gln  Arg  Lys  Asn  Glu  Gln  Glu  Lys  Ser  Asn  Lys  Lys
145                            150                       155                      160

Ile  Val  Tyr  Ala  Tyr  Gly  His  Asp  Pro  Pro  Ile  Glu  His  His  Leu
                        165                       170                      175

Ser  Val  Pro  Asn  Asp  Glu  Ile  Thr  Leu  Leu  Thr  Leu  His  Pro  Leu  Glu
                   180                       185                      190

Leu  Ala  Arg  Gln  Leu  Thr  Leu  Leu  Glu  Phe  Glu  Met  Tyr  Lys  Asn  Val
               195                       200                      205

Lys  Pro  Ser  Glu  Leu  Val  Gly  Ser  Pro  Trp  Thr  Lys  Lys  Asp  Lys  Glu
     210                       215                       220

Val  Lys  Ser  Pro  Asn  Leu  Leu  Lys  Ile  Met  Lys  His  Thr  Thr  Asn  Val
225                       230                       235                      240

Thr  Arg  Trp  Ile  Glu  Lys  Ser  Ile  Thr  Glu  Ala  Glu  Asn  Tyr  Glu  Glu
                    245                       250                      255

Arg  Leu  Ala  Ile  Met  Gln  Arg  Ala  Ile  Glu  Val  Met  Met  Val  Met  Leu
```

|     |     |     |     |     | 260 |     |     |     |     | 265 |     |     |     |     | 270 |     |     |
| --- | --- | --- | --- | --- | --- | --- | --- | --- | --- | --- | --- | --- | --- | --- | --- | --- | --- |
| Glu | Leu | Asn | Asn | Phe | Asn | Gly | Ile | Leu | Ser | Ile | Val | Ala | Ala | Met | Gly |
|     |     | 275 |     |     |     |     | 280 |     |     |     |     | 285 |     |     |     |
| Thr | Ala | Ser | Val | Tyr | Arg | Leu | Arg | Trp | Thr | Phe | Gln | Gly | Leu | Pro | Glu |
|     | 290 |     |     |     | 295 |     |     |     |     | 300 |     |     |     |     |     |
| Arg | Tyr | Arg | Lys | Phe | Leu | Glu | Glu | Cys | Arg | Glu | Leu | Ser | Asp | Asp | His |
| 305 |     |     |     |     | 310 |     |     |     | 315 |     |     |     |     |     | 320 |
| Leu | Lys | Lys | Tyr | Gln | Glu | Arg | Leu | Arg | Ser | Ile | Asn | Pro | Pro | Cys | Val |
|     |     |     |     | 325 |     |     |     |     | 330 |     |     |     |     | 335 |     |
| Pro | Phe | Phe | Gly | Arg | Tyr | Leu | Thr | Asn | Ile | Leu | His | Leu | Glu | Glu | Gly |
|     |     |     | 340 |     |     |     |     | 345 |     |     |     |     | 350 |     |     |
| Asn | Pro | Asp | Leu | Leu | Ala | Asn | Thr | Glu | Leu | Ile | Asn | Phe | Ser | Lys | Arg |
|     |     | 355 |     |     |     |     | 360 |     |     |     |     | 365 |     |     |     |
| Arg | Lys | Val | Ala | Glu | Ile | Ile | Gly | Glu | Ile | Gln | Gln | Tyr | Gln | Asn | Gln |
|     | 370 |     |     |     |     | 375 |     |     |     |     | 380 |     |     |     |     |
| Pro | Tyr | Cys | Leu | Asn | Glu | Glu | Ser | Thr | Ile | Arg | Gln | Phe | Phe | Glu | Gln |
| 385 |     |     |     |     | 390 |     |     |     | 395 |     |     |     |     |     | 400 |
| Leu | Asp | Pro | Phe | Asn | Gly | Leu | Ser | Asp | Lys | Gln | Met | Ser | Asp | Tyr | Leu |
|     |     |     |     | 405 |     |     |     |     | 410 |     |     |     |     | 415 |     |
| Tyr | Asn | Glu | Ser | Leu | Arg | Ile | Glu | Pro | Arg | Gly | Cys | Lys | Thr |
|     |     |     | 420 |     |     |     |     | 425 |     |     |     |     | 430 |

( 2 ) INFORMATION FOR SEQ ID NO:10:

( i ) SEQUENCE CHARACTERISTICS:
        ( A ) LENGTH: 423 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

|     |     |     |     |     |     |     |     |     |     |     |     |     |     |     |     |
| --- | --- | --- | --- | --- | --- | --- | --- | --- | --- | --- | --- | --- | --- | --- | --- |
| Ile | Lys | Ala | Gly | Thr | Val | Leu | Lys | Leu | Ile | Glu | Arg | Leu | Thr | Tyr |
| 1   |     |     |     | 5   |     |     |     |     | 10  |     |     |     |     | 15  |
| His | Met | Tyr | Ala | Asp | Pro | Asn | Phe | Val | Arg | Thr | Phe | Leu | Thr | Thr |
|     |     |     |     | 20  |     |     |     |     | 25  |     |     |     |     | 30  |
| Tyr | Arg | Ser | Phe | Cys | Arg | Pro | Gln | Glu | Leu | Leu | Ser | Leu | Leu | Ile |
|     |     |     |     | 35  |     |     |     |     | 40  |     |     |     |     | 45  |
| Glu | Arg | Phe | Glu | Ile | Pro | Glu | Pro | Glu | Pro | Thr | Glu | Ala | Asp | Arg |
|     |     |     |     | 50  |     |     |     |     | 55  |     |     |     |     | 60  |
| Ile | Ala | Ile | Glu | Asn | Gly | Asp | Gln | Pro | Leu | Ser | Ala | Glu | Leu | Lys |
|     |     |     |     | 65  |     |     |     |     | 70  |     |     |     |     | 75  |
| Arg | Phe | Arg | Lys | Glu | Tyr | Ile | Gln | Pro | Val | Gln | Leu | Arg | Val | Leu |
|     |     |     |     | 80  |     |     |     |     | 85  |     |     |     |     | 90  |
| Asn | Val | Cys | Arg | His | Trp | Val | Glu | His | Phe | Tyr | Asp | Phe | Glu |
|     |     |     |     | 95  |     |     |     |     | 100 |     |     |     |     | 105 |
| Arg | Asp | Ala | Asp | Leu | Leu | Gln | Arg | Met | Glu | Glu | Phe | Ile | Gly | Thr |
|     |     |     |     | 110 |     |     |     |     | 115 |     |     |     |     | 120 |
| Val | Arg | Gly | Lys | Ala | Met | Lys | Lys | Trp | Val | Glu | Ser | Ile | Thr | Lys |
|     |     |     |     | 125 |     |     |     |     | 130 |     |     |     |     | 135 |
| Ile | Ile | Gln | Arg | Lys | Lys | Ile | Ala | Arg | Asp | Asn | Gly | Pro | Gly | His |
|     |     |     |     | 140 |     |     |     |     | 145 |     |     |     |     | 150 |
| Asn | Ile | Thr | Phe | Gln | Ser | Ser | Pro | Pro | Thr | Val | Glu | Trp | His | Ile |
|     |     |     |     | 155 |     |     |     |     | 160 |     |     |     |     | 165 |
| Ser | Arg | Pro | Gly | His | Ile | Glu | Thr | Phe | Asp | Leu | Leu | Thr | Leu | His |
|     |     |     |     | 170 |     |     |     |     | 175 |     |     |     |     | 180 |

Pro Ile Glu Ile Ala Arg Gln Leu Thr Leu Leu Glu Ser Asp Leu
            185                 190                 195

Tyr Arg Ala Val Gln Pro Ser Glu Leu Val Gly Ser Val Trp Thr
            200                 205                 210

Lys Glu Asp Lys Glu Ile Asn Ser Pro Asn Leu Leu Lys Met Ile
            215                 220                 225

Arg His Thr Thr Asn Leu Thr Leu Trp Phe Glu Lys Cys Ile Val
            230                 235                 240

Glu Thr Glu Asn Leu Glu Arg Val Ala Val Val Ser Arg Ile
            245                 250                 255

Ile Glu Ile Leu Gln Val Phe Gln Glu Leu Asn Asn Phe Asn Gly
            260                 265                 270

Val Leu Glu Val Val Ser Ala Met Asn Ser Ser Pro Val Tyr Arg
            275                 280                 285

Leu Asp His Thr Phe Glu Gln Ile Pro Ser Arg Gln Lys Lys Ile
            290                 295                 300

Leu Glu Glu Ala His Glu Leu Ser Glu Asp His Tyr Lys Lys Tyr
            305                 310                 315

Leu Ala Lys Leu Arg Ser Ile Asn Pro Pro Cys Val Pro Phe Phe
            320                 325                 330

Gly Ile Tyr Leu Thr Asn Ile Leu Lys Thr Glu Glu Gly Asn Pro
            335                 340                 345

Glu Val Leu Arg Arg His Gly Lys Glu Leu Ile Asn Phe Ser Lys
            350                 355                 360

Arg Arg Arg Val Ala Glu Ile Thr Gly Glu Ile Gln Gln Tyr Gln
            365                 370                 375

Asn Gln Pro Tyr Cys Leu Arg Val Glu Pro Asp Ile Lys Arg Phe
            380                 385                 390

Phe Glu Asn Leu Asn Pro Met Gly Asn Ser Met Glu Lys Glu Phe
            395                 400                 405

Thr Asp Tyr Leu Phe Asn Lys Ser Leu Glu Ile Glu Pro Arg His
            410                 415                 420

Pro Lys Pro ( 2 ) INFORMATION FOR SEQ ID NO:11:

( i ) SEQUENCE CHARACTERISTICS:
  ( A ) LENGTH: 423 amino acids
  ( B ) TYPE: amino acid
  ( D ) TOPOLOGY: linear ( i i ) MOLECULE TYPE: protein ( x i ) SEQUENCE DESCRIPTION: SEQ ID NO:11:

Ile Lys Gly Gly Thr Val Val Lys Leu Ile Glu Arg Leu Thr Tyr
 1               5                  10                  15

His Met Tyr Ala Asp Pro Asn Phe Val Arg Thr Phe Leu Thr Thr
            20                  25                  30

Tyr Arg Ser Phe Cys Lys Pro Gln Glu Leu Leu Asn Leu Leu Ile
            35                  40                  45

Glu Arg Phe Glu Ile Pro Glu Pro Glu Pro Thr Glu Ala Asp Lys
            50                  55                  60

Leu Ala Leu Glu Lys Gly Glu Gln Pro Ile Ser Ala Asp Leu Lys
            65                  70                  75

Arg Phe Arg Lys Glu Tyr Val Gln Pro Val Gln Leu Arg Val Leu
            80                  85                  90

| | | | | | | | | | | | | | | |
|---|---|---|---|---|---|---|---|---|---|---|---|---|---|---|
|Asn|Val|Phe|Arg|His 95|Trp|Val|Glu|His|His 100|Tyr|Tyr|Asp|Phe|Glu 105|
|Arg|Asp|Leu|Glu|Leu 110|Leu|Glu|Arg|Leu|Glu 115|Ser|Phe|Ile|Ser|Ser 120|
|Val|Arg|Gly|Lys|Ala 125|Met|Lys|Lys|Trp|Val 130|Glu|Ser|Ile|Ala|Lys 135|
|Ile|Ile|Lys|Arg|Lys 140|Lys|Gln|Ala|Gln|Ala 145|Asn|Gly|Ile|Ser|His 150|
|Asn|Ile|Thr|Phe|Glu 155|Ser|Ser|Pro|Pro|Val 160|Glu|Trp|His|Ile 165|
|Ser|Arg|Thr|Gly|Gln 170|Phe|Glu|Thr|Phe|Asp 175|Leu|Met|Thr|Leu|His 180|
|Pro|Ile|Glu|Ile|Ala 185|Arg|Gln|Leu|Thr|Leu 190|Leu|Glu|Ser|Asp|Leu 195|
|Tyr|Arg|Lys|Val|Gln 200|Pro|Ser|Glu|Leu|Val 205|Gly|Ser|Val|Trp|Thr 210|
|Lys|Glu|Asp|Lys|Glu 215|Ile|Asn|Ser|Pro|Asn 220|Leu|Leu|Lys|Met|Ile 225|
|Arg|His|Thr|Thr|Asn 230|Leu|Thr|Leu|Trp|Phe 235|Glu|Lys|Cys|Ile|Val 240|
|Glu|Ala|Glu|Asn|Phe 245|Glu|Glu|Arg|Val|Ala 250|Val|Leu|Ser|Arg|Ile 255|
|Val|Glu|Ile|Leu|Gln 260|Val|Phe|Gln|Asp|Leu 265|Asn|Asn|Phe|Asn|Gly 270|
|Val|Leu|Glu|Ile|Val 275|Ser|Ala|Val|Asn|Ser 280|Val|Ser|Val|Tyr|Arg 285|
|Leu|Asp|His|Thr|Phe 290|Glu|Ala|Leu|Gln|Glu 295|Arg|Lys|Arg|Ile 300|
|Leu|Asp|Asp|Ala|Val 305|Glu|Leu|Ser|Gln|Asp 310|His|Phe|Lys|Lys|Tyr 315|
|Leu|Val|Lys|Leu|Lys 320|Ser|Ile|Asn|Pro|Pro 325|Cys|Val|Pro|Phe|Phe 330|
|Gly|Ile|Tyr|Leu|Thr 335|Asn|Ile|Leu|Lys|Thr 340|Glu|Glu|Gly|Asn|Ser 345|
|Asp|Phe|Leu|Lys|Arg 350|Lys|Gly|Lys|Asp|Leu 355|Ile|Asn|Phe|Ser|Lys 360|
|Arg|Arg|Lys|Val|Ala 365|Glu|Ile|Thr|Gly|Glu 370|Ile|Gln|Gln|Tyr|Gln 375|
|Asn|Gln|Pro|Tyr|Cys 380|Leu|Arg|Thr|Glu|Pro 385|Glu|Met|Arg|Arg|Phe 390|
|Phe|Glu|Asn|Leu|Asn 395|Pro|Met|Gly|Ile|Leu 400|Ser|Glu|Lys|Glu|Phe 405|
|Thr|Asp|Tyr|Leu|Phe 410|Asn|Lys|Ser|Leu|Glu 415|Ile|Glu|Pro|Arg|Asn 420|
|Cys|Lys|Gln| | | | | | | | | | | | |

( 2 ) INFORMATION FOR SEQ ID NO:12:

( i ) SEQUENCE CHARACTERISTICS:
        ( A ) LENGTH: 426 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| | | | | | | | | | | | | | | |
|---|---|---|---|---|---|---|---|---|---|---|---|---|---|---|
| Ile | Arg | Gly | Gly | Thr | Lys | Glu | Ala | Leu | Ile | Glu | His | Leu | Thr | Ser |
| 1 | | | | 5 | | | | | 10 | | | | | 15 |
| His | Glu | Leu | Val | Asp | Ala | Ala | Phe | Asn | Val | Thr | Met | Leu | Ile | Thr |
| | | | | 20 | | | | | 25 | | | | | 30 |
| Phe | Arg | Ser | Ile | Leu | Thr | Thr | Arg | Glu | Phe | Phe | Tyr | Ala | Leu | Ile |
| | | | | 35 | | | | | 40 | | | | | 45 |
| Tyr | Arg | Tyr | Asn | Leu | Tyr | Pro | Pro | Glu | Gly | Leu | Ser | Tyr | Asp | Asp |
| | | | | 50 | | | | | 55 | | | | | 60 |
| Tyr | Asn | Ile | Trp | Ile | Glu | Lys | Lys | Ser | Asn | Pro | Ile | Lys | Cys | Arg |
| | | | | 65 | | | | | 70 | | | | | 75 |
| Val | Val | Asn | Ile | Met | Arg | Thr | Phe | Leu | Thr | Gln | Tyr | Trp | Thr | Arg |
| | | | | 80 | | | | | 85 | | | | | 90 |
| Asn | Tyr | Tyr | Glu | Pro | Gly | Ile | Pro | Leu | Ile | Leu | Asn | Phe | Ala | Lys |
| | | | | 95 | | | | | 100 | | | | | 105 |
| Met | Val | Val | Ser | Glu | Lys | Ile | Pro | Gly | Ala | Glu | Asp | Leu | Leu | Gln |
| | | | | 110 | | | | | 115 | | | | | 120 |
| Lys | Ile | Asn | Glu | Lys | Leu | Ile | Asn | Glu | Asn | Glu | Lys | Glu | Pro | Val |
| | | | | 125 | | | | | 130 | | | | | 135 |
| Asp | Pro | Lys | Gln | Gln | Asp | Ser | Val | Ser | Ala | Val | Val | Gln | Thr | Thr |
| | | | | 140 | | | | | 145 | | | | | 150 |
| Lys | Arg | Asp | Asn | Lys | Ser | Pro | Ile | His | Met | Ser | Ser | Ser | Ser | Leu |
| | | | | 155 | | | | | 160 | | | | | 165 |
| Pro | Ser | Ser | Ala | Ser | Ser | Ala | Phe | Phe | Arg | Leu | Lys | Lys | Leu | Lys |
| | | | | 170 | | | | | 175 | | | | | 180 |
| Leu | Leu | Asp | Ile | Asp | Pro | Tyr | Thr | Tyr | Ala | Thr | Gln | Leu | Thr | Val |
| | | | | 185 | | | | | 190 | | | | | 195 |
| Leu | Glu | His | Asp | Leu | Tyr | Leu | Arg | Ile | Thr | Met | Phe | Glu | Cys | Leu |
| | | | | 200 | | | | | 205 | | | | | 210 |
| Asp | Arg | Ala | Trp | Gly | Thr | Lys | Tyr | Cys | Asn | Met | Gly | Gly | Ser | Pro |
| | | | | 215 | | | | | 220 | | | | | 225 |
| Asn | Ile | Thr | Lys | Phe | Ile | Ala | Asn | Ala | Asn | Thr | Leu | Thr | Asn | Phe |
| | | | | 230 | | | | | 235 | | | | | 240 |
| Val | Ser | His | Thr | Ile | Val | Lys | Gln | Ala | Asp | Val | Lys | Thr | Arg | Ser |
| | | | | 245 | | | | | 250 | | | | | 255 |
| Lys | Leu | Thr | Gln | Tyr | Phe | Val | Thr | Val | Ala | Gln | His | Cys | Lys | Glu |
| | | | | 260 | | | | | 265 | | | | | 270 |
| Leu | Asn | Asn | Phe | Ser | Ser | Met | Thr | Ala | Ile | Val | Ser | Ala | Leu | Tyr |
| | | | | 275 | | | | | 280 | | | | | 285 |
| Ser | Ser | Pro | Ile | Tyr | Arg | Leu | Lys | Lys | Thr | Trp | Asp | Leu | Val | Ser |
| | | | | 290 | | | | | 295 | | | | | 300 |
| Thr | Glu | Ser | Lys | Asp | Leu | Leu | Lys | Asn | Leu | Asn | Asn | Leu | Met | Asp |
| | | | | 305 | | | | | 310 | | | | | 315 |
| Ser | Lys | Arg | Asn | Phe | Val | Lys | Tyr | Arg | Glu | Leu | Leu | Arg | Ser | Val |
| | | | | 320 | | | | | 325 | | | | | 330 |
| Thr | Asp | Val | Ala | Cys | Val | Pro | Phe | Phe | Gly | Val | Tyr | Leu | Ser | Asp |
| | | | | 335 | | | | | 340 | | | | | 345 |
| Leu | Thr | Phe | Thr | Phe | Val | Gly | Asn | Pro | Asp | Phe | Leu | His | Asn | Ser |
| | | | | 350 | | | | | 355 | | | | | 360 |
| Thr | Asn | Ile | Ile | Asn | Phe | Ser | Lys | Arg | Thr | Lys | Ile | Ala | Asn | Ile |
| | | | | 365 | | | | | 370 | | | | | 375 |
| Val | Glu | Glu | Ile | Ile | Ser | Phe | Lys | Arg | Phe | His | Tyr | Lys | Leu | Lys |
| | | | | 380 | | | | | 385 | | | | | 390 |
| Arg | Leu | Asp | Asp | Ile | Gln | Thr | Val | Ile | Glu | Ala | Ser | Leu | Glu | Asn |
| | | | | 395 | | | | | 400 | | | | | 405 |

| | | | | | | | | | | | | | | |
|---|---|---|---|---|---|---|---|---|---|---|---|---|---|---|
| Val | Pro | His | Ile | Glu 410 | Lys | Gln | Tyr | Gln | Leu 415 | Ser | Leu | Gln | Val | Glu 420 |
| Pro | Pro | Ser | Gly | Asn 425 | Thr | | | | | | | | | |

( 2 ) INFORMATION FOR SEQ ID NO:13:

( i ) SEQUENCE CHARACTERISTICS:
        ( A ) LENGTH: 418 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

| | | | | | | | | | | | | | | |
|---|---|---|---|---|---|---|---|---|---|---|---|---|---|---|
| Ile 1 | Lys | Gly | Gly | Ser 5 | Lys | His | Ala | Leu | Ile 10 | Ser | Tyr | Leu | Thr | Asp 15 |
| Asn | Glu | Lys | Lys | Asp 20 | Leu | Phe | Phe | Asn | Ile 25 | Thr | Phe | Leu | Ile | Thr 30 |
| Phe | Arg | Ser | Ile | Phe 35 | Thr | Thr | Thr | Glu | Phe 40 | Leu | Ser | Tyr | Leu | Ile 45 |
| Ser | Gln | Tyr | Asn | Leu 50 | Asp | Pro | Pro | Glu | Asp 55 | Leu | Cys | Phe | Glu | Glu 60 |
| Tyr | Asn | Glu | Trp | Val 65 | Thr | Lys | Lys | Leu | Ile 70 | Pro | Val | Lys | Cys | Arg 75 |
| Val | Val | Glu | Ile | Met 80 | Thr | Thr | Phe | Phe | Lys 85 | Gln | Tyr | Trp | Phe | Pro 90 |
| Gly | Tyr | Asp | Glu | Pro 95 | Asp | Leu | Ala | Thr | Leu 100 | Asn | Leu | Asp | Tyr | Phe 105 |
| Ala | Gln | Val | Ala | Ile 110 | Lys | Glu | Asn | Ile | Thr 115 | Gly | Ser | Val | Glu | Leu 120 |
| Leu | Lys | Glu | Val | Asn 125 | Gln | Lys | Phe | Lys | Leu 130 | Gly | Asn | Ile | Gln | Glu 135 |
| Ala | Thr | Ala | Pro | Met 140 | Lys | Thr | Leu | Asp | Gln 145 | Gln | Ile | Cys | Gln | Asp 150 |
| His | Tyr | Ser | Gly | Thr 155 | Leu | Tyr | Ser | Thr | Thr 160 | Glu | Ser | Ile | Leu | Ala 165 |
| Val | Asp | Pro | Val | Leu 170 | Phe | Ala | Thr | Gln | Leu 175 | Thr | Ile | Leu | Glu | His 180 |
| Glu | Ile | Tyr | Cys | Glu 185 | Ile | Thr | Thr | Phe | Asp 190 | Cys | Leu | Gln | Lys | Ile 195 |
| Trp | Lys | Asn | Lys | Tyr 200 | Thr | Lys | Ser | Tyr | Gly 205 | Ala | Ser | Pro | Gly | Leu 210 |
| Asn | Glu | Phe | Ile | Ser 215 | Phe | Ala | Asn | Lys | Leu 220 | Thr | Asn | Phe | Ile | Ser 225 |
| Tyr | Ser | Val | Val | Lys 230 | Glu | Ala | Asp | Lys | Ser 235 | Lys | Arg | Ala | Lys | Leu 240 |
| Leu | Ser | His | Phe | Ile 245 | Phe | Ile | Ala | Glu | Tyr 250 | Cys | Arg | Lys | Phe | Asn 255 |
| Asn | Phe | Ser | Ser | Met 260 | Thr | Asp | Ile | Ile | Ser 265 | Ala | Leu | Tyr | Ser | Ser 270 |
| Pro | Ile | Tyr | Arg | Leu 275 | Glu | Lys | Thr | Trp | Gln 280 | Ala | Val | Ile | Pro | Gln 285 |
| Thr | Arg | Asp | Leu | Leu 290 | Gln | Ser | Leu | Asn | Lys 295 | Leu | Met | Asp | Pro | Lys 300 |
| Lys | Asn | Phe | Ile | Asn | Tyr | Arg | Asn | Glu | Leu | Lys | Ser | Leu | His | Ser |

|     |     |     |     | 305 |     |     |     |     | 310 |     |     |     |     | 315 |
|---|---|---|---|---|---|---|---|---|---|---|---|---|---|---|
| Ala | Pro | Cys | Val | Pro | Phe | Phe | Gly | Val | Tyr | Leu | Ser | Asp | Leu | Thr |
|     |     |     |     | 320 |     |     |     |     | 325 |     |     |     |     | 330 |
| Phe | Thr | Asp | Ser | Gly | Asn | Pro | Asp | Tyr | Leu | Val | Leu | Glu | His | Gly |
|     |     |     |     | 335 |     |     |     |     | 340 |     |     |     |     | 345 |
| Leu | Lys | Gly | Val | His | Asp | Glu | Lys | Lys | Tyr | Ile | Asn | Phe | Asn | Lys |
|     |     |     |     | 350 |     |     |     |     | 355 |     |     |     |     | 360 |
| Arg | Ser | Arg | Leu | Val | Asp | Ile | Leu | Gln | Glu | Ile | Ile | Tyr | Phe | Lys |
|     |     |     |     | 365 |     |     |     |     | 370 |     |     |     |     | 375 |
| Lys | Thr | His | Tyr | Asp | Phe | Thr | Lys | Asp | Arg | Thr | Val | Ile | Glu | Cys |
|     |     |     |     | 380 |     |     |     |     | 385 |     |     |     |     | 390 |
| Ile | Ser | Asn | Ser | Leu | Glu | Asn | Ile | Pro | His | Ile | Glu | Lys | Gln | Tyr |
|     |     |     |     | 395 |     |     |     |     | 400 |     |     |     |     | 405 |
| Gln | Leu | Ser | Leu | Ile | Ile | Glu | Pro | Lys | Pro | Arg | Lys | Lys |     |     |
|     |     |     |     | 410 |     |     |     |     | 415 |     |     |     |     |     |

( 2 ) INFORMATION FOR SEQ ID NO:14:

( i ) SEQUENCE CHARACTERISTICS:
        ( A ) LENGTH: 402 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

|     |     |     |     |     |     |     |     |     |     |     |     |     |     |     |
|---|---|---|---|---|---|---|---|---|---|---|---|---|---|---|
| Ile | Lys | Thr | Ala | Thr | Leu | Val | Phe | Ile | Ile | Asn | Tyr | Leu | Leu | Arg |
| 1   |     |     |     | 5   |     |     |     |     | 10  |     |     |     |     | 15  |
| Thr | Asp | Ile | Asp | Ser | Thr | Phe | Phe | Thr | Thr | Ile | Phe | Leu | Asn | Thr |
|     |     |     |     | 20  |     |     |     |     | 25  |     |     |     |     | 30  |
| Tyr | Ala | Ser | Met | Ile | Ser | Ser | Ser | Asp | Leu | Phe | Ser | Ile | Leu | Gly |
|     |     |     |     | 35  |     |     |     |     | 40  |     |     |     |     | 45  |
| Ala | His | Phe | Arg | Phe | Ile | Cys | Ser | Leu | Asn | Phe | Gly | Lys | Ile | Ser |
|     |     |     |     | 50  |     |     |     |     | 55  |     |     |     |     | 60  |
| Phe | Ile | Ser | His | Glu | Phe | Tyr | Arg | Val | Ser | Lys | Arg | Phe | Leu | Asp |
|     |     |     |     | 65  |     |     |     |     | 70  |     |     |     |     | 75  |
| Ile | Leu | Leu | Ile | Trp | Phe | Glu | Ser | Tyr | Leu | Val | Glu | Glu | Leu | Asp |
|     |     |     |     | 80  |     |     |     |     | 85  |     |     |     |     | 90  |
| Asn | Ser | Lys | Ser | Ile | Phe | Phe | Leu | Phe | Lys | Ile | Tyr | Lys | Val | Phe |
|     |     |     |     | 95  |     |     |     |     | 100 |     |     |     |     | 105 |
| Glu | Val | Phe | Val | Val | Pro | His | Phe | Ala | Ser | Ala | Glu | Glu | Leu | Leu |
|     |     |     |     | 110 |     |     |     |     | 115 |     |     |     |     | 120 |
| His | Ser | Leu | Ser | His | Leu | Leu | His | His | Pro | Ser | Thr | Lys | Arg | Ser |
|     |     |     |     | 125 |     |     |     |     | 130 |     |     |     |     | 135 |
| His | Lys | Met | Leu | Glu | Gly | Lys | Glu | Leu | Ser | Gln | Glu | Leu | Glu | Asp |
|     |     |     |     | 140 |     |     |     |     | 145 |     |     |     |     | 150 |
| Leu | Ser | Leu | His | Asn | Ser | Pro | Asp | Pro | Ile | Ile | Tyr | Lys | Asp | Glu |
|     |     |     |     | 155 |     |     |     |     | 160 |     |     |     |     | 165 |
| Leu | Val | Leu | Leu | Leu | Pro | Pro | Arg | Glu | Ile | Ala | Lys | Gln | Leu | Cys |
|     |     |     |     | 170 |     |     |     |     | 175 |     |     |     |     | 180 |
| Ile | Leu | Glu | Phe | Gln | Ser | Phe | Ser | His | Ile | Ser | Arg | Ile | Gln | Phe |
|     |     |     |     | 185 |     |     |     |     | 190 |     |     |     |     | 195 |
| Leu | Thr | Lys | Ile | Trp | Asp | Glu | Leu | Asn | Arg | Phe | Ser | Pro | Lys | Glu |
|     |     |     |     | 200 |     |     |     |     | 205 |     |     |     |     | 210 |
| Lys | Thr | Ser | Thr | Phe | Tyr | Leu | Ser | Asn | His | Leu | Val | Asn | Phe | Val |
|     |     |     |     | 215 |     |     |     |     | 220 |     |     |     |     | 225 |

```
Thr  Glu  Thr  Ile  Val  Gln  Glu  Glu  Glu  Pro  Arg  Arg  Arg  Thr  Asn
               230                      235                         240

Val  Leu  Ala  Tyr  Phe  Ile  Gln  Val  Cys  Asp  Tyr  Leu  Arg  Glu  Leu
               245                      250                         255

Asn  Asn  Phe  Ala  Ser  Leu  Phe  Ser  Ile  Ile  Ser  Ala  Leu  Asn  Ser
               260                      265                         270

Ser  Pro  Ile  His  Arg  Leu  Arg  Lys  Thr  Trp  Ala  Asn  Leu  Asn  Ser
               275                      280                         285

Lys  Thr  Leu  Ala  Ser  Phe  Glu  Leu  Leu  Asn  Asn  Leu  Thr  Glu  Ala
               290                      295                         300

Arg  Lys  Asn  Phe  Ser  Asn  Tyr  Arg  Asp  Cys  Leu  Glu  Asn  Cys  Val
               305                      310                         315

Leu  Pro  Cys  Val  Pro  Phe  Leu  Gly  Val  Tyr  Phe  Thr  Asp  Leu  Thr
               320                      325                         330

Phe  Leu  Lys  Thr  Gly  Asn  Lys  Asp  Asn  Phe  Gln  Asn  Met  Ile  Asn
               335                      340                         345

Phe  Asp  Lys  Arg  Thr  Lys  Val  Thr  Arg  Ile  Leu  Asn  Glu  Ile  Lys
               350                      355                         360

Lys  Phe  Gln  Ser  Val  Gly  Tyr  Met  Phe  Asn  Pro  Ile  Asn  Glu  Val
               365                      370                         375

Gln  Glu  Leu  Leu  Asn  Glu  Val  Ile  Ser  Arg  Glu  Arg  Asn  Thr  Asn
               380                      385                         390

Asn  Ile  Tyr  Gln  Arg  Ser  Leu  Thr  Val  Glu  Pro  Arg
               395                      400
```

( 2 ) INFORMATION FOR SEQ ID NO:15:

( i ) SEQUENCE CHARACTERISTICS:
        ( A ) LENGTH: 362 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Pro  Ser  Pro  Phe  Asp  Ser  Ala  Asn  Leu  Leu  Asn  Phe  Arg  Asp
 1             5                      10                         15

Trp  Thr  Thr  Asp  Asn  Ala  Leu  Leu  Gln  Glu  Leu  Leu  Leu  Ser  Tyr
               20                       25                         30

Pro  Thr  Ile  Asn  Lys  Asn  Lys  His  Lys  Asn  His  Ser  Val  Pro  Arg
               35                       40                         45

Leu  Ile  Gln  Ile  Trp  Val  Glu  Ser  Tyr  Trp  Gln  Asp  Ser  Glu  Thr
               50                       55                         60

Thr  Leu  Lys  Asp  Ile  Leu  Asn  Phe  Trp  Tyr  Ser  His  Leu  Ala  Glu
               65                       70                         75

Tyr  Tyr  Glu  Tyr  Gln  Glu  Leu  Phe  Ala  Asp  Ile  Val  Gln  Leu  Phe
               80                       85                         90

Ile  Asn  Lys  Lys  Arg  Thr  Arg  Gln  Leu  Lys  Ile  His  Tyr  Ile  Gly
               95                      100                        105

Leu  Thr  Asp  Lys  Glu  Ile  Glu  Glu  Asn  Lys  Pro  Pro  Leu  Asp  Tyr
              110                      115                        120

Glu  Asn  Leu  Phe  Leu  Gln  Tyr  Glu  Ile  Asp  Lys  Thr  Asn  Ala  Asn
              125                      130                        135

Asp  Glu  Leu  Cys  Gly  Ala  Thr  Asp  Leu  Ser  Asp  Leu  Leu  Phe  Gln
              140                      145                        150

Trp  Lys  Gln  Gly  Glu  Pro  Leu  Glu  Val  Glu  Ala  Phe  Ala  Leu  Asn
              155                      160                        165
```

| | | | | | | | | | | | | | | |
|---|---|---|---|---|---|---|---|---|---|---|---|---|---|---|
| Val | Ser | Pro | Trp | Ser 170 | Leu | Ala | Lys | Thr 175 | Thr | Leu | Leu | Glu | Ser 180 | |
| Ser | Leu | Tyr | Leu | Asp 185 | Ile | Glu | Thr | Ile | Glu 190 | Phe | Thr | Arg | His | Phe 195 |
| Lys | His | Asn | Asp | Thr 200 | Thr | Ile | Asp | Ser | Val 205 | Phe | Thr | Leu | Ser | Asn 210 |
| Gln | Leu | Ser | Ser | Tyr 215 | Val | Leu | Glu | Thr | Thr 220 | Leu | Gln | Gln | Thr | His 225 |
| Thr | Ile | Ser | Tyr | Trp 230 | Leu | Gln | Val | Ala | Leu 235 | Ala | Cys | Leu | Tyr | Leu 240 |
| Arg | Asn | Leu | Asn | Ser 245 | Leu | Ala | Ser | Ile | Ile 250 | Thr | Ser | Leu | Gln | Asn 255 |
| His | Ser | Ile | Glu | Arg 260 | Leu | Ser | Leu | Pro | Ile 265 | Asp | Val | Lys | Ser | Asp 270 |
| His | Leu | Phe | Gln | Arg 275 | Leu | Lys | Val | Val | Val 280 | His | Pro | Asn | Asn | Asn 285 |
| Tyr | Asn | Val | Tyr | Arg 290 | Arg | Thr | Ile | Lys | His 295 | Ile | Phe | His | Ser | Gln 300 |
| Leu | Pro | Cys | Val | Pro 305 | Phe | Thr | Ser | Leu | Leu 310 | Ile | Arg | Asp | Ile | Thr 315 |
| Phe | Ile | Arg | Asp | Gly 320 | Asn | Asp | Thr | Phe | Thr 325 | Lys | Asp | Gly | Asn | Asn 330 |
| Val | Asn | Met | Gln | Lys 335 | Phe | Asn | Gln | Ile | Thr 340 | Lys | Ile | Val | Ala | Phe 345 |
| Ala | Gln | Tyr | Leu | Gln 350 | Gln | Lys | Gln | Tyr | Glu 355 | Asp | Ile | His | Cys | Ser 360 |
| Asn | Thr | | | | | | | | | | | | | |